(12) United States Patent
Dalby et al.

(10) Patent No.: US 10,280,422 B2
(45) Date of Patent: *May 7, 2019

(54) MIR-92 INHIBITORS AND USES THEREOF

(71) Applicant: MIRAGEN THERAPEUTICS, INC., Boulder, CO (US)

(72) Inventors: Christina Marie Dalby, Boulder, CO (US); Corrie Lynn Gallant-Behm, Erie, CO (US); Aimee Jackson, Louisville, CO (US); Kathryn Hutnick, Niwot, CO (US); Anita Seto, Golden, CO (US)

(73) Assignee: MIRAGEN THERAPEUTICS, INC., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/878,176

(22) Filed: Jan. 23, 2018

(65) Prior Publication Data

US 2018/0237779 A1    Aug. 23, 2018

Related U.S. Application Data

(63) Continuation of application No. 15/001,968, filed on Jan. 20, 2016, now Pat. No. 9,885,042.

(60) Provisional application No. 62/105,546, filed on Jan. 20, 2015.

(51) Int. Cl.
    *C12N 15/113* (2010.01)

(52) U.S. Cl.
    CPC ...... *C12N 15/113* (2013.01); *C12N 2310/113* (2013.01); *C12N 2310/315* (2013.01); *C12N 2310/3231* (2013.01); *C12N 2310/3341* (2013.01)

(58) Field of Classification Search
    CPC ............... C12N 15/111; C12N 15/113; C12N 2310/113
    See application file for complete search history.

(56) References Cited

U.S. PATENT DOCUMENTS

| | | | |
|---|---|---|---|
| 5,783,565 A | 7/1998 | Lee et al. |
| 5,837,533 A | 11/1998 | Boutin |
| 5,981,505 A | 11/1999 | Weiner et al. |
| 6,127,170 A | 10/2000 | Boutin |
| 6,217,900 B1 | 4/2001 | Ciccarelli et al. |
| 6,261,587 B1 | 7/2001 | Usala et al. |
| 6,268,490 B1 | 7/2001 | Imanishi et al. |
| 6,316,198 B1 | 11/2001 | Skouv et al. |
| 6,379,965 B1 | 4/2002 | Boutin |
| 6,383,512 B1 | 5/2002 | Ciccarelli et al. |
| 6,403,566 B1 | 6/2002 | Wang |
| 6,416,510 B1 | 7/2002 | Altman et al. |
| 6,670,461 B1 | 12/2003 | Wengel et al. |
| 6,716,196 B2 | 4/2004 | Lesh et al. |
| 6,747,014 B2 | 6/2004 | Teng et al. |
| 6,770,748 B2 | 8/2004 | Imanishi et al. |
| 6,833,361 B2 | 12/2004 | Hong et al. |
| 6,953,466 B2 | 10/2005 | Palasis et al. |
| 6,998,484 B2 | 2/2006 | Koch et al. |
| 7,034,133 B2 | 4/2006 | Wengel et al. |
| 7,202,227 B2 | 4/2007 | Boutin |
| 7,232,806 B2 | 6/2007 | Tuschl et al. |
| 7,404,969 B2 | 7/2008 | Chen et al. |
| 7,687,617 B2 | 3/2010 | Thrue et al. |
| 8,222,221 B2 | 7/2012 | Corey et al. |
| 8,258,113 B2 | 9/2012 | Dimmeler et al. |
| 8,304,397 B2 | 11/2012 | Olson et al. |
| 8,481,507 B2 | 7/2013 | Olson et al. |
| 8,642,751 B2 | 2/2014 | Dalby et al. |
| 8,912,158 B2 | 12/2014 | Dimmeler et al. |
| 9,163,235 B2 | 10/2015 | van Rooij et al. |
| 9,255,267 B2 | 2/2016 | Mendell et al. |
| 9,279,123 B2 | 3/2016 | Dimmeler et al. |
| 9,388,408 B2 | 7/2016 | van Rooij et al. |
| 9,803,202 B2 | 10/2017 | van Rooij et al. |
| 9,862,949 B2 | 1/2018 | Dimmeler et al. |
| 9,885,042 B2 | 2/2018 | Dalby et al. |
| 2005/0059005 A1 | 3/2005 | Tuschl et al. |
| 2005/0261218 A1 | 11/2005 | Esau et al. |
| 2006/0148742 A1 | 7/2006 | Kaye et al. |
| 2006/0185027 A1 | 8/2006 | Bartel et al. |
| 2007/0060907 A1 | 3/2007 | Shapland et al. |
| 2007/0203445 A1 | 8/2007 | Kaye et al. |
| 2007/0287179 A1 | 12/2007 | Tuschl et al. |
| 2007/0292878 A1 | 12/2007 | Raymond |
| 2008/0026951 A1 | 1/2008 | Brown et al. |

(Continued)

FOREIGN PATENT DOCUMENTS

| | | |
|---|---|---|
| CN | 101386848 A | 3/2009 |
| DE | 102007052114 A1 | 5/2009 |

(Continued)

OTHER PUBLICATIONS

Banerjee, J. et al. (2010). "MicroRNAs in skin and wound healing," *Physio. Genomics* 43:543-556.
Bonauer, A. et al. (2009). "The microRNA—17-92 cluster: Still a miRacle?" *Cell Cycle* 8:3866-3873.
Dimmeler, S. (2014). "The microRNAs: Novel therapeutic targets in cardiovascular disease," 47th Annual New York Cardiovascular Symposium, Dec. 12-14, 2014, located at http://www.acc.org/~/media/Non-Clinical/Files-PDFs-Excel-MS-Word-etc/Meetings/2014/Course%20PDFs/NYCVS%202014%20PDF/Sunday/Sun%207%2030%20am%20Dimmeler%20miR%20Therapies.pdf, 31 total pages.
Iaconetti, C. et al. (2012). "Inhibition of miR-92a increases endothelial proliferation and migration in vitro as well as reduces neointimal proliferation in vivo after vascular injury," *Basic Res. In Cardiology* 107:1-14.

(Continued)

*Primary Examiner* — J. E. Angell
(74) *Attorney, Agent, or Firm* — Cooley LLP

(57) ABSTRACT

The present invention provides oligonucleotide inhibitors of miR-92 and methods of using said inhibitors for inhibiting the function and/or activity of miR-92 in a subject in need thereof. The present invention also provides methods for evaluating or monitoring the efficacy of a therapeutic for promoting wound healing and selecting a subject for treatment with a therapeutic that modulates miR-92 function and/or activity.

42 Claims, 9 Drawing Sheets

Specification includes a Sequence Listing.

(56) References Cited

U.S. PATENT DOCUMENTS

| | | |
|---|---|---|
| 2008/0050744 A1 | 2/2008 | Brown et al. |
| 2008/0176766 A1 | 7/2008 | Brown et al. |
| 2008/0214437 A1 | 9/2008 | Mohapatra et al. |
| 2009/0105174 A1 | 4/2009 | Jayasena |
| 2009/0137504 A1 | 5/2009 | Echwald et al. |
| 2009/0143326 A1 | 6/2009 | Obad et al. |
| 2009/0180957 A1 | 7/2009 | Olson et al. |
| 2009/0286969 A1 | 11/2009 | Esau et al. |
| 2009/0291906 A1 | 11/2009 | Esau et al. |
| 2009/0291907 A1 | 11/2009 | Esau et al. |
| 2009/0293148 A1 | 11/2009 | Ren et al. |
| 2009/0326049 A1 | 12/2009 | Aristarkhov et al. |
| 2010/0004320 A1 | 1/2010 | Elmen et al. |
| 2010/0029003 A1 | 2/2010 | Bartel et al. |
| 2010/0173288 A1 | 7/2010 | Zhang et al. |
| 2010/0184821 A1 | 7/2010 | Mendell et al. |
| 2010/0210712 A1 | 8/2010 | Hansen et al. |
| 2010/0257618 A1 | 10/2010 | Croce et al. |
| 2010/0267804 A1 | 10/2010 | Port et al. |
| 2010/0269183 A1 | 10/2010 | Olson et al. |
| 2010/0280094 A1 | 11/2010 | Beuvink et al. |
| 2010/0292297 A1 | 11/2010 | Wang et al. |
| 2010/0298410 A1 | 11/2010 | Obad et al. |
| 2010/0324118 A1 | 12/2010 | Dimmeler et al. |
| 2011/0071211 A1 | 3/2011 | Thum et al. |
| 2011/0076322 A1 | 3/2011 | Panzner et al. |
| 2011/0086348 A1 | 4/2011 | Prasad et al. |
| 2011/0098338 A1 | 4/2011 | Hajjar et al. |
| 2011/0105593 A1 | 5/2011 | Steel et al. |
| 2011/0117560 A1 | 5/2011 | Spinale et al. |
| 2011/0152352 A1 | 6/2011 | Hata et al. |
| 2011/0160285 A1 | 6/2011 | Anderson et al. |
| 2011/0224277 A1 | 9/2011 | Esau et al. |
| 2011/0294869 A1 | 12/2011 | Petersen |
| 2011/0313019 A1 | 12/2011 | Swayze et al. |
| 2012/0035243 A1 | 2/2012 | Olson et al. |
| 2012/0041052 A1 | 2/2012 | Beuvink et al. |
| 2012/0083596 A1 | 4/2012 | Elmén et al. |
| 2012/0114744 A1 | 5/2012 | Beuvink et al. |
| 2012/0165392 A1 | 6/2012 | Olson et al. |
| 2012/0172416 A1 | 7/2012 | Velin et al. |
| 2012/0322851 A1 | 12/2012 | Hardee et al. |
| 2012/0322856 A1 | 12/2012 | Dimmeler et al. |
| 2013/0078225 A1 | 3/2013 | Zeng et al. |
| 2013/0079505 A1 | 3/2013 | Moeller et al. |
| 2013/0096290 A1 | 4/2013 | Brown |
| 2013/0109738 A1 | 5/2013 | Chang et al. |
| 2013/0116303 A1 | 5/2013 | Zeiher et al. |
| 2013/0137753 A1 | 5/2013 | Samant et al. |
| 2013/0150256 A1 | 6/2013 | Synnergren et al. |
| 2013/0156845 A1 | 6/2013 | Manoharan et al. |
| 2013/0157883 A1 | 6/2013 | Keller et al. |
| 2013/0171242 A1 | 7/2013 | Lim et al. |
| 2013/0344135 A1 | 12/2013 | van Rooij et al. |
| 2013/0345288 A1 | 12/2013 | van Rooij et al. |
| 2014/0187603 A1 | 7/2014 | Dalby et al. |
| 2014/0303236 A1 | 10/2014 | van Rooij et al. |
| 2015/0018407 A1 | 1/2015 | Dimmeler et al. |
| 2016/0251720 A1 | 9/2016 | Schulze et al. |
| 2018/0119222 A1 | 5/2018 | Zou et al. |
| 2018/0273944 A1 | 9/2018 | van Rooij et al. |

FOREIGN PATENT DOCUMENTS

| | | | |
|---|---|---|---|
| EP | 1959012 A2 | 8/2008 | |
| EP | 1959012 A3 | 8/2008 | |
| EP | 2113567 A1 | 11/2009 | |
| EP | 2194129 A2 | 6/2010 | |
| EP | 2194129 A3 | 6/2010 | |
| EP | 2208798 A1 | 7/2010 | |
| EP | 2388327 A1 | 11/2011 | |
| EP | 2388328 A1 | 11/2011 | |
| EP | 2447274 A2 | 5/2012 | |
| EP | 2447274 A3 | 5/2012 | |
| EP | 2205737 B1 | 2/2013 | |
| EP | 2559442 A1 | 2/2013 | |
| EP | 2604690 A1 | 6/2013 | |
| EP | 2610342 A1 | 7/2013 | |
| EP | 3 294 910 A1 | 3/2018 | |
| WO | WO 01/25478 A1 | 4/2001 | |
| WO | WO 03/093449 A2 | 11/2003 | |
| WO | WO 03/093449 A3 | 11/2003 | |
| WO | WO 2005/013901 A2 | 2/2005 | |
| WO | WO 2005/013901 A3 | 2/2005 | |
| WO | WO 2005/017145 A1 | 2/2005 | |
| WO | WO 2005/078096 A2 | 8/2005 | |
| WO | WO 2005/078096 A3 | 8/2005 | |
| WO | WO 2005/078139 A2 | 8/2005 | |
| WO | WO 2005/078139 A3 | 8/2005 | |
| WO | WO 2005/079397 A2 | 9/2005 | |
| WO | WO 2005/079397 A3 | 9/2005 | |
| WO | WO 2005/082440 A1 | 9/2005 | |
| WO | WO 2005/118806 A2 | 12/2005 | |
| WO | WO 2005/118806 A3 | 12/2005 | |
| WO | WO 2006/063356 A1 | 6/2006 | |
| WO | WO 2006/089340 A2 | 8/2006 | |
| WO | WO 2006/089340 A3 | 8/2006 | |
| WO | WO 2006/111512 A1 | 10/2006 | |
| WO | WO 2006/133022 A2 | 12/2006 | |
| WO | WO 2006/133022 A3 | 12/2006 | |
| WO | WO 2006/137941 A2 | 12/2006 | |
| WO | WO 2006/137941 A3 | 12/2006 | |
| WO | WO 2007/000668 A2 | 1/2007 | |
| WO | WO 2007/000668 A3 | 1/2007 | |
| WO | WO 2007/070483 A2 | 6/2007 | |
| WO | WO 2007/070483 A3 | 6/2007 | |
| WO | WO 2007/090073 A2 | 8/2007 | |
| WO | WO 2007/090073 A3 | 8/2007 | |
| WO | WO 2007/112754 A2 | 10/2007 | |
| WO | WO 2007/112754 A3 | 10/2007 | |
| WO | WO 2008/014008 A2 | 1/2008 | |
| WO | WO 2008/014008 A3 | 1/2008 | |
| WO | WO 2008/016924 A2 | 2/2008 | |
| WO | WO 2008/016924 A3 | 2/2008 | |
| WO | WO 2008/042231 A2 | 4/2008 | |
| WO | WO 2008/042231 A3 | 4/2008 | |
| WO | WO 2008/043521 A2 | 4/2008 | |
| WO | WO 2008/061537 A2 | 5/2008 | |
| WO | WO 2008/061537 A3 | 5/2008 | |
| WO | WO 2008/070082 A2 | 6/2008 | |
| WO | WO 2008/070082 A3 | 6/2008 | |
| WO | WO 2008/074328 A2 | 6/2008 | |
| WO | WO 2008/074328 A3 | 6/2008 | |
| WO | WO 2008/076324 A2 | 6/2008 | |
| WO | WO 2008/076324 A3 | 6/2008 | |
| WO | WO 2008/147839 A1 | 12/2008 | |
| WO | WO 2009/004632 A2 | 1/2009 | |
| WO | WO 2009/004632 A3 | 1/2009 | |
| WO | WO 2009/012468 A2 | 1/2009 | |
| WO | WO 2009/012468 A3 | 1/2009 | |
| WO | WO 2009/026576 A1 | 2/2009 | |
| WO | WO 2009/043353 A2 | 4/2009 | |
| WO | WO 2009/043353 A3 | 4/2009 | |
| WO | WO-2009/056116 A1 | 5/2009 | |
| WO | WO 2009/058818 A2 | 5/2009 | |
| WO | WO 2009/058818 A3 | 5/2009 | |
| WO | WO 2009/062169 A2 | 5/2009 | |
| WO | WO 2009/062169 A3 | 5/2009 | |
| WO | WO 2009/114681 A2 | 9/2009 | |
| WO | WO 2009/114681 A3 | 9/2009 | |
| WO | WO 2009/149182 A1 | 12/2009 | |
| WO | WO 2010/000665 A1 | 1/2010 | |
| WO | WO 2010/048585 A2 | 4/2010 | |
| WO | WO 2010/048585 A3 | 4/2010 | |
| WO | WO 2010/091204 A1 | 8/2010 | |
| WO | WO 2010/129672 A1 | 11/2010 | |
| WO | WO 2010/144485 A1 | 12/2010 | |
| WO | WO-2011/017408 A1 | 2/2011 | |
| WO | WO 2011/139911 A2 | 11/2011 | |
| WO | WO 2011/139911 A3 | 11/2011 | |
| WO | WO 2011/154553 A2 | 12/2011 | |
| WO | WO 2011/154553 A3 | 12/2011 | |
| WO | WO 2011/158191 A1 | 12/2011 | |
| WO | WO 2012/006577 A2 | 1/2012 | |

(56) References Cited

FOREIGN PATENT DOCUMENTS

| WO | WO 2012/006577 A3 | 1/2012 |
|---|---|---|
| WO | WO 2012/020307 A2 | 2/2012 |
| WO | WO 2012/020307 A3 | 2/2012 |
| WO | WO 2012/027206 A1 | 3/2012 |
| WO | WO 2012/037254 A1 | 3/2012 |
| WO | WO 2012/06181 A1 | 5/2012 |
| WO | WO-2012/065024 A1 | 5/2012 |
| WO | WO 2012/083005 A2 | 6/2012 |
| WO | WO 2012/083005 A3 | 6/2012 |
| WO | WO 2012/149646 A1 | 11/2012 |
| WO | WO 2013/052965 A2 | 4/2013 |
| WO | WO 2013/052965 A3 | 4/2013 |
| WO | WO 2013/054113 A1 | 4/2013 |
| WO | WO 2013/057527 A2 | 4/2013 |
| WO | WO 2013/057527 A3 | 4/2013 |
| WO | WO 2013/059496 A1 | 4/2013 |
| WO | WO 2013/087907 A1 | 6/2013 |
| WO | WO 2013/088338 A1 | 6/2013 |
| WO | WO 2013/090457 A2 | 6/2013 |
| WO | WO 2013/090457 A3 | 6/2013 |
| WO | WO-2013/192576 A2 | 12/2013 |
| WO | WO-2013/192576 A3 | 12/2013 |
| WO | WO-2014/115103 A1 | 7/2014 |
| WO | WO-2016/118612 A2 | 7/2016 |
| WO | WO-2016/118612 A3 | 7/2016 |
| WO | WO-2018/183127 A1 | 10/2018 |

OTHER PUBLICATIONS

Murata, K. et al. (2013). "Inhibition of miR-92a enhances fracture healing via promoting angiogenesis in a model of stabilized fracture in young mice," *J. Bone and Mineral Res.* 29:316-326.

Partial Supplementary European Search Report dated Jun. 15, 2018, for EP Application No. 16 740 666.9, filed on Jan. 20, 2016, 18 pages.

Schafer, F. et al. (2013). "Regulating angiogenesis with light-inducible antimiRs," *Angewandte Chemie International Edition* 52:13558-13561.

International Search Report dated Jul. 10, 2018, for PCT Application No. PCT/US2018/024167, filed on Mar. 23, 2018, 4 pages.

Written Opinion of the International Searching Authority dated Jul. 10, 2018, for PCT Application No. PCT/US2018/024167, filed on Mar. 23, 2018, 4 pages.

Bellera et al. "Single Intracoronary Injection of Encapsulated Antagomir-92a Promotes Angiogenesis and Prevents Adverse Infarct Remodeling," Journal of the American Heart Association, Sep. 19, 2014, vol. 3, No. 5, e000946, pp. 1-22.

Nabeebaccus et al. "Heart failure-potential new targets for therapy," British Medical Bulletin, Jun. 30, 2016, vol. 119, No. 1, pp. 99-110.

Extended European Search Report dated Sep. 17, 2018, for EP Application No. 16 740 666.9, flied on Jan. 20, 2016, 16 pages.

Ambros, "MicroRNA Pathways in Flies and Worms: Growth, Death, Fat, Stress, and Timing," Cell 113:673-676 (2003).

Ambros, "The functions of animal microRNAs," Nature 431:350-355 (2004).

Bartel, "MicroRNAs: Target Recognition and Regulatory Functions," Cell 136:215-233 (2009).

Bonauer et al., "MicroRNA-92a controls angiogenesis and functional recovery of ischemic tissues in mice," 2009, Science, vol. 324, pp. 1710-1713.

Buchberger et al., "The Evidence for the Use of Growth Factors and Active Skin Substitutes for the Treatment of Non-Infected Diabetic Foot Ulcers (DFU): A Health Technology Assessment (HTA)," Experimental and Clinical Endocrinology and Diabetes 119:472-479 (2011).

Calin et al., "Human microRNA genes are frequently located at fragile sites and genomic regions involved in cancers," Proc. Natl. Acad. Sci. USA 101:2999-3004 (2004).

Calin et al., "Frequent deletions and down-regulation of micro-RNA genes miR15 and miR16 at 13q14 in chronic lymphocytic leukemia," Proc. Natl. Acad. Sci. USA 99(24):15524-15529 (2002).

Caruthers et al., "New chemical methods for synthesizing polynucleotides," Nucleic Acids Symp. Ser. 7:215-23 (1980).

Chien, "MicroRNAs and the tell-tale heart," Nature 447:389-390 (2007).

Diaz et al., "Tissue Sample Collection for Proteomics Analysis," Clinical Proteolytics: Methods and Protocols, vol. 428 in Methods in Molecular Biology, Ed. Antonia Vlahou, Chapter 3, pp. 43-53 (2008).

Database EMBL, Accession No. AB176708, May 10, 2004, XP-002339404.

Davis et al., "Potent inhibition of microRNA in vivo without degradation," Nucleic Acids Research, 2009, vol. 37, No. 1, p. 70-77.

Dews, M. et al., "Augmentation of tumor angiogenesis by a Myc-activated microRNA cluster" Nature Genetics, Sep. 2006, pp. 1060-1065, vol. 38, No. 9.

Dillin and Kelly "The Yin-Yang of Sirtuins," Science 317(5837):461-462 (2007).

European Search Report, EP appl. No. 13179144.4, 8 pages (dated Dec. 16, 2013).

European Search Report, EP appl. No. 13179146.9, 8 pages (dated Dec. 16, 2013).

Guo et al., "Mammalian microRNAs predominantly act to decrease target mRNA levels," Nature 466:835-840 (2010).

Hammond, "MicroRNA therapeutics: a new niche for antisense nucleic acids," TRENDS in Molecular Medicine, 2006, vol. 12, p. 99-101.

Hinkel, R. et al. (2013). "Inhibition of microRNA-92a protects against ischemia/reperfusion injury in a large-animal model," *Circulation* 128:1066-1075.

International Preliminary Report on Patentability for International Application No. PCT/US2011/065121, dated Jun. 18, 2013, 9 pages.

International Search Report, appl. No. PCT/DE2008/001759, 5 pages (dated Apr. 2, 2009).

International Search Report and Written Opinion for International Application No. PCT/US2011/065121, dated Jun. 5, 2012, 13 pages.

International Search Report and Written Opinion for International Application No. PCT/US2013/047157, dated Feb. 10, 2014, 12 pages.

International Search Report dated Jul. 15, 2016, for PCT Application No. PCT/US2016/014108, filed on Jan. 20, 2016, 5 pages.

Kartha and Subramanian, "MicroRNAs in Cardiovascular Diseases: Biology and Potential Clinical Applications," J. Cardiovasc. Transl. Res. 3:256-270 (2010).

Krutzfeldt et al., Silencing of microRNAs in vivo with antagomirs, 2005, Nature, vol. 438, pp. 685-689.

Kuehbacher A. et al., "Role of dicer and drosha for endothelial microRNA expression and angiogenesis" Circulation Research, Jul. 6, 2007, pp. 59-68, vol. 101, No. 6.

Kuehbacher, A. et al., "Targeting microRNA expression to regulate angiogenesis" Trends in Pharmacological Sciences, Dec. 18, 2007, pp. 12-15, vol. 29, No. 1.

Kuehbacher et al.., "Abstract 896: Identification of Pro- and Anti-angiogenic MicroRNAs," Oct. 16, 2007, Circulation, vol. 116, No. 16, II_175, American Heart Association, United States.

Kuhlencordt et al., "Accelerated atheroscleros, aortic aneurysm formation, and ischemic heart disease in apolipoprotein E/endothelial nitric oxide synthase double-knockout mice," 2001 , Circulation, vol. 104, pp. 448-454.

Kuehbacher et al., "Abstract 5443: MicroRNA 92a Controls Vessel Growth and Functional Recovery After Ischemia," Circulation 118(18 Suppl.):S_550 (2008).

Landgraf et al., "A Mammalian microRNA Expression Atlas Based on Small RNA Library Sequencing," Cell 129:1401-14 (2007).

Lei et al., "Inhibition of miR-92b suppresses nonsmall cell lung cancer cells growth and motility by targeting RECK," Mol. Cell. Biochem. 387-171-176 (2014).

Loyer et al., "Inhibition of microRNA-92a Prevents Endothelial Dysfunction and Atherosclerosis in Mice," Circulation Research: Journal of the American Heart Association, published online Nov.

(56) References Cited

OTHER PUBLICATIONS 19, 2013, http://www.circres.ahajournals.org/content/early/2013/11/19/CIRCRESAHA.114.302213, Circulation Research 114:434-443 (2014).
Montgomery, R. L. et al., "Therapeutic inhibition of miR-208a improves cardiac function and survival during heart failure + supplemental material," Circulation, 124(14):1537-1547 (2011).
Notice of Allowance dated Sep. 29, 2017, for U.S. Appl. No. 15/001,968, filed Jan. 20, 2016, 8 pages.
Non-Final Office Action dated Apr. 19, 2017, for U.S. Appl. No. 15/001,968, filed Jan. 20, 2016, 11 pages.
Office Action for U.S. Appl. No. 13/327,507, dated Feb. 27, 2013, 24 pages.
Office Action for U.S. Appl. No. 14/107,784, dated Oct. 23, 2014, 26 pages.
Pfeffer et al., "Identification of Virus-Encoded MicroRNAs," Science 304:734-736 (2004).
Reed et al., "Are aortic aneurysms caused by atherosclerosis?," 1992, Circulation, vol. 85, pp. 205-211.
"Remington's Pharmaceutical Sciences" 15th Edition, pp. 1035-1038 and 1570-1580 (1975).
Supplementary European Search Report, EP appl. No. 13807536.1, 6 pages (dated Jan. 12, 2016).
Tammen, "Specimen Collection and Handling," Clinical Proteolytics: Methods and Protocols, vol. 428 in Methods in Molecular Biology, Ed. Antonia Vlahou, Chapter 2, pp. 35-42 (2008).
Tsuchida et al., "miR-92 is a key oncogenic component of the miR-17-92 cluster in colon cancer," Cancer Sci. 102:2264-2271 (2011).
Urbich et al., "Role of microRNAs in vascular diseases, inflammation, and angiogenesis," Cardiovasc. Res. 79:581-588 (2008).
Van Rooij and Olson, "MicroRNAs; powerful new regulators of heart disease and provocative therapeutic targets," J. Clin. Invest. 117(9):2369-2376 (2007).
Venturini, L. et al., "Expression of the miR-17-92 polycistron in chronic myeloid leukemia (CML) CD34+ cells" Blood, May 15, 2007, pp. 4399-4405, vol. 109, No. 10.
Weiler et al., "Anti-miRNA oligonucleotides (AMOs): ammunition to target miRNAs implicated in human disease?," Gene Therapy, 2006, vol. 13, p. 496-502.
Written Opinion of the International Searching Authority dated Jul. 15, 2016, for PCT Application No. PCT/US2016/014108, filed on Jan. 20, 2016, 6 pages.
Wu et al., "Argonaute 2 promotes myeloma angiogenesis via microRNA dysregulation," J. Hematol. Oncol. 7:40, 14 pages (2014).
Xu et al., "The *Drosophila* MicroRNA Mir-14 Suppresses Cell Death and Is Required for Normal Fat Metabolism," Curr. Biol. 13:790-795 (2003).
Zhang et al., "MicroRNA-92a Functions as an Oncogene in Colorectal Cancer by Targeting PTEN," Dig. Dis. Sci. 59:98-107 (2014).
U.S. Appl. No. 15/703,753, filed Sep. 13, 2017, by van Rooij et al.

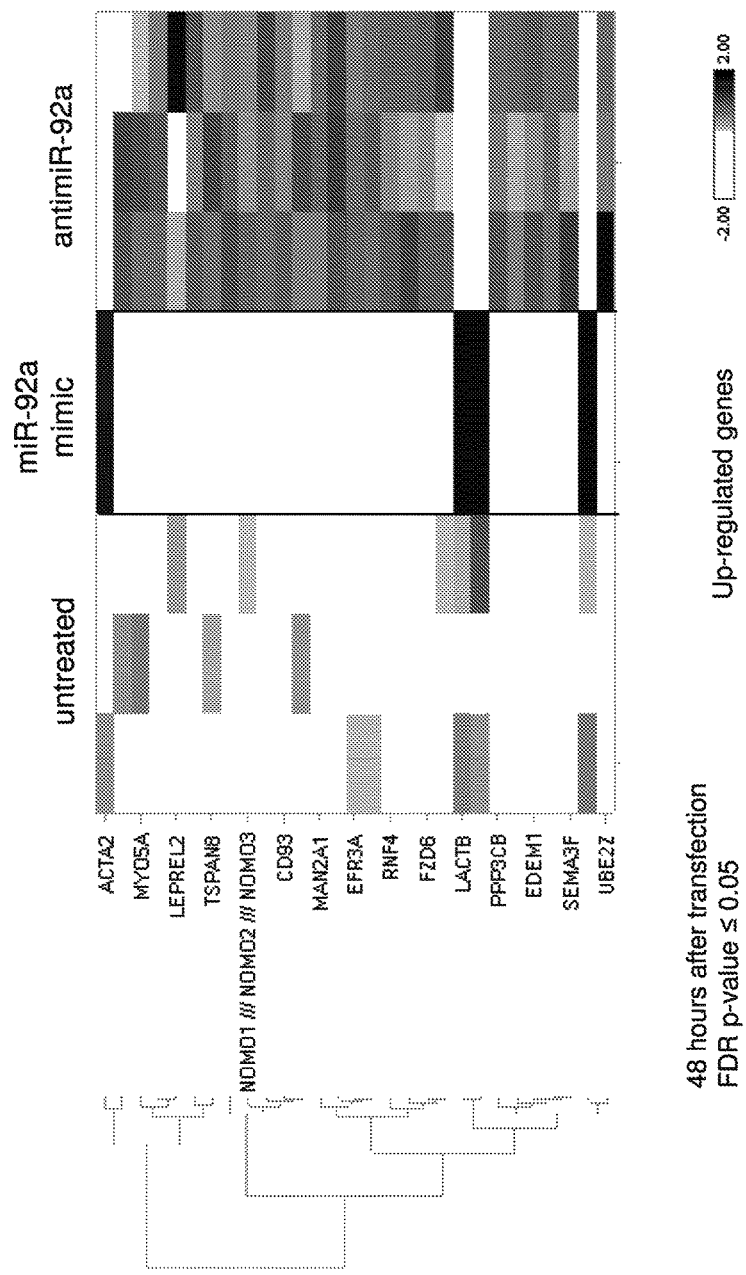

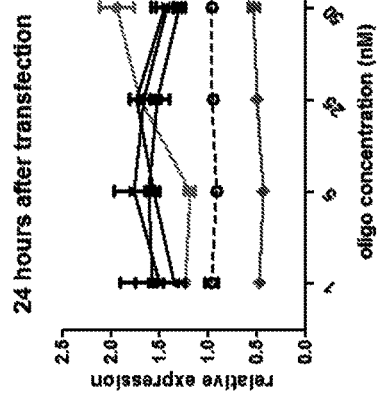
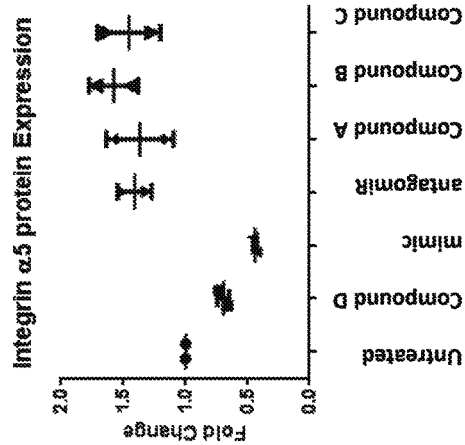
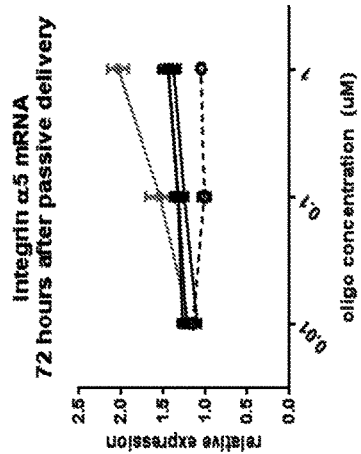

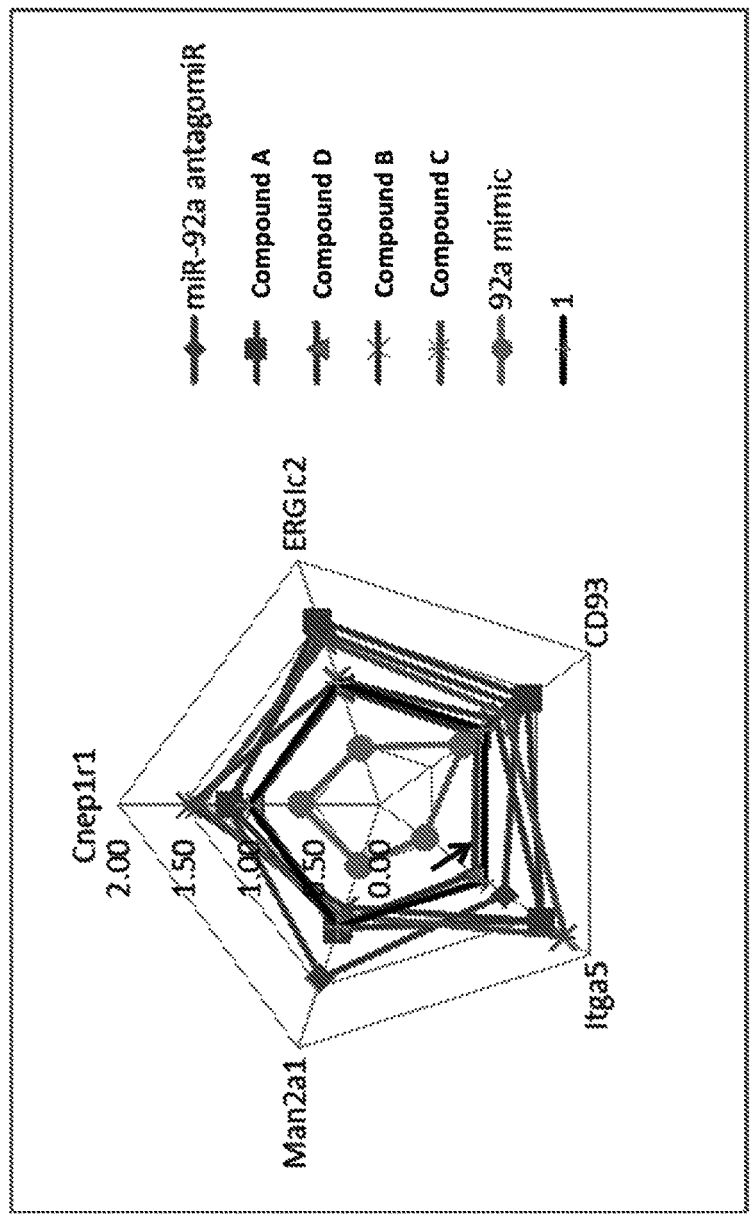

† = p<0.05, Kruskal-Wallis
** = p<0.01, One-way ANOVA
○ = p=0.0552, T test
‡ = p<0.01, T test

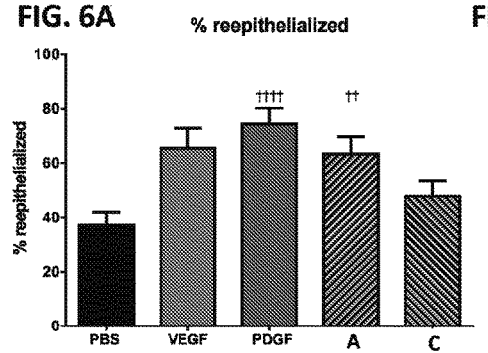
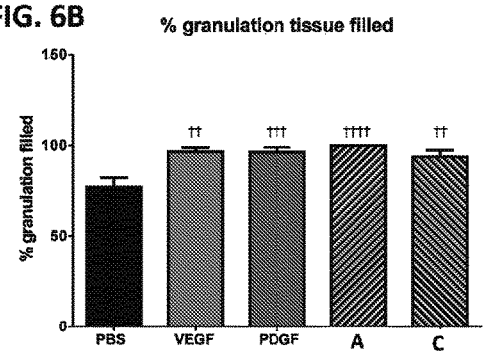
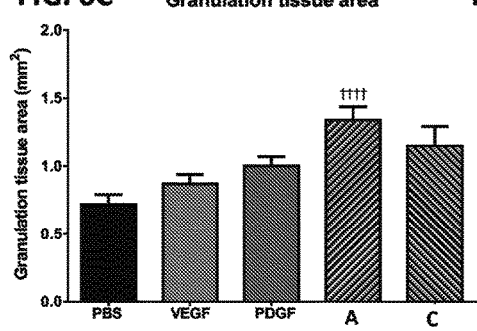
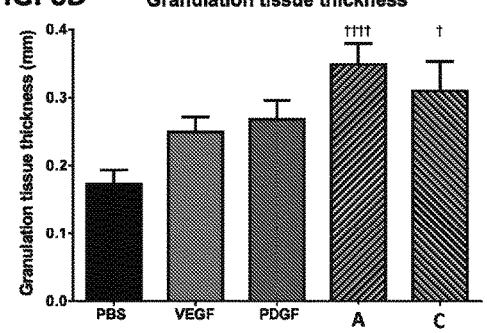
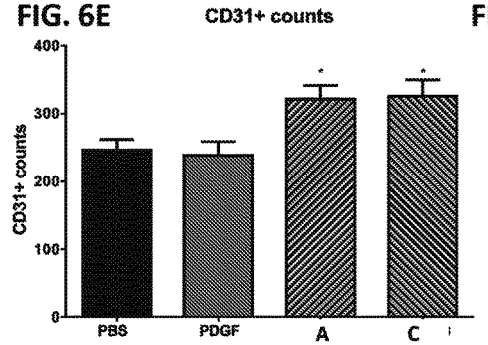
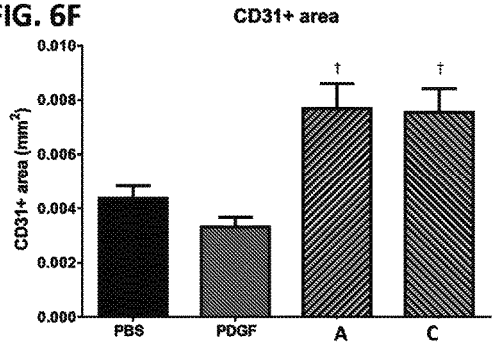
† = p<0.05, Kruskal-Wallis
†† = p<0.01, Kruskal-Wallis
††† = p<0.001, Kruskal-Wallis
†††† = p<0.0001, Kruskal-Wallis
* = p<0.05, One-way ANOVA

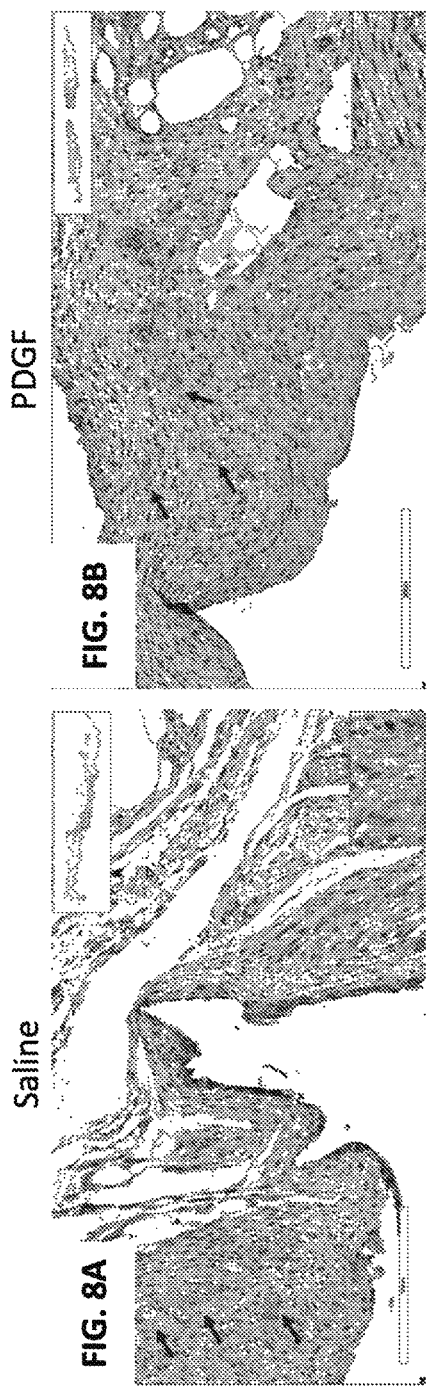
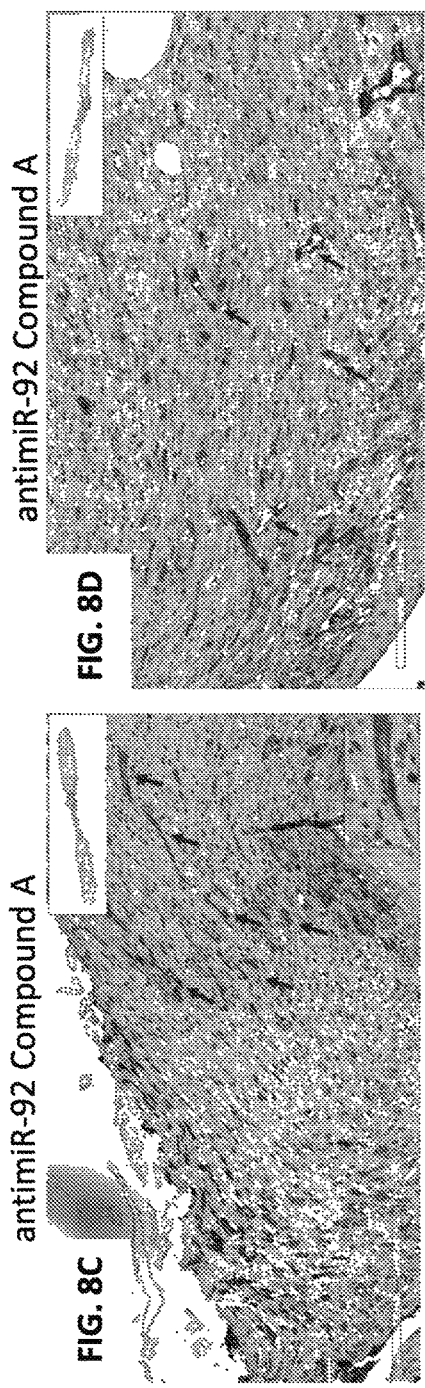
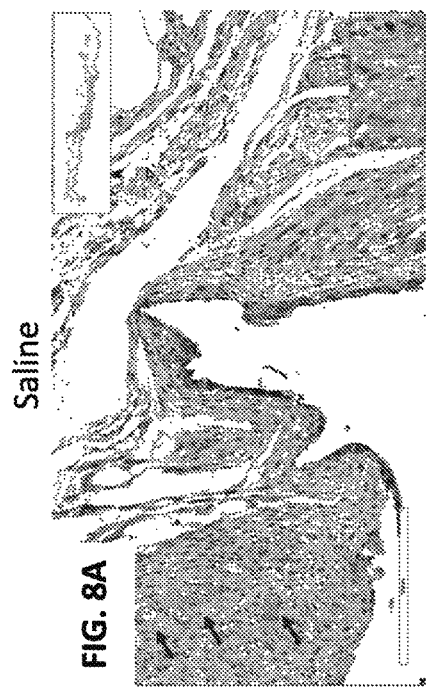
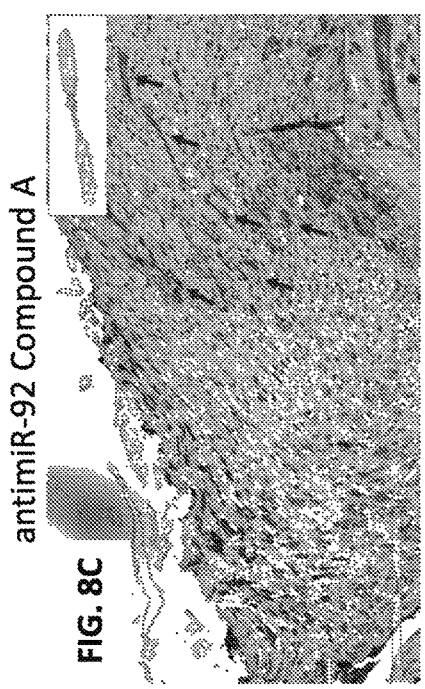

US 10,280,422 B2

SEQUENCE LISTING

```
<160> NUMBER OF SEQ ID NOS: 164

<210> SEQ ID NO 1
<211> LENGTH: 22
<212> TYPE: RNA
<213> ORGANISM: Homo sapiens

<400> SEQUENCE: 1
uauugcacuu gucccggccu gu                                              22

<210> SEQ ID NO 2
<211> LENGTH: 23
<212> TYPE: RNA
<213> ORGANISM: Homo sapiens

<400> SEQUENCE: 2
agguugggau cgguugcaau gcu                                             23

<210> SEQ ID NO 3
<211> LENGTH: 22
<212> TYPE: RNA
<213> ORGANISM: Homo sapiens

<400> SEQUENCE: 3 gggugggau uuguugcauu ac                                               22

<210> SEQ ID NO 4
<211> LENGTH: 21
<212> TYPE: RNA
<213> ORGANISM: Unknown
<220> FEATURE:
<223> OTHER INFORMATION: May be from Mus sp. or Rattus sp.

<400> SEQUENCE: 4
uauugcacuu gucccggccu g                                               21

<210> SEQ ID NO 5
<211> LENGTH: 23
<212> TYPE: RNA
<213> ORGANISM: Unknown
<220> FEATURE:
```

```
<223> OTHER INFORMATION: May be from Mus sp. or Rattus sp.

<400> SEQUENCE: 5
agguugggau uugucgcaau gcu                                        23

<210> SEQ ID NO 6
<211> LENGTH: 22
<212> TYPE: RNA
<213> ORGANISM: Unknown
<220> FEATURE:
<223> OTHER INFORMATION: May be from Mus sp. or Rattus sp.

<400> SEQUENCE: 6
agguggggau uagugccauu ac                                         22

<210> SEQ ID NO 7
<211> LENGTH: 16
<212> TYPE: DNA
<213> ORGANISM: Artificial Sequence
<220> FEATURE:
<223> OTHER INFORMATION: 92a LNA 16 PS
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 7
ccgggacaag tgcaat                                                16

<210> SEQ ID NO 8
<211> LENGTH: 16
<212> TYPE: DNA
<213> ORGANISM: Artificial Sequence
<220> FEATURE:
<223> OTHER INFORMATION: 92a LNA 16 1
<220> FEATURE:
<221> NAME/KEY: MISC_FEATURE
```

<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (15)..(15)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 8
ccgggacaag tgcaat                                                     16

<210> SEQ ID NO 9
<211> LENGTH: 16
<212> TYPE: DNA
<213> ORGANISM: Artificial Sequence
<220> FEATURE:
<223> OTHER INFORMATION: 92a LNA 16 4
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:

```
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 9
ccgggacaag tgcaat                                                         16

<210> SEQ ID NO 10
<211> LENGTH: 8
<212> TYPE: DNA
<213> ORGANISM: Artificial Sequence
<220> FEATURE:
<223> OTHER INFORMATION: 92a Tiny LNA
<220> FEATURE:
<221> NAME/KEY: MISC_FEATURE
<222> LOCATION: (1)..(8)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid adenosine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid thymidine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid cytidine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid thymidine

<400> SEQUENCE: 10 agtgcaat                                                                  8

<210> SEQ ID NO 11
<211> LENGTH: 16
<212> TYPE: DNA
<213> ORGANISM: Artificial Sequence
<220> FEATURE:
<223> OTHER INFORMATION: 92a LNA 16 2
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
```

```
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (7)..(7)
<223> OTHER INFORMATION: May be locked nucleic acid cytidine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid guanosine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 11
ccgggacaag tgcaat                                                     16

<210> SEQ ID NO 12
<211> LENGTH: 16
<212> TYPE: DNA
<213> ORGANISM: Artificial Sequence
<220> FEATURE:
<223> OTHER INFORMATION: 92a LNA 16 3
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (7)..(7)
<223> OTHER INFORMATION: May be locked nucleic acid cytidine
<220> FEATURE:
<221> NAME/KEY: MOD_RES
<222> LOCATION: (9)..(9)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid guanosine
<220> FEATURE:
<221> NAME/KEY: MOD_RES
<222> LOCATION: (14)..(14)
```

<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 12
ccgggacaag tgcaat                                                         16

<210> SEQ ID NO 13
<211> LENGTH: 16
<212> TYPE: DNA
<213> ORGANISM: Artificial Sequence
<220> FEATURE:
<223> OTHER INFORMATION: 92a LNA 16 5
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (7)..(7)
<223> OTHER INFORMATION: May be locked nucleic acid cytidine
<220> FEATURE:
<221> NAME/KEY: MOD_RES
<222> LOCATION: (9)..(9)
<223> OTHER INFORMATION: May be locked nucleic acid adenosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (15)..(15)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 13
ccgggacaag tgcaat                                                         16

<210> SEQ ID NO 14
<211> LENGTH: 16
<212> TYPE: DNA
<213> ORGANISM: Artificial Sequence
<220> FEATURE:
<223> OTHER INFORMATION: 92a LNA 16 6
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES

```
<222> LOCATION: (2)..(2)
<223> OTHER INFORMATION: May be locked nucleic acid cytidine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid guanosine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 14
ccgggacaag tgcaat                                                        16

<210> SEQ ID NO 15
<211> LENGTH: 16
<212> TYPE: DNA
<213> ORGANISM: Artificial Sequence
<220> FEATURE:
<223> OTHER INFORMATION: 92a LNA 16 7
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (12)..(12)
<223> OTHER INFORMATION: May be locked nucleic acid guanosine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid adenosine
<220> FEATURE:
```

```
<221> NAME/KEY: MOD_RES
<222> LOCATION: (16)..(16)
<223> OTHER INFORMATION: May be locked nucleic acid thymidine

<400> SEQUENCE: 15
ccgggacaag tgcaat                                                         16

<210> SEQ ID NO 16
<211> LENGTH: 16
<212> TYPE: DNA
<213> ORGANISM: Artificial Sequence
<220> FEATURE:
<223> OTHER INFORMATION: 92a LNA 16 8
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 16
ccgggacaag tgcaat                                                         16

<210> SEQ ID NO 17
<211> LENGTH: 16
<212> TYPE: DNA
<213> ORGANISM: Artificial Sequence
<220> FEATURE:
<223> OTHER INFORMATION: 92a LNA 16 9
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
```

```
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid guanosine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 17
ccgggacaag tgcaat                                                   16

<210> SEQ ID NO 18
<211> LENGTH: 16
<212> TYPE: DNA
<213> ORGANISM: Artificial Sequence
<220> FEATURE:
<223> OTHER INFORMATION: 92a LNA 16 10
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid adenosine
<220> FEATURE:
<221> NAME/KEY: MOD_RES
<222> LOCATION: (16)..(16)
```

<223> OTHER INFORMATION: May be locked nucleic acid thymidine

<400> SEQUENCE: 18
ccgggacaag tgcaat                                                                16

<210> SEQ ID NO 19
<211> LENGTH: 16
<212> TYPE: DNA
<213> ORGANISM: Artificial Sequence
<220> FEATURE:
<223> OTHER INFORMATION: 92a LNA 16 11
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 19
ccgggacaag tgcaat                                                                16

<210> SEQ ID NO 20
<211> LENGTH: 16
<212> TYPE: DNA
<213> ORGANISM: Artificial Sequence
<220> FEATURE:
<223> OTHER INFORMATION: 92a LNA 16 12
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be locked nucleic acid cytidine
<220> FEATURE:
<221> NAME/KEY: MOD_RES

```
<222> LOCATION: (3)..(3)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 20
ccgggacaag tgcaat                                                    16

<210> SEQ ID NO 21
<211> LENGTH: 16
<212> TYPE: DNA
<213> ORGANISM: Artificial Sequence
<220> FEATURE:
<223> OTHER INFORMATION: 92a LNA 16 13
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine
```

<400> SEQUENCE: 21
ccgggacaag tgcaat                                                        16

<210> SEQ ID NO 22
<211> LENGTH: 16
<212> TYPE: DNA
<213> ORGANISM: Artificial Sequence
<220> FEATURE:
<223> OTHER INFORMATION: 92a LNA 16 14
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (7)..(7)
<223> OTHER INFORMATION: May be locked nucleic acid cytidine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (15)..(15)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 22
ccgggacaag tgcaat                                                        16

<210> SEQ ID NO 23
<211> LENGTH: 16
<212> TYPE: DNA
<213> ORGANISM: Artificial Sequence
<220> FEATURE:
<223> OTHER INFORMATION: 92a LNA 16 15
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be locked nucleic acid cytidine
<220> FEATURE:
<221> NAME/KEY: MOD_RES
<222> LOCATION: (5)..(5)
<223> OTHER INFORMATION: May be locked nucleic acid guanosine

```
<220> FEATURE:
<221> NAME/KEY: MOD_RES
<222> LOCATION: (7)..(7)
<223> OTHER INFORMATION: May be locked nucleic acid cytidine
<220> FEATURE:
<221> NAME/KEY: MOD_RES
<222> LOCATION: (9)..(9)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid guanosine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (16)..(16)
<223> OTHER INFORMATION: May be locked nucleic acid thymidine

<400> SEQUENCE: 23
ccgggacaag tgcaat                                                    16

<210> SEQ ID NO 24
<211> LENGTH: 16
<212> TYPE: DNA
<213> ORGANISM: Artificial Sequence
<220> FEATURE:
<223> OTHER INFORMATION: 92a LNA 16 16
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid adenosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 24
```

```
ccgggacaag tgcaat                                                            16
```

```
<210> SEQ ID NO 25
<211> LENGTH: 16
<212> TYPE: DNA
<213> ORGANISM: Artificial Sequence
<220> FEATURE:
<223> OTHER INFORMATION: 92a LNA 16 17
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid guanosine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 25
ccgggacaag tgcaat                                                            16

<210> SEQ ID NO 26
<211> LENGTH: 16
<212> TYPE: DNA
<213> ORGANISM: Artificial Sequence
<220> FEATURE:
<223> OTHER INFORMATION: 92a LNA 16 18
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
```

```
<222> LOCATION: (7)..(7)
<223> OTHER INFORMATION: May be locked nucleic acid cytidine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 26
ccgggacaag tgcaat                                                 16

<210> SEQ ID NO 27
<211> LENGTH: 16
<212> TYPE: DNA
<213> ORGANISM: Artificial Sequence
<220> FEATURE:
<223> OTHER INFORMATION: 92a LNA 16 19
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 27
ccgggacaag tgcaat                                                 16
```

```
<210> SEQ ID NO 28
<211> LENGTH: 16
<212> TYPE: DNA
<213> ORGANISM: Artificial Sequence
<220> FEATURE:
<223> OTHER INFORMATION: 92a LNA 16 20
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 28
ccgggacaag tgcaat                                                 16

<210> SEQ ID NO 29
<211> LENGTH: 16
<212> TYPE: DNA
<213> ORGANISM: Artificial Sequence
<220> FEATURE:
<223> OTHER INFORMATION: 92a LNA 16 21
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be locked nucleic acid cytidine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (7)..(7)
<223> OTHER INFORMATION: May be locked nucleic acid cytidine
```

```
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (15)..(15)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 29
ccgggacaag tgcaat                                                 16

<210> SEQ ID NO 30
<211> LENGTH: 16
<212> TYPE: DNA
<213> ORGANISM: Artificial Sequence
<220> FEATURE:
<223> OTHER INFORMATION: 92a LNA 16 22
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (7)..(7)
<223> OTHER INFORMATION: May be locked nucleic acid cytidine
<220> FEATURE:
<221> NAME/KEY: MOD_RES
<222> LOCATION: (9)..(9)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid guanosine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 30
ccgggacaag tgcaat                                                 16

<210> SEQ ID NO 31
```

```
<211> LENGTH: 16
<212> TYPE: DNA
<213> ORGANISM: Artificial Sequence
<220> FEATURE:
<223> OTHER INFORMATION: 92a LNA 16 23
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid cytidine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (15)..(15)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 31
ccgggacaag tgcaat                                                     16

<210> SEQ ID NO 32
<211> LENGTH: 16
<212> TYPE: DNA
<213> ORGANISM: Artificial Sequence
<220> FEATURE:
<223> OTHER INFORMATION: 92a LNA 16 24
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (7)..(7)
<223> OTHER INFORMATION: May be locked nucleic acid cytidine
<220> FEATURE:
<221> NAME/KEY: MOD_RES
```

```
<222> LOCATION: (10)..(10)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid guanosine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 32
ccgggacaag tgcaat                                              16

<210> SEQ ID NO 33
<211> LENGTH: 16
<212> TYPE: DNA
<213> ORGANISM: Artificial Sequence
<220> FEATURE:
<223> OTHER INFORMATION: 92a LNA 16 25
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (7)..(7)
<223> OTHER INFORMATION: May be locked nucleic acid cytidine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid guanosine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 33
ccgggacaag tgcaat                                              16

<210> SEQ ID NO 34
<211> LENGTH: 15
<212> TYPE: DNA
```

```
<213> ORGANISM: Artificial Sequence
<220> FEATURE:
<223> OTHER INFORMATION: 92a LNA 15 1
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid thymidine
<220> FEATURE:
<221> NAME/KEY: MOD_RES
<222> LOCATION: (12)..(12)
<223> OTHER INFORMATION: May be locked nucleic acid cytidine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 34
cgggacaagt gcaat                                                      15

<210> SEQ ID NO 35
<211> LENGTH: 15
<212> TYPE: DNA
<213> ORGANISM: Artificial Sequence
<220> FEATURE:
<223> OTHER INFORMATION: 92a LNA 15 2
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid thymidine
<220> FEATURE:
<221> NAME/KEY: MOD_RES
<222> LOCATION: (12)..(12)
<223> OTHER INFORMATION: May be locked nucleic acid cytidine
```

```
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 35
cgggacaagt gcaat                                                            15

<210> SEQ ID NO 36
<211> LENGTH: 15
<212> TYPE: DNA
<213> ORGANISM: Artificial Sequence
<220> FEATURE:
<223> OTHER INFORMATION: 92a LNA 15 3
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid cytidine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid guanosine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 36
cgggacaagt gcaat                                                            15

<210> SEQ ID NO 37
<211> LENGTH: 15
<212> TYPE: DNA
<213> ORGANISM: Artificial Sequence
<220> FEATURE:
<223> OTHER INFORMATION: 92a LNA 15 4
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (6)..(6)
```

```
<223> OTHER INFORMATION: May be locked nucleic acid cytidine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid guanosine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 37
cgggacaagt gcaat                                                15

<210> SEQ ID NO 38
<211> LENGTH: 15
<212> TYPE: DNA
<213> ORGANISM: Artificial Sequence
<220> FEATURE:
<223> OTHER INFORMATION: 92a LNA 15 5
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid thymidine
<220> FEATURE:
<221> NAME/KEY: MOD_RES
<222> LOCATION: (12)..(12)
<223> OTHER INFORMATION: May be locked nucleic acid cytidine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 38
cgggacaagt gcaat                                                15

<210> SEQ ID NO 39
<211> LENGTH: 15
<212> TYPE: DNA
<213> ORGANISM: Artificial Sequence
```

```
<220> FEATURE:
<223> OTHER INFORMATION: 92a LNA 15 6
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid cytidine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid thymidine
<220> FEATURE:
<221> NAME/KEY: MOD_RES
<222> LOCATION: (12)..(12)
<223> OTHER INFORMATION: May be locked nucleic acid cytidine
<220> FEATURE:
<221> NAME/KEY: MOD_RES
<222> LOCATION: (15)..(15)
<223> OTHER INFORMATION: May be locked nucleic acid thymidine

<400> SEQUENCE: 39
cgggacaagt gcaat                                                   15

<210> SEQ ID NO 40
<211> LENGTH: 15
<212> TYPE: DNA
<213> ORGANISM: Artificial Sequence
<220> FEATURE:
<223> OTHER INFORMATION: 92a LNA 15 7
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid guanosine
<220> FEATURE:
```

```
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 40
cgggacaagt gcaat                                                        15

<210> SEQ ID NO 41
<211> LENGTH: 15
<212> TYPE: DNA
<213> ORGANISM: Artificial Sequence
<220> FEATURE:
<223> OTHER INFORMATION: 92a LNA 15 8
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (11)..(11)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid cytidine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 41
cgggacaagt gcaat                                                        15

<210> SEQ ID NO 42
<211> LENGTH: 15
<212> TYPE: DNA
<213> ORGANISM: Artificial Sequence
<220> FEATURE:
<223> OTHER INFORMATION: 92a LNA 15 9
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be locked nucleic acid guanosine
```

```
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 42
cgggacaagt gcaat                                                    15

<210> SEQ ID NO 43
<211> LENGTH: 15
<212> TYPE: DNA
<213> ORGANISM: Artificial Sequence
<220> FEATURE:
<223> OTHER INFORMATION: 92a LNA 15 10
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 43
cgggacaagt gcaat                                                    15

<210> SEQ ID NO 44
```

```
<211> LENGTH: 15
<212> TYPE: DNA
<213> ORGANISM: Artificial Sequence
<220> FEATURE:
<223> OTHER INFORMATION: 92a LNA 15 11
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 44
cgggacaagt gcaat                                                    15

<210> SEQ ID NO 45
<211> LENGTH: 15
<212> TYPE: DNA
<213> ORGANISM: Artificial Sequence
<220> FEATURE:
<223> OTHER INFORMATION: 92a LNA 15 12
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid thymidine
<220> FEATURE:
<221> NAME/KEY: MOD_RES
```

```
<222> LOCATION: (12)..(12)
<223> OTHER INFORMATION: May be locked nucleic acid cytidine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 45
cgggacaagt gcaat                                                      15

<210> SEQ ID NO 46
<211> LENGTH: 15
<212> TYPE: DNA
<213> ORGANISM: Artificial Sequence
<220> FEATURE:
<223> OTHER INFORMATION: 92a LNA 15 13
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid cytidine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 46
cgggacaagt gcaat                                                      15

<210> SEQ ID NO 47
<211> LENGTH: 15
<212> TYPE: DNA
<213> ORGANISM: Artificial Sequence
<220> FEATURE:
<223> OTHER INFORMATION: 92a LNA 15 14
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
```

```
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid cytidine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid cytidine
<220> FEATURE:
<221> NAME/KEY: MOD_RES
<222> LOCATION: (15)..(15)
<223> OTHER INFORMATION: May be locked nucleic acid thymidine

<400> SEQUENCE: 47
cgggacaagt gcaat                                                    15

<210> SEQ ID NO 48
<211> LENGTH: 15
<212> TYPE: DNA
<213> ORGANISM: Artificial Sequence
<220> FEATURE:
<223> OTHER INFORMATION: 92a LNA 15 15
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid thymidine
<220> FEATURE:
<221> NAME/KEY: MOD_RES
<222> LOCATION: (12)..(12)
<223> OTHER INFORMATION: May be locked nucleic acid cytidine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 48
cgggacaagt gcaat                                                    15
```

<210> SEQ ID NO 49
<211> LENGTH: 15
<212> TYPE: DNA
<213> ORGANISM: Artificial Sequence
<220> FEATURE:
<223> OTHER INFORMATION: 92a LNA 15 16
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid guanosine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 49
cgggacaagt gcaat                                                    15

<210> SEQ ID NO 50
<211> LENGTH: 15
<212> TYPE: DNA
<213> ORGANISM: Artificial Sequence
<220> FEATURE:
<223> OTHER INFORMATION: 92a LNA 15 17
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid cytidine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (10)..(10)

```
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 50
cgggacaagt gcaat                                                          15

<210> SEQ ID NO 51
<211> LENGTH: 15
<212> TYPE: DNA
<213> ORGANISM: Artificial Sequence
<220> FEATURE:
<223> OTHER INFORMATION: 92a LNA 15 18
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid thymidine
<220> FEATURE:
<221> NAME/KEY: MOD_RES
<222> LOCATION: (12)..(12)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 51
cgggacaagt gcaat                                                          15

<210> SEQ ID NO 52
<211> LENGTH: 15
<212> TYPE: DNA
<213> ORGANISM: Artificial Sequence
<220> FEATURE:
<223> OTHER INFORMATION: 92a LNA 15 19
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
```

```
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid cytidine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 52
cgggacaagt gcaat                                                  15

<210> SEQ ID NO 53
<211> LENGTH: 15
<212> TYPE: DNA
<213> ORGANISM: Artificial Sequence
<220> FEATURE:
<223> OTHER INFORMATION: 92a LNA 15 20
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid cytidine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine
```

-continued

<400> SEQUENCE: 53
cgggacaagt gcaat                                                                15

<210> SEQ ID NO 54
<211> LENGTH: 15
<212> TYPE: DNA
<213> ORGANISM: Artificial Sequence
<220> FEATURE:
<223> OTHER INFORMATION: 92a LNA 15 21
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid cytidine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid guanosine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 54
cgggacaagt gcaat                                                                15

<210> SEQ ID NO 55
<211> LENGTH: 15
<212> TYPE: DNA
<213> ORGANISM: Artificial Sequence
<220> FEATURE:
<223> OTHER INFORMATION: 92a LNA 15 22
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid cytidine

```
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 55
cgggacaagt gcaat                                                          15

<210> SEQ ID NO 56
<211> LENGTH: 15
<212> TYPE: DNA
<213> ORGANISM: Artificial Sequence
<220> FEATURE:
<223> OTHER INFORMATION: 92a LNA 15 23
<220> FEATURE:
<221> NAME/KEY: MISC_FEATURE
<222> LOCATION: (1)..(15)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid cytidine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid cytidine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 56
cgggacaagt gcaat                                                          15

<210> SEQ ID NO 57
<211> LENGTH: 15
<212> TYPE: DNA
<213> ORGANISM: Artificial Sequence
<220> FEATURE:
<223> OTHER INFORMATION: 92a LNA 15 24
<220> FEATURE:
<221> NAME/KEY: MISC_FEATURE
<222> LOCATION: (1)..(15)
```

```
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid cytidine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid guanosine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (15)..(15)
<223> OTHER INFORMATION: May be locked nucleic acid thymidine

<400> SEQUENCE: 57
cgggacaagt gcaat                                                      15

<210> SEQ ID NO 58
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
```

```
<222> LOCATION: (13)..(13)
<223> OTHER INFORMATION: May be locked nucleic acid cytidine
<220> FEATURE:
<221> NAME/KEY: MOD_RES
<222> LOCATION: (16)..(16)
<223> OTHER INFORMATION: May be locked nucleic acid thymidine

<400> SEQUENCE: 58
ccgggacaag tgcaat                                                         16

<210> SEQ ID NO 59
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (15)..(15)
<223> OTHER INFORMATION: May be locked nucleic acid adenosine

<400> SEQUENCE: 59
ccgggacaag tgcaat                                                         16

<210> SEQ ID NO 60
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
```

```
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (15)..(15)
<223> OTHER INFORMATION: May be locked nucleic acid adenosine

<400> SEQUENCE: 60
ccgggacaag tgcaat                                                     16

<210> SEQ ID NO 61
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (15)..(15)
<223> OTHER INFORMATION: May be locked nucleic acid adenosine
```

```
<220> FEATURE:
<221> NAME/KEY: MOD_RES
<222> LOCATION: (16)..(16)
<223> OTHER INFORMATION: May be locked nucleic acid thymidine

<400> SEQUENCE: 61
ccgggacaag tgcaat                                                         16

<210> SEQ ID NO 62
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 62
ccgggacaag tgcaat                                                         16

<210> SEQ ID NO 63
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
```

```
<223> OTHER INFORMATION: May be 5-methyl deoxycytidine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (15)..(15)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 63
ccgggacaag tgcaat                                                        16

<210> SEQ ID NO 64
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be 5-methyl deoxycytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
```

```
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 64
ccgggacaag tgcaat                                                    16

<210> SEQ ID NO 65
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be 5-methyl deoxycytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 65
ccgggacaag tgcaat                                                    16

<210> SEQ ID NO 66
<211> LENGTH: 14
<212> TYPE: DNA
<213> ORGANISM: Artificial Sequence
<220> FEATURE:
<223> OTHER INFORMATION: 92a LNA 14 1
<220> FEATURE:
```

<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (9)..(9)
<223> OTHER INFORMATION: May be locked nucleic acid thymidine
<220> FEATURE:
<221> NAME/KEY: MOD_RES
<222> LOCATION: (11)..(11)
<223> OTHER INFORMATION: May be locked nucleic acid cytidine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid thymidine

<400> SEQUENCE: 66
gggacaagtg caat                                                         14

<210> SEQ ID NO 67
<211> LENGTH: 14
<212> TYPE: DNA
<213> ORGANISM: Artificial Sequence
<220> FEATURE:
<223> OTHER INFORMATION: 92a LNA 14 2
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (9)..(9)
<223> OTHER INFORMATION: May be locked nucleic acid thymidine
<220> FEATURE:
<221> NAME/KEY: MOD_RES
<222> LOCATION: (11)..(11)
<223> OTHER INFORMATION: May be locked nucleic acid cytidine
<220> FEATURE:
<221> NAME/KEY: MOD_RES
<222> LOCATION: (13)..(13)
<223> OTHER INFORMATION: May be locked nucleic acid adenosine -continued

```
<220> FEATURE:
<221> NAME/KEY: MOD_RES
<222> LOCATION: (14)..(14)
<223> OTHER INFORMATION: May be locked nucleic acid thymidine

<400> SEQUENCE: 67
gggacaagtg caat                                                        14

<210> SEQ ID NO 68
<211> LENGTH: 14
<212> TYPE: DNA
<213> ORGANISM: Artificial Sequence
<220> FEATURE:
<223> OTHER INFORMATION: 92a LNA 14 3
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid cytidine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid thymidine

<400> SEQUENCE: 68
gggacaagtg caat                                                        14

<210> SEQ ID NO 69
<211> LENGTH: 14
<212> TYPE: DNA
<213> ORGANISM: Artificial Sequence
<220> FEATURE:
<223> OTHER INFORMATION: 92a LNA 14 4
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (5)..(5)
```

<223> OTHER INFORMATION: May be locked nucleic acid cytidine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid thymidine

<400> SEQUENCE: 69
gggacaagtg caat                                                           14

<210> SEQ ID NO 70
<211> LENGTH: 14
<212> TYPE: DNA
<213> ORGANISM: Artificial Sequence
<220> FEATURE:
<223> OTHER INFORMATION: 92a LNA 14 5
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (9)..(9)
<223> OTHER INFORMATION: May be locked nucleic acid thymidine
<220> FEATURE:
<221> NAME/KEY: MOD_RES
<222> LOCATION: (11)..(11)
<223> OTHER INFORMATION: May be locked nucleic acid cytidine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid thymidine

<400> SEQUENCE: 70
gggacaagtg caat                                                           14

<210> SEQ ID NO 71
<211> LENGTH: 14
<212> TYPE: DNA
<213> ORGANISM: Artificial Sequence

```
<220> FEATURE:
<223> OTHER INFORMATION: 92a LNA 14 6
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid cytidine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid thymidine
<220> FEATURE:
<221> NAME/KEY: MOD_RES
<222> LOCATION: (11)..(11)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid thymidine

<400> SEQUENCE: 71
gggacaagtg caat                                                       14

<210> SEQ ID NO 72
<211> LENGTH: 14
<212> TYPE: DNA
<213> ORGANISM: Artificial Sequence
<220> FEATURE:
<223> OTHER INFORMATION: 92a LNA 14 7
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid adenosine
<220> FEATURE:
```

```
<221> NAME/KEY: MOD_RES
<222> LOCATION: (14)..(14)
<223> OTHER INFORMATION: May be locked nucleic acid thymidine

<400> SEQUENCE: 72
gggacaagtg caat                                                      14

<210> SEQ ID NO 73
<211> LENGTH: 14
<212> TYPE: DNA
<213> ORGANISM: Artificial Sequence
<220> FEATURE:
<223> OTHER INFORMATION: 92a LNA 14 8
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid cytidine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid thymidine

<400> SEQUENCE: 73
gggacaagtg caat                                                      14

<210> SEQ ID NO 74
<211> LENGTH: 14
<212> TYPE: DNA
<213> ORGANISM: Artificial Sequence
<220> FEATURE:
<223> OTHER INFORMATION: 92a LNA 14 9
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid adenosine
```

<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid thymidine

<400> SEQUENCE: 74
gggacaagtg caat                                                          14

<210> SEQ ID NO 75
<211> LENGTH: 14
<212> TYPE: DNA
<213> ORGANISM: Artificial Sequence
<220> FEATURE:
<223> OTHER INFORMATION: 92a LNA 14 10
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid thymidine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid thymidine

<400> SEQUENCE: 75
gggacaagtg caat                                                          14

<210> SEQ ID NO 76
<211> LENGTH: 14
<212> TYPE: DNA
<213> ORGANISM: Artificial Sequence
<220> FEATURE:
<223> OTHER INFORMATION: 92a LNA 14 11
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)

```
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid thymidine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid thymidine

<400> SEQUENCE: 76
gggacaagtg caat                                                       14

<210> SEQ ID NO 77
<211> LENGTH: 14
<212> TYPE: DNA
<213> ORGANISM: Artificial Sequence
<220> FEATURE:
<223> OTHER INFORMATION: 92a LNA 14 12
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid thymidine
<220> FEATURE:
<221> NAME/KEY: MOD_RES
<222> LOCATION: (11)..(11)
<223> OTHER INFORMATION: May be locked nucleic acid cytidine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid thymidine

<400> SEQUENCE: 77
gggacaagtg caat                                                       14

<210> SEQ ID NO 78
<211> LENGTH: 14
<212> TYPE: DNA
<213> ORGANISM: Artificial Sequence
```

<220> FEATURE:
<223> OTHER INFORMATION: 92a LNA 14 13
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid cytidine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid cytidine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid thymidine

<400> SEQUENCE: 78
gggacaagtg caat                                                        14

<210> SEQ ID NO 79
<211> LENGTH: 14
<212> TYPE: DNA
<213> ORGANISM: Artificial Sequence
<220> FEATURE:
<223> OTHER INFORMATION: 92a LNA 14 14
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid cytidine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid cytidine
<220> FEATURE:

<221> NAME/KEY: MOD_RES
<222> LOCATION: (14)..(14)
<223> OTHER INFORMATION: May be locked nucleic acid thymidine

<400> SEQUENCE: 79
gggacaagtg caat                                                        14

<210> SEQ ID NO 80
<211> LENGTH: 14
<212> TYPE: DNA
<213> ORGANISM: Artificial Sequence
<220> FEATURE:
<223> OTHER INFORMATION: 92a LNA 14 15
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid thymidine
<220> FEATURE:
<221> NAME/KEY: MOD_RES
<222> LOCATION: (11)..(11)
<223> OTHER INFORMATION: May be locked nucleic acid cytidine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid thymidine

<400> SEQUENCE: 80
gggacaagtg caat                                                        14

<210> SEQ ID NO 81
<211> LENGTH: 14
<212> TYPE: DNA
<213> ORGANISM: Artificial Sequence
<220> FEATURE:
<223> OTHER INFORMATION: 92a LNA 14 16
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid guanosine -continued

```
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid thymidine

<400> SEQUENCE: 81
gggacaagtg caat                                                    14

<210> SEQ ID NO 82
<211> LENGTH: 14
<212> TYPE: DNA
<213> ORGANISM: Artificial Sequence
<220> FEATURE:
<223> OTHER INFORMATION: 92a LNA 14 17
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid cytidine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (9)..(9)
<223> OTHER INFORMATION: May be locked nucleic acid thymidine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid thymidine

<400> SEQUENCE: 82
gggacaagtg caat                                                    14

<210> SEQ ID NO 83
<211> LENGTH: 14
<212> TYPE: DNA
<213> ORGANISM: Artificial Sequence
<220> FEATURE:
<223> OTHER INFORMATION: 92a LNA 14 18
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (4)..(4)
```

```
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid thymidine
<220> FEATURE:
<221> NAME/KEY: MOD_RES
<222> LOCATION: (11)..(11)
<223> OTHER INFORMATION: May be locked nucleic acid cytidine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid thymidine

<400> SEQUENCE: 83
gggacaagtg caat                                                       14

<210> SEQ ID NO 84
<211> LENGTH: 14
<212> TYPE: DNA
<213> ORGANISM: Artificial Sequence
<220> FEATURE:
<223> OTHER INFORMATION: 92a LNA 14 19
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid cytidine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid thymidine

<400> SEQUENCE: 84
gggacaagtg caat                                                       14

<210> SEQ ID NO 85
<211> LENGTH: 14
<212> TYPE: DNA
<213> ORGANISM: Artificial Sequence
<220> FEATURE:
<223> OTHER INFORMATION: 92a LNA 14 20
<220> FEATURE:
<221> NAME/KEY: MISC_FEATURE
```

```
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid cytidine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid cytidine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid thymidine

<400> SEQUENCE: 85
gggacaagtg caat                                                       14

<210> SEQ ID NO 86
<211> LENGTH: 14
<212> TYPE: DNA
<213> ORGANISM: Artificial Sequence
<220> FEATURE:
<223> OTHER INFORMATION: 92a LNA 14 21
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid cytidine
<220> FEATURE:
<221> NAME/KEY: MOD_RES
<222> LOCATION: (7)..(7)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid adenosine
<220> FEATURE:
```

```
<221> NAME/KEY: MOD_RES
<222> LOCATION: (14)..(14)
<223> OTHER INFORMATION: May be locked nucleic acid thymidine

<400> SEQUENCE: 86
gggacaagtg caat                                                         14

<210> SEQ ID NO 87
<211> LENGTH: 14
<212> TYPE: DNA
<213> ORGANISM: Artificial Sequence
<220> FEATURE:
<223> OTHER INFORMATION: 92a LNA 14 22
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (5)..(5)
<223> OTHER INFORMATION: May be locked nucleic acid cytidine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid cytidine
<220> FEATURE:
<221> NAME/KEY: MOD_RES
<222> LOCATION: (13)..(13)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid thymidine

<400> SEQUENCE: 87
gggacaagtg caat                                                         14

<210> SEQ ID NO 88
<211> LENGTH: 14
<212> TYPE: DNA
<213> ORGANISM: Artificial Sequence
<220> FEATURE:
<223> OTHER INFORMATION: 92a LNA 14 23
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid cytidine
```

```
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid cytidine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid thymidine

<400> SEQUENCE: 88
gggacaagtg caat                                                           14

<210> SEQ ID NO 89
<211> LENGTH: 14
<212> TYPE: DNA
<213> ORGANISM: Artificial Sequence
<220> FEATURE:
<223> OTHER INFORMATION: 92a LNA 14 24
<220> FEATURE:
<221> NAME/KEY: MISC_FEATURE
<222> LOCATION: (1)..(14)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid cytidine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (14)..(14)
<223> OTHER INFORMATION: May be locked nucleic acid thymidine

<400> SEQUENCE: 89
gggacaagtg caat                                                           14

<210> SEQ ID NO 90
<211> LENGTH: 13
<212> TYPE: DNA
<213> ORGANISM: Artificial Sequence
<220> FEATURE:
```

```
<223> OTHER INFORMATION: 92a LNA 13 1
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid adenosine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid guanosine
<220> FEATURE:
<221> NAME/KEY: MOD_RES
<222> LOCATION: (8)..(8)
<223> OTHER INFORMATION: May be locked nucleic acid thymidine
<220> FEATURE:
<221> NAME/KEY: MOD_RES
<222> LOCATION: (10)..(10)
<223> OTHER INFORMATION: May be locked nucleic acid cytidine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 90
ggacaagtgc aat                                                          13

<210> SEQ ID NO 91
<211> LENGTH: 13
<212> TYPE: DNA
<213> ORGANISM: Artificial Sequence
<220> FEATURE:
<223> OTHER INFORMATION: 92a LNA 13 2
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid adenosine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid guanosine
<220> FEATURE:
<221> NAME/KEY: MOD_RES
<222> LOCATION: (8)..(8)
<223> OTHER INFORMATION: May be locked nucleic acid thymidine
<220> FEATURE:
<221> NAME/KEY: MOD_RES
<222> LOCATION: (10)..(10)
<223> OTHER INFORMATION: May be locked nucleic acid cytidine
<220> FEATURE:
<221> NAME/KEY: MOD_RES
```

```
<222> LOCATION: (12)..(12)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 91
ggacaagtgc aat                                                              13

<210> SEQ ID NO 92
<211> LENGTH: 13
<212> TYPE: DNA
<213> ORGANISM: Artificial Sequence
<220> FEATURE:
<223> OTHER INFORMATION: 92a LNA 13 3
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid cytidine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid guanosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 92
ggacaagtgc aat                                                              13

<210> SEQ ID NO 93
<211> LENGTH: 13
<212> TYPE: DNA
<213> ORGANISM: Artificial Sequence
<220> FEATURE:
<223> OTHER INFORMATION: 92a LNA 13 4
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid cytidine
<220> FEATURE:
```

```
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid guanosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 93
ggacaagtgc aat                                                          13

<210> SEQ ID NO 94
<211> LENGTH: 13
<212> TYPE: DNA
<213> ORGANISM: Artificial Sequence
<220> FEATURE:
<223> OTHER INFORMATION: 92a LNA 13 5
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid guanosine
<220> FEATURE:
<221> NAME/KEY: MOD_RES
<222> LOCATION: (8)..(8)
<223> OTHER INFORMATION: May be locked nucleic acid thymidine
<220> FEATURE:
<221> NAME/KEY: MOD_RES
<222> LOCATION: (10)..(10)
<223> OTHER INFORMATION: May be locked nucleic acid cytidine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 94
ggacaagtgc aat                                                          13

<210> SEQ ID NO 95
<211> LENGTH: 13
<212> TYPE: DNA
<213> ORGANISM: Artificial Sequence
<220> FEATURE:
<223> OTHER INFORMATION: 92a LNA 13 6
```

```
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid cytidine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid thymidine
<220> FEATURE:
<221> NAME/KEY: MOD_RES
<222> LOCATION: (10)..(10)
<223> OTHER INFORMATION: May be locked nucleic acid cytidine
<220> FEATURE:
<221> NAME/KEY: MOD_RES
<222> LOCATION: (13)..(13)
<223> OTHER INFORMATION: May be locked nucleic acid thymidine

<400> SEQUENCE: 95
ggacaagtgc aat                                                    13

<210> SEQ ID NO 96
<211> LENGTH: 13
<212> TYPE: DNA
<213> ORGANISM: Artificial Sequence
<220> FEATURE:
<223> OTHER INFORMATION: 92a LNA 13 7
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid adenosine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid guanosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 96
```
ggacaagtgc aat                                                              13

<210> SEQ ID NO 97
<211> LENGTH: 13
<212> TYPE: DNA
<213> ORGANISM: Artificial Sequence
<220> FEATURE:
<223> OTHER INFORMATION: 92a LNA 13 8
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid cytidine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 97
ggacaagtgc aat                                                              13

<210> SEQ ID NO 98
<211> LENGTH: 13
<212> TYPE: DNA
<213> ORGANISM: Artificial Sequence
<220> FEATURE:
<223> OTHER INFORMATION: 92a LNA 13 9
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid adenosine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 98
ggacaagtgc aat                                                          13

<210> SEQ ID NO 99
<211> LENGTH: 13
<212> TYPE: DNA
<213> ORGANISM: Artificial Sequence
<220> FEATURE:
<223> OTHER INFORMATION: 92a LNA 13 10
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid adenosine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid thymidine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 99
ggacaagtgc aat                                                          13

<210> SEQ ID NO 100
<211> LENGTH: 13
<212> TYPE: DNA
<213> ORGANISM: Artificial Sequence
<220> FEATURE:
<223> OTHER INFORMATION: 92a LNA 13 11
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid guanosine
<220> FEATURE:

```
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid thymidine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 100
ggacaagtgc aat                                                           13

<210> SEQ ID NO 101
<211> LENGTH: 13
<212> TYPE: DNA
<213> ORGANISM: Artificial Sequence
<220> FEATURE:
<223> OTHER INFORMATION: 92a LNA 13 12
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid adenosine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid thymidine
<220> FEATURE:
<221> NAME/KEY: MOD_RES
<222> LOCATION: (10)..(10)
<223> OTHER INFORMATION: May be locked nucleic acid cytidine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 101
ggacaagtgc aat                                                           13

<210> SEQ ID NO 102
<211> LENGTH: 13
<212> TYPE: DNA
<213> ORGANISM: Artificial Sequence
<220> FEATURE:
<223> OTHER INFORMATION: 92a LNA 13 13
<220> FEATURE:
<221> NAME/KEY: MISC_FEATURE
<222> LOCATION: (1)..(13)
<223> OTHER INFORMATION: May be joined through phosphorothioate bonds
```

```
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid cytidine
<220> FEATURE:
<221> NAME/KEY: MOD_RES
<222> LOCATION: (7)..(7)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid cytidine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 102
ggacaagtgc aat                                                        13

<210> SEQ ID NO 103
<211> LENGTH: 13
<212> TYPE: DNA
<213> ORGANISM: Artificial Sequence
<220> FEATURE:
<223> OTHER INFORMATION: 92a LNA 13 14
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid cytidine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid guanosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid cytidine
<220> FEATURE:
<221> NAME/KEY: MOD_RES
<222> LOCATION: (13)..(13)
<223> OTHER INFORMATION: May be locked nucleic acid thymidine

<400> SEQUENCE: 103
```
ggacaagtgc aat                                                                  13

<210> SEQ ID NO 104
<211> LENGTH: 13
<212> TYPE: DNA
<213> ORGANISM: Artificial Sequence
<220> FEATURE:
<223> OTHER INFORMATION: 92a LNA 13 15
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid thymidine
<220> FEATURE:
<221> NAME/KEY: MOD_RES
<222> LOCATION: (10)..(10)
<223> OTHER INFORMATION: May be locked nucleic acid cytidine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 104
ggacaagtgc aat                                                                  13

<210> SEQ ID NO 105
<211> LENGTH: 13
<212> TYPE: DNA
<213> ORGANISM: Artificial Sequence
<220> FEATURE:
<223> OTHER INFORMATION: 92a LNA 13 16
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid adenosine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid guanosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES

```
<222> LOCATION: (11)..(11)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 105
ggacaagtgc aat                                                          13

<210> SEQ ID NO 106
<211> LENGTH: 13
<212> TYPE: DNA
<213> ORGANISM: Artificial Sequence
<220> FEATURE:
<223> OTHER INFORMATION: 92a LNA 13 17
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid cytidine
<220> FEATURE:
<221> NAME/KEY: MOD_RES
<222> LOCATION: (7)..(7)
<223> OTHER INFORMATION: May be locked nucleic acid guanosine
<220> FEATURE:
<221> NAME/KEY: MOD_RES
<222> LOCATION: (8)..(8)
<223> OTHER INFORMATION: May be locked nucleic acid thymidine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 106
ggacaagtgc aat                                                          13

<210> SEQ ID NO 107
<211> LENGTH: 13
<212> TYPE: DNA
<213> ORGANISM: Artificial Sequence
<220> FEATURE:
<223> OTHER INFORMATION: 92a LNA 13 18
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid adenosine
<220> FEATURE:
<221> NAME/KEY: MOD_RES
<222> LOCATION: (5)..(5)
<223> OTHER INFORMATION: May be locked nucleic acid adenosine
<220> FEATURE:
```

<221> NAME/KEY: MOD_RES
<222> LOCATION: (8)..(8)
<223> OTHER INFORMATION: May be locked nucleic acid thymidine
<220> FEATURE:
<221> NAME/KEY: MOD_RES
<222> LOCATION: (10)..(10)
<223> OTHER INFORMATION: May be locked nucleic acid cytidine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 107
ggacaagtgc aat                                                      13

<210> SEQ ID NO 108
<211> LENGTH: 13
<212> TYPE: DNA
<213> ORGANISM: Artificial Sequence
<220> FEATURE:
<223> OTHER INFORMATION: 92a LNA 13 19
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid cytidine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 108
ggacaagtgc aat                                                      13

<210> SEQ ID NO 109
<211> LENGTH: 13
<212> TYPE: DNA
<213> ORGANISM: Artificial Sequence
<220> FEATURE:
<223> OTHER INFORMATION: 92a LNA 13 20
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine

```
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid cytidine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid cytidine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 109
ggacaagtgc aat                                                        13

<210> SEQ ID NO 110
<211> LENGTH: 13
<212> TYPE: DNA
<213> ORGANISM: Artificial Sequence
<220> FEATURE:
<223> OTHER INFORMATION: 92a LNA 13 21
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid cytidine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid guanosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 110
ggacaagtgc aat                                                        13

<210> SEQ ID NO 111
```

```
<211> LENGTH: 13
<212> TYPE: DNA
<213> ORGANISM: Artificial Sequence
<220> FEATURE:
<223> OTHER INFORMATION: 92a LNA 13 22
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid adenosine
<220> FEATURE:
<221> NAME/KEY: MOD_RES
<222> LOCATION: (4)..(4)
<223> OTHER INFORMATION: May be locked nucleic acid cytidine
<220> FEATURE:
<221> NAME/KEY: MOD_RES
<222> LOCATION: (7)..(7)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid cytidine
<220> FEATURE:
<221> NAME/KEY: MOD_RES
<222> LOCATION: (12)..(12)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 111
ggacaagtgc aat                                                        13

<210> SEQ ID NO 112
<211> LENGTH: 13
<212> TYPE: DNA
<213> ORGANISM: Artificial Sequence
<220> FEATURE:
<223> OTHER INFORMATION: 92a LNA 13 23
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid cytidine
<220> FEATURE:
<221> NAME/KEY: MOD_RES
<222> LOCATION: (7)..(7)
<223> OTHER INFORMATION: May be locked nucleic acid guanosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
```

<222> LOCATION: (10)..(10)
<223> OTHER INFORMATION: May be locked nucleic acid cytidine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 112
ggacaagtgc aat                                                      13

<210> SEQ ID NO 113
<211> LENGTH: 13
<212> TYPE: DNA
<213> ORGANISM: Artificial Sequence
<220> FEATURE:
<223> OTHER INFORMATION: 92a LNA 13 24
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid cytidine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid guanosine
<220> FEATURE:
<221> NAME/KEY: MOD_RES
<222> LOCATION: (9)..(9)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (13)..(13)
<223> OTHER INFORMATION: May be locked nucleic acid thymidine

<400> SEQUENCE: 113
ggacaagtgc aat                                                      13

<210> SEQ ID NO 114
<211> LENGTH: 12
<212> TYPE: DNA
<213> ORGANISM: Artificial Sequence
<220> FEATURE:
<223> OTHER INFORMATION: 92a LNA 12 1
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:

```
<221> NAME/KEY: MOD_RES
<222> LOCATION: (2)..(2)
<223> OTHER INFORMATION: May be locked nucleic acid adenosine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid guanosine
<220> FEATURE:
<221> NAME/KEY: MOD_RES
<222> LOCATION: (7)..(7)
<223> OTHER INFORMATION: May be locked nucleic acid thymidine
<220> FEATURE:
<221> NAME/KEY: MOD_RES
<222> LOCATION: (9)..(9)
<223> OTHER INFORMATION: May be locked nucleic acid cytidine
<220> FEATURE:
<221> NAME/KEY: MOD_RES
<222> LOCATION: (10)..(10)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 114
gacaagtgca at                                                           12

<210> SEQ ID NO 115
<211> LENGTH: 12
<212> TYPE: DNA
<213> ORGANISM: Artificial Sequence
<220> FEATURE:
<223> OTHER INFORMATION: 92a LNA 12 2
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid adenosine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid guanosine
<220> FEATURE:
<221> NAME/KEY: MOD_RES
<222> LOCATION: (7)..(7)
<223> OTHER INFORMATION: May be locked nucleic acid thymidine
<220> FEATURE:
<221> NAME/KEY: MOD_RES
<222> LOCATION: (9)..(9)
<223> OTHER INFORMATION: May be locked nucleic acid cytidine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 115
gacaagtgca at                                                           12
```

<210> SEQ ID NO 116
<211> LENGTH: 12
<212> TYPE: DNA
<213> ORGANISM: Artificial Sequence
<220> FEATURE:
<223> OTHER INFORMATION: 92a LNA 12 3
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid cytidine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid guanosine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 116
gacaagtgca at                                                          12

<210> SEQ ID NO 117
<211> LENGTH: 12
<212> TYPE: DNA
<213> ORGANISM: Artificial Sequence
<220> FEATURE:
<223> OTHER INFORMATION: 92a LNA 12 4
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid cytidine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid guanosine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (10)..(10)

```
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 117
gacaagtgca at                                                            12

<210> SEQ ID NO 118
<211> LENGTH: 12
<212> TYPE: DNA
<213> ORGANISM: Artificial Sequence
<220> FEATURE:
<223> OTHER INFORMATION: 92a LNA 12 5
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid adenosine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid guanosine
<220> FEATURE:
<221> NAME/KEY: MOD_RES
<222> LOCATION: (7)..(7)
<223> OTHER INFORMATION: May be locked nucleic acid thymidine
<220> FEATURE:
<221> NAME/KEY: MOD_RES
<222> LOCATION: (9)..(9)
<223> OTHER INFORMATION: May be locked nucleic acid cytidine
<220> FEATURE:
<221> NAME/KEY: MOD_RES
<222> LOCATION: (10)..(10)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 118
gacaagtgca at                                                            12

<210> SEQ ID NO 119
<211> LENGTH: 12
<212> TYPE: DNA
<213> ORGANISM: Artificial Sequence
<220> FEATURE:
<223> OTHER INFORMATION: 92a LNA 12 6
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid cytidine
<220> FEATURE:
<221> NAME/KEY: MOD_RES
```

<222> LOCATION: (5)..(5)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid thymidine
<220> FEATURE:
<221> NAME/KEY: MOD_RES
<222> LOCATION: (9)..(9)
<223> OTHER INFORMATION: May be locked nucleic acid cytidine
<220> FEATURE:
<221> NAME/KEY: MOD_RES
<222> LOCATION: (12)..(12)
<223> OTHER INFORMATION: May be locked nucleic acid thymidine

<400> SEQUENCE: 119
gacaagtgca at                                                          12

<210> SEQ ID NO 120
<211> LENGTH: 12
<212> TYPE: DNA
<213> ORGANISM: Artificial Sequence
<220> FEATURE:
<223> OTHER INFORMATION: 92a LNA 12 7
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid adenosine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid guanosine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 120
gacaagtgca at                                                          12

<210> SEQ ID NO 121
<211> LENGTH: 12
<212> TYPE: DNA
<213> ORGANISM: Artificial Sequence
<220> FEATURE:
<223> OTHER INFORMATION: 92a LNA 12 8
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:

```
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (9)..(9)
<223> OTHER INFORMATION: May be locked nucleic acid cytidine
<220> FEATURE:
<221> NAME/KEY: MOD_RES
<222> LOCATION: (10)..(10)
<223> OTHER INFORMATION: May be locked nucleic acid adenosine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 121
gacaagtgca at                                                           12

<210> SEQ ID NO 122
<211> LENGTH: 12
<212> TYPE: DNA
<213> ORGANISM: Artificial Sequence
<220> FEATURE:
<223> OTHER INFORMATION: 92a LNA 12 9
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid adenosine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid adenosine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 122
gacaagtgca at                                                           12

<210> SEQ ID NO 123
<211> LENGTH: 12
<212> TYPE: DNA
<213> ORGANISM: Artificial Sequence
<220> FEATURE:
<223> OTHER INFORMATION: 92a LNA 12 10
```

```
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid adenosine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid thymidine
<220> FEATURE:
<221> NAME/KEY: MOD_RES
<222> LOCATION: (10)..(10)
<223> OTHER INFORMATION: May be locked nucleic acid adenosine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 123
gacaagtgca at                                                            12

<210> SEQ ID NO 124
<211> LENGTH: 12
<212> TYPE: DNA
<213> ORGANISM: Artificial Sequence
<220> FEATURE:
<223> OTHER INFORMATION: 92a LNA 12 11
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid thymidine
<220> FEATURE:
<221> NAME/KEY: MOD_RES
<222> LOCATION: (10)..(10)
<223> OTHER INFORMATION: May be locked nucleic acid adenosine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 124
gacaagtgca at                                                            12

<210> SEQ ID NO 125
```

```
<211> LENGTH: 12
<212> TYPE: DNA
<213> ORGANISM: Artificial Sequence
<220> FEATURE:
<223> OTHER INFORMATION: 92a LNA 12 12
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid adenosine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid thymidine
<220> FEATURE:
<221> NAME/KEY: MOD_RES
<222> LOCATION: (9)..(9)
<223> OTHER INFORMATION: May be locked nucleic acid cytidine
<220> FEATURE:
<221> NAME/KEY: MOD_RES
<222> LOCATION: (10)..(10)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 125
gacaagtgca at                                                         12

<210> SEQ ID NO 126
<211> LENGTH: 12
<212> TYPE: DNA
<213> ORGANISM: Artificial Sequence
<220> FEATURE:
<223> OTHER INFORMATION: 92a LNA 12 13
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid cytidine
<220> FEATURE:
<221> NAME/KEY: MOD_RES
<222> LOCATION: (6)..(6)
<223> OTHER INFORMATION: May be locked nucleic acid guanosine
<220> FEATURE:
<221> NAME/KEY: MOD_RES
<222> LOCATION: (9)..(9)
<223> OTHER INFORMATION: May be locked nucleic acid cytidine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 126
```
gacaagtgca at                                                              12

<210> SEQ ID NO 127
<211> LENGTH: 12
<212> TYPE: DNA
<213> ORGANISM: Artificial Sequence
<220> FEATURE:
<223> OTHER INFORMATION: 92a LNA 12 14
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid cytidine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid guanosine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (9)..(9)
<223> OTHER INFORMATION: May be locked nucleic acid cytidine
<220> FEATURE:
<221> NAME/KEY: MOD_RES
<222> LOCATION: (12)..(12)
<223> OTHER INFORMATION: May be locked nucleic acid thymidine

<400> SEQUENCE: 127
gacaagtgca at                                                              12

<210> SEQ ID NO 128
<211> LENGTH: 12
<212> TYPE: DNA
<213> ORGANISM: Artificial Sequence
<220> FEATURE:
<223> OTHER INFORMATION: 92a LNA 12 15
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid adenosine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid thymidine
<220> FEATURE:
<221> NAME/KEY: MOD_RES
<222> LOCATION: (9)..(9)
<223> OTHER INFORMATION: May be locked nucleic acid cytidine
<220> FEATURE:

<221> NAME/KEY: MOD_RES
<222> LOCATION: (10)..(10)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 128
gacaagtgca at                                                            12

<210> SEQ ID NO 129
<211> LENGTH: 12
<212> TYPE: DNA
<213> ORGANISM: Artificial Sequence
<220> FEATURE:
<223> OTHER INFORMATION: 92a LNA 12 16
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid adenosine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid guanosine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 129
gacaagtgca at                                                            12

<210> SEQ ID NO 130
<211> LENGTH: 12
<212> TYPE: DNA
<213> ORGANISM: Artificial Sequence
<220> FEATURE:
<223> OTHER INFORMATION: 92a LNA 12 17
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid cytidine
<220> FEATURE:
<221> NAME/KEY: MOD_RES
<222> LOCATION: (6)..(6)
<223> OTHER INFORMATION: May be locked nucleic acid guanosine

```
<220> FEATURE:
<221> NAME/KEY: MOD_RES
<222> LOCATION: (7)..(7)
<223> OTHER INFORMATION: May be locked nucleic acid thymidine
<220> FEATURE:
<221> NAME/KEY: MOD_RES
<222> LOCATION: (10)..(10)
<223> OTHER INFORMATION: May be locked nucleic acid adenosine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 130
gacaagtgca at                                                             12

<210> SEQ ID NO 131
<211> LENGTH: 12
<212> TYPE: DNA
<213> ORGANISM: Artificial Sequence
<220> FEATURE:
<223> OTHER INFORMATION: 92a LNA 12 18
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid adenosine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (7)..(7)
<223> OTHER INFORMATION: May be locked nucleic acid thymidine
<220> FEATURE:
<221> NAME/KEY: MOD_RES
<222> LOCATION: (9)..(9)
<223> OTHER INFORMATION: May be locked nucleic acid cytidine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 131
gacaagtgca at                                                             12

<210> SEQ ID NO 132
<211> LENGTH: 12
<212> TYPE: DNA
<213> ORGANISM: Artificial Sequence
<220> FEATURE:
<223> OTHER INFORMATION: 92a LNA 12 19
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
```

```
<223> OTHER INFORMATION: May be locked nucleic acid guanosine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid guanosine
<220> FEATURE:
<221> NAME/KEY: MOD_RES
<222> LOCATION: (9)..(9)
<223> OTHER INFORMATION: May be locked nucleic acid cytidine
<220> FEATURE:
<221> NAME/KEY: MOD_RES
<222> LOCATION: (10)..(10)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 132
gacaagtgca at                                                           12

<210> SEQ ID NO 133
<211> LENGTH: 12
<212> TYPE: DNA
<213> ORGANISM: Artificial Sequence
<220> FEATURE:
<223> OTHER INFORMATION: 92a LNA 12 20
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid cytidine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid guanosine
<220> FEATURE:
<221> NAME/KEY: MOD_RES
<222> LOCATION: (9)..(9)
<223> OTHER INFORMATION: May be locked nucleic acid cytidine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 133
gacaagtgca at                                                           12

<210> SEQ ID NO 134
<211> LENGTH: 12
<212> TYPE: DNA
<213> ORGANISM: Artificial Sequence
<220> FEATURE:
<223> OTHER INFORMATION: 92a LNA 12 21
<220> FEATURE:
<221> NAME/KEY: MISC_FEATURE
```

```
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid cytidine
<220> FEATURE:
<221> NAME/KEY: MOD_RES
<222> LOCATION: (5)..(5)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid guanosine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 134
gacaagtgca at                                                          12

<210> SEQ ID NO 135
<211> LENGTH: 12
<212> TYPE: DNA
<213> ORGANISM: Artificial Sequence
<220> FEATURE:
<223> OTHER INFORMATION: 92a LNA 12 22
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (2)..(2)
<223> OTHER INFORMATION: May be locked nucleic acid adenosine
<220> FEATURE:
<221> NAME/KEY: MOD_RES
<222> LOCATION: (3)..(3)
<223> OTHER INFORMATION: May be locked nucleic acid cytidine
<220> FEATURE:
<221> NAME/KEY: MOD_RES
<222> LOCATION: (6)..(6)
<223> OTHER INFORMATION: May be locked nucleic acid guanosine
<220> FEATURE:
<221> NAME/KEY: MOD_RES
<222> LOCATION: (9)..(9)
<223> OTHER INFORMATION: May be locked nucleic acid cytidine
<220> FEATURE:
<221> NAME/KEY: MOD_RES
<222> LOCATION: (11)..(11)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 135
gacaagtgca at                                                          12
```

```
<210> SEQ ID NO 136
<211> LENGTH: 12
<212> TYPE: DNA
<213> ORGANISM: Artificial Sequence
<220> FEATURE:
<223> OTHER INFORMATION: 92a LNA 12 23
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid cytidine
<220> FEATURE:
<221> NAME/KEY: MOD_RES
<222> LOCATION: (6)..(6)
<223> OTHER INFORMATION: May be locked nucleic acid guanosine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (9)..(9)
<223> OTHER INFORMATION: May be locked nucleic acid cytidine
<220> FEATURE:
<221> NAME/KEY: MOD_RES
<222> LOCATION: (10)..(10)
<223> OTHER INFORMATION: May be locked nucleic acid adenosine
<220> FEATURE:
<221> NAME/KEY: MOD_RES
<222> LOCATION: (12)..(12)
<223> OTHER INFORMATION: May be locked nucleic acid thymidine

<400> SEQUENCE: 136
gacaagtgca at                                                         12

<210> SEQ ID NO 137
<211> LENGTH: 12
<212> TYPE: DNA
<213> ORGANISM: Artificial Sequence
<220> FEATURE:
<223> OTHER INFORMATION: 92a LNA 12 24
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid guanosine
<220> FEATURE:
<221> NAME/KEY: MOD_RES
<222> LOCATION: (3)..(3)
<223> OTHER INFORMATION: May be locked nucleic acid cytidine
<220> FEATURE:
<221> NAME/KEY: MOD_RES
<222> LOCATION: (4)..(4)
<223> OTHER INFORMATION: May be locked nucleic acid adenosine
<220> FEATURE:
<221> NAME/KEY: MOD_RES
<222> LOCATION: (6)..(6)
<223> OTHER INFORMATION: May be locked nucleic acid guanosine
<220> FEATURE:
<221> NAME/KEY: MOD_RES
<222> LOCATION: (8)..(8)
<223> OTHER INFORMATION: May be locked nucleic acid guanosine
<220> FEATURE:
<221> NAME/KEY: MOD_RES
<222> LOCATION: (10)..(10)
<223> OTHER INFORMATION: May be locked nucleic acid adenosine
```

```
<220> FEATURE:
<221> NAME/KEY: MOD_RES
<222> LOCATION: (12)..(12)
<223> OTHER INFORMATION: May be locked nucleic acid thymidine

<400> SEQUENCE: 137
gacaagtgca at                                                            12

<210> SEQ ID NO 138
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 138
ccgggacaag tgcaat                                                        16

<210> SEQ ID NO 139
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
```

<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 139
ccgggacaag tgcaat                                                     16

<210> SEQ ID NO 140
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(9)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 140
ccgggacaag tgcaat         16

<210> SEQ ID NO 141
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(2)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MISC_FEATURE
<222> LOCATION: (3)..(4)
<223> OTHER INFORMATION: May be joined through phosphorothioate bonds
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MISC_FEATURE
<222> LOCATION: (5)..(6)
<223> OTHER INFORMATION: May be joined through phosphorothioate bonds
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MISC_FEATURE
<222> LOCATION: (7)..(8)
<223> OTHER INFORMATION: May be joined through phosphorothioate bonds
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MISC_FEATURE
<222> LOCATION: (9)..(10)
<223> OTHER INFORMATION: May be joined through phosphorothioate bonds
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MISC_FEATURE
<222> LOCATION: (11)..(12)
<223> OTHER INFORMATION: May be joined through phosphorothioate bonds
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MISC_FEATURE
<222> LOCATION: (13)..(14)
<223> OTHER INFORMATION: May be joined through phosphorothioate bonds
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MISC_FEATURE
<222> LOCATION: (15)..(16)
<223> OTHER INFORMATION: May be joined through phosphorothioate bonds
<220> FEATURE:

-continued

```
<221> NAME/KEY: MOD_RES
<222> LOCATION: (16)..(16)
<223> OTHER INFORMATION: May be locked nucleic acid thymidine

<400> SEQUENCE: 141
ccgggacaag tgcaat                                                   16

<210> SEQ ID NO 142
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(2)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MISC_FEATURE
<222> LOCATION: (4)..(5)
<223> OTHER INFORMATION: May be joined through phosphorothioate bonds
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MISC_FEATURE
<222> LOCATION: (7)..(8)
<223> OTHER INFORMATION: May be joined through phosphorothioate bonds
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MISC_FEATURE
<222> LOCATION: (10)..(11)
<223> OTHER INFORMATION: May be joined through phosphorothioate bonds
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MISC_FEATURE
<222> LOCATION: (13)..(14)
<223> OTHER INFORMATION: May be joined through phosphorothioate bonds
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 142
ccgggacaag tgcaat                                                   16

<210> SEQ ID NO 143
<211> LENGTH: 16
```

```
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 143
ccgggacaag tgcaat                                                    16

<210> SEQ ID NO 144
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be 5-methyl deoxycytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
```

```
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 144
ccgggacaag tgcaat                                                    16

<210> SEQ ID NO 145
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be 5-methyl deoxycytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 145
ccgggacaag tgcaat                                                    16
```

```
<210> SEQ ID NO 146
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(9)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be 5-methyl deoxycytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 146
ccgggacaag tgcaat                                                     16

<210> SEQ ID NO 147
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(2)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be 5-methyl deoxycytidine
<220> FEATURE:
<221> NAME/KEY: MISC_FEATURE
<222> LOCATION: (3)..(4)
<223> OTHER INFORMATION: May be joined through phosphorothioate bonds
<220> FEATURE:
```

<221> NAME/KEY: MOD_RES
<222> LOCATION: (3)..(3)
<223> OTHER INFORMATION: May be locked nucleic acid guanosine
<220> FEATURE:
<221> NAME/KEY: MISC_FEATURE
<222> LOCATION: (5)..(6)
<223> OTHER INFORMATION: May be joined through phosphorothioate bonds
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MISC_FEATURE
<222> LOCATION: (7)..(8)
<223> OTHER INFORMATION: May be joined through phosphorothioate bonds
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MISC_FEATURE
<222> LOCATION: (9)..(10)
<223> OTHER INFORMATION: May be joined through phosphorothioate bonds
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MISC_FEATURE
<222> LOCATION: (11)..(12)
<223> OTHER INFORMATION: May be joined through phosphorothioate bonds
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MISC_FEATURE
<222> LOCATION: (13)..(14)
<223> OTHER INFORMATION: May be joined through phosphorothioate bonds
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MISC_FEATURE
<222> LOCATION: (15)..(16)
<223> OTHER INFORMATION: May be joined through phosphorothioate bonds
<220> FEATURE:
<221> NAME/KEY: MOD_RES
<222> LOCATION: (16)..(16)
<223> OTHER INFORMATION: May be locked nucleic acid thymidine

<400> SEQUENCE: 147
ccgggacaag tgcaat                                                    16

<210> SEQ ID NO 148
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(2)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be 5-methyl deoxycytidine

```
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MISC_FEATURE
<222> LOCATION: (4)..(5)
<223> OTHER INFORMATION: May be joined through phosphorothioate bonds
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MISC_FEATURE
<222> LOCATION: (7)..(8)
<223> OTHER INFORMATION: May be joined through phosphorothioate bonds
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MISC_FEATURE
<222> LOCATION: (10)..(11)
<223> OTHER INFORMATION: May be joined through phosphorothioate bonds
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MISC_FEATURE
<222> LOCATION: (13)..(14)
<223> OTHER INFORMATION: May be joined through phosphorothioate bonds
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 148
ccgggacaag tgcaat                                                    16

<210> SEQ ID NO 149
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be 5-methyl deoxycytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
```

```
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 149
ccgggacaag tgcaat                                                    16

<210> SEQ ID NO 150
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be 5-methyl deoxycytidine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (15)..(15)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 150
```

-continued ccgggacaag tgcaat                                                  16

<210> SEQ ID NO 151
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be 5-methyl deoxycytidine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (15)..(15)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 151
ccgggacaag tgcaat                                                  16

<210> SEQ ID NO 152
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(8)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be 5-methyl deoxycytidine
<220> FEATURE:

<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (15)..(15)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 152
ccgggacaag tgcaat                                                       16

<210> SEQ ID NO 153
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(2)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be 5-methyl deoxycytidine
<220> FEATURE:
<221> NAME/KEY: MISC_FEATURE
<222> LOCATION: (3)..(4)
<223> OTHER INFORMATION: May be joined through phosphorothioate bonds
<220> FEATURE:
<221> NAME/KEY: MISC_FEATURE
<222> LOCATION: (5)..(6)
<223> OTHER INFORMATION: May be joined through phosphorothioate bonds
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MISC_FEATURE
<222> LOCATION: (7)..(8)
<223> OTHER INFORMATION: May be joined through phosphorothioate bonds
<220> FEATURE:
<221> NAME/KEY: MOD_RES
<222> LOCATION: (8)..(8)
<223> OTHER INFORMATION: May be locked nucleic acid adenosine

```
<220> FEATURE:
<221> NAME/KEY: MISC_FEATURE
<222> LOCATION: (9)..(10)
<223> OTHER INFORMATION: May be joined through phosphorothioate bonds
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MISC_FEATURE
<222> LOCATION: (11)..(12)
<223> OTHER INFORMATION: May be joined through phosphorothioate bonds
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MISC_FEATURE
<222> LOCATION: (13)..(14)
<223> OTHER INFORMATION: May be joined through phosphorothioate bonds
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MISC_FEATURE
<222> LOCATION: (15)..(16)
<223> OTHER INFORMATION: May be joined through phosphorothioate bonds
<220> FEATURE:
<221> NAME/KEY: MOD_RES
<222> LOCATION: (15)..(15)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 153
ccgggacaag tgcaat                                                    16

<210> SEQ ID NO 154
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(2)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be 5-methyl deoxycytidine
<220> FEATURE:
<221> NAME/KEY: MISC_FEATURE
<222> LOCATION: (4)..(5)
<223> OTHER INFORMATION: May be joined through phosphorothioate bonds
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MISC_FEATURE
<222> LOCATION: (7)..(8)
<223> OTHER INFORMATION: May be joined through phosphorothioate bonds
<220> FEATURE:
<221> NAME/KEY: MOD_RES
<222> LOCATION: (8)..(8)
```

```
<223> OTHER INFORMATION: May be locked nucleic acid adenosine
<220> FEATURE:
<221> NAME/KEY: MISC_FEATURE
<222> LOCATION: (10)..(11)
<223> OTHER INFORMATION: May be joined through phosphorothioate bonds
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MISC_FEATURE
<222> LOCATION: (13)..(14)
<223> OTHER INFORMATION: May be joined through phosphorothioate bonds
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (15)..(15)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 154
ccgggacaag tgcaat                                                     16

<210> SEQ ID NO 155
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be 5-methyl deoxycytidine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (15)..(15)
<223> OTHER INFORMATION: May be locked nucleic acid adenosine
<220> FEATURE:
<221> NAME/KEY: MOD_RES
```

```
<222> LOCATION: (16)..(16)
<223> OTHER INFORMATION: May be locked nucleic acid thymidine

<400> SEQUENCE: 155
ccgggacaag tgcaat                                                      16

<210> SEQ ID NO 156
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(13)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be 5-methyl deoxycytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 156
ccgggacaag tgcaat                                                      16

<210> SEQ ID NO 157
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
```

<220> FEATURE:
<221> NAME/KEY: MOD_RES
<222> LOCATION: (2)..(2)
<223> OTHER INFORMATION: May be 5-methyl deoxycytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 157
ccgggacaag tgcaat                                               16

<210> SEQ ID NO 158
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(9)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be 5-methyl deoxycytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine

```
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 158
ccgggacaag tgcaat                                                    16

<210> SEQ ID NO 159
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(2)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be 5-methyl deoxycytidine
<220> FEATURE:
<221> NAME/KEY: MISC_FEATURE
<222> LOCATION: (3)..(4)
<223> OTHER INFORMATION: May be joined through phosphorothioate bonds
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MISC_FEATURE
<222> LOCATION: (5)..(6)
<223> OTHER INFORMATION: May be joined through phosphorothioate bonds
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MISC_FEATURE
<222> LOCATION: (7)..(8)
<223> OTHER INFORMATION: May be joined through phosphorothioate bonds
<220> FEATURE:
<221> NAME/KEY: MISC_FEATURE
<222> LOCATION: (9)..(10)
<223> OTHER INFORMATION: May be joined through phosphorothioate bonds
<220> FEATURE:
<221> NAME/KEY: MOD_RES
<222> LOCATION: (9)..(9)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MISC_FEATURE
<222> LOCATION: (11)..(12)
<223> OTHER INFORMATION: May be joined through phosphorothioate bonds
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MISC_FEATURE
<222> LOCATION: (13)..(14)
```

```
<223> OTHER INFORMATION: May be joined through phosphorothioate bonds
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MISC_FEATURE
<222> LOCATION: (15)..(16)
<223> OTHER INFORMATION: May be joined through phosphorothioate bonds
<220> FEATURE:
<221> NAME/KEY: MOD_RES
<222> LOCATION: (16)..(16)
<223> OTHER INFORMATION: May be locked nucleic acid thymidine

<400> SEQUENCE: 159
ccgggacaag tgcaat                                                      16

<210> SEQ ID NO 160
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(2)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be 5-methyl deoxycytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MISC_FEATURE
<222> LOCATION: (4)..(5)
<223> OTHER INFORMATION: May be joined through phosphorothioate bonds
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MISC_FEATURE
<222> LOCATION: (7)..(8)
<223> OTHER INFORMATION: May be joined through phosphorothioate bonds
<220> FEATURE:
<221> NAME/KEY: MOD_RES
<222> LOCATION: (9)..(9)
<223> OTHER INFORMATION: May be locked nucleic acid adenosine
<220> FEATURE:
<221> NAME/KEY: MISC_FEATURE
<222> LOCATION: (10)..(11)
<223> OTHER INFORMATION: May be joined through phosphorothioate bonds
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MISC_FEATURE
<222> LOCATION: (13)..(14)
<223> OTHER INFORMATION: May be joined through phosphorothioate bonds
<220> FEATURE:
<221> NAME/KEY: MOD_RES
```

<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 160
ccgggacaag tgcaat                                                       16

<210> SEQ ID NO 161
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (2)..(2)
<223> OTHER INFORMATION: May be 5-methyl deoxycytidine
<220> FEATURE:
<221> NAME/KEY: MOD_RES
<222> LOCATION: (3)..(3)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 161
ccgggacaag tgcaat                                                       16

<210> SEQ ID NO 162
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(16)
<223> OTHER INFORMATION: May be joined through phosphorothioate bonds
<220> FEATURE:

```
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (9)..(9)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
<222> LOCATION: (13)..(13)
<223> OTHER INFORMATION: May be locked nucleic acid cytidine
<220> FEATURE:
<221> NAME/KEY: MOD_RES
<222> LOCATION: (15)..(15)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 162
ccgggacaag tgcaat                                                    16

<210> SEQ ID NO 163
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (6)..(6)
<223> OTHER INFORMATION: May be locked nucleic acid adenosine
<220> FEATURE:
<221> NAME/KEY: MOD_RES
<222> LOCATION: (8)..(8)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (11)..(11)
<223> OTHER INFORMATION: May be locked nucleic acid thymidine
<220> FEATURE:
<221> NAME/KEY: MOD_RES
```

```
<222> LOCATION: (13)..(13)
<223> OTHER INFORMATION: May be locked nucleic acid cytidine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 163
ccgggacaag tgcaat                                                      16

<210> SEQ ID NO 164
<211> LENGTH: 16
<212> TYPE: DNA
<213> ORGANISM: Artificial Sequence
<220> FEATURE:
<223> OTHER INFORMATION: MiR-92 Inhibitor
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid cytidine
<220> FEATURE:
<221> NAME/KEY: MOD_RES
<222> LOCATION: (4)..(4)
<223> OTHER INFORMATION: May be locked nucleic acid guanosine
<220> FEATURE:
<221> NAME/KEY: MOD_RES
<222> LOCATION: (5)..(5)
<223> OTHER INFORMATION: May be locked nucleic acid guanosine
<220> FEATURE:
<221> NAME/KEY: MOD_RES
<222> LOCATION: (7)..(7)
<223> OTHER INFORMATION: May be locked nucleic acid cytidine
<220> FEATURE:
<221> NAME/KEY: MOD_RES
<222> LOCATION: (9)..(9)
<223> OTHER INFORMATION: May be locked nucleic acid adenosine
<220> FEATURE:
<221> NAME/KEY: MOD_RES
<222> LOCATION: (10)..(10)
<223> OTHER INFORMATION: May be locked nucleic acid guanosine
<220> FEATURE:
<221> NAME/KEY: MOD_RES
<222> LOCATION: (12)..(12)
<223> OTHER INFORMATION: May be locked nucleic acid guanosine
<220> FEATURE:
<221> NAME/KEY: MOD_RES
<222> LOCATION: (14)..(14)
<223> OTHER INFORMATION: May be locked nucleic acid adenosine
<220> FEATURE:
<221> NAME/KEY: MOD_RES
<222> LOCATION: (16)..(16)
<223> OTHER INFORMATION: May be locked nucleic acid thymidine

<400> SEQUENCE: 164
ccgggacaag tgcaat                                                      16
```

MIR-92 INHIBITORS AND USES THEREOF

RELATED APPLICATION

The present application is a continuation of U.S. patent application Ser. No. 15/001,968, which issued as U.S. Pat. No. 9,885,042 on Feb. 6, 2018, and claims the benefit of U.S. Provisional Application Ser. No. 62/105,546, filed Jan. 20, 2015, which is incorporated by reference in its entirety.

FIELD OF THE INVENTION

The present invention relates generally to modulators of miR-92 function and/or activity, for example, oligonucleotides that are miR-92 inhibitors, and biomarkers for modulators of miR-92 function and/or activity and uses thereof.

BACKGROUND OF THE INVENTION

Diabetes and non-healing diabetic foot ulcers are the leading causes of non-traumatic lower extremity amputation in the US. Diabetic foot ulcers fail to heal due to an insufficient blood supply, ischemia, neuropathy, poor glucose control, infection, and other contributing factors. Treatment generally includes debridement, infection control, off-loading, and may include administration of either growth factors (e.g., platelet-derived growth factor (PDGF)) or biologic dressings.

MicroRNAs (miRNAs) are a class of small, endogenous and non-coding RNAs able to negatively regulate gene expression by targeting specific messenger RNAs (mRNAs) and inducing their degradation or translational repression (Ambros, Nature 431:350-355 (2004); Bartel, Cell 136:215-233 (2009)). A recent study has defined mRNA degradation as the predominant mechanistic effect of miRNA on its mRNA targets (Guo et al., Nature 2010; 466:835-840).

MicroRNAs have been implicated in a number of biological processes including regulation and maintenance of cardiac function, vascular inflammation and development of vascular pathologies (see Eva Van Rooij and Eric Olson, J. Clin. Invest. 117(9):2369-2376 (2007); Chien, Nature 447: 389-390 (2007); Kartha and Subramanian, J. Cardiovasc. Transl. Res. 3:256-270 (2010); Urbich et al., Cardiovasc. Res. 79:581-588 (2008)). miRNAs have also been reported to be involved in the development of organisms (Ambros, Cell 113:673-676 (2003)) and are differentially expressed in numerous tissues (Xu et al., Curr. Biol. 13:790-795 (2003); Landgraf et al., Cell 129:1401-14 (2007)), in viral infection processes (Pfeffer et al., Science 304:734-736 (2004)), and associated with oncogenesis (Calin et al., Proc. Natl. Acad. Sci. USA 101:2999-3004 (2004)); Calin et al., Proc. Natl. Acad. Sci. USA 99(24):15524-15529 (2002)).

Accordingly, modulating the function and/or activity of microRNAs may present therapeutic targets in the development of effective treatments for a variety of conditions.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MIRG_050_02US_SeqList_ST25.txt, date recorded: Apr. 25, 2018, file size 161 kilobytes). However, delivery of an antisense-based therapeutic targeting a miRNA can pose several challenges. The binding affinity and specificity to a specific miRNA, efficiency of cellular uptake, and nuclease resistance can all be factors in the delivery and activity of an oligonucleotide-based therapeutic. For example, when oligonucleotides are introduced into intact cells they may be attacked and degraded by nucleases leading to a loss of activity. Thus, a useful antisense therapeutic may have good resistance to extra- and intracellular nucleases, as well as be able to penetrate the cell membrane. Conversely, if on-target effects are undesirable in tissues and sites other than that in which the therapeutic is administered, sensitivity to nuclease degradation may limit distal tissue exposure and activity or limit systemic toxicity.

Thus, there is a need for stable and efficacious oligonucleotide-based inhibitors including those for such miRNAs as, for example, miR-92. There is also a need for identification of biomarkers for miRNA modulators, for guiding treatment decisions. The oligonucleotides of the present invention can have advantages in potency, efficiency of delivery, target specificity, stability, and/or toxicity when administered to a subject.

SUMMARY OF THE INVENTION

The present invention provides an oligonucleotide comprising a sequence selected from Table 1 and Table 2. The oligonucleotide can comprise at least one non-locked nucleotide that is 2' O-alkyl or 2' halo modified. In some embodiments, the oligonucleotide comprises at least one LNA that has a 2' to 4' methylene bridge. In some embodiments, the oligonucleotide has a 5' cap structure, 3' cap structure, or 5' and 3' cap structure. In some embodiments, the oligonucleotide comprises one or more phosphorothioate linkages. In some embodiments, the oligonucleotide is fully phosphorothioate-linked. In yet other embodiments, the oligonucleotide comprises a pendent lipophilic group. Also provided herein is a pharmaceutical composition comprising an effective amount of the oligonucleotide or a pharmaceutically-acceptable salt thereof, and a pharmaceutically-acceptable carrier or diluent. In some embodiments, the pharmaceutically-acceptable carrier comprises a colloidal dispersion system, macromolecular complex, nanocapsule, microsphere, bead, oil-in-water emulsion, micelle, mixed micelle, or liposome.

The present invention also provides a method of reducing or inhibiting activity of miR-92 in a cell comprising contacting the cell with an oligonucleotide disclosed herein, such as an oligonucleotide selected from Table 2. In some embodiments, the cell is a mammalian cell. In some embodiments, the cell is a cardiac or muscle cell. In some embodiments, the cell is involved in wound healing. In some embodiments, the cell is a fibrocyte, fibroblast, keratinocyte or endothelial cell. In yet other embodiments, the cell is in vitro, in vivo or ex vivo.

The present invention also provides a method of promoting angiogenesis in a subject comprising administering to the subject an oligonucleotide disclosed herein, such as an oligonucleotide selected from Table 2. In some embodiments, the subject suffers from ischemia, myocardial infarction, chronic ischemic heart disease, peripheral or coronary artery occlusion, ischemic infarction, stroke, atherosclerosis, acute coronary syndrome, coronary artery disease, carotid artery disease, diabetes, chronic wound(s), or peripheral vascular disease (e.g., peripheral artery disease). In some embodiments, the subject is a human.

The present invention also provides a method of promoting wound healing in a subject comprising administering to the subject a miR-92 inhibitor. In some embodiments, the miR-92 inhibitor is an oligonucleotide comprising a sequence that is at least partially complementary to miR-92. The oligonucleotide can comprise at least one non-locked nucleotide that is 2' O-alkyl or 2' halo modified. In some embodiments, the oligonucleotide comprises at least one LNA that has a 2' to 4' methylene bridge. In some embodiments, the miR-92 inhibitor is an oligonucleotide comprising a sequence of 16 nucleotides, wherein the sequence is complementary to miR-92 and comprises no more than three contiguous LNAs, wherein from the 5' end to the 3' end, positions 1, 6, 10, 11, 13 and 16 of the sequence are LNAs. In some embodiments, position 2 from the 5' end of the oligonucleotide comprising a sequence of 16 nucleotides is a deoxyribonucleic acid (DNA) nucleotide that is 5-methylcytosine. In some embodiments, the miR-92 inhibitor is an oligonucleotide comprising a sequence of 16 nucleotides, wherein the sequence is complementary to miR-92 and comprises no more than three contiguous LNAs, wherein from the 5' end to the 3' end, positions 1, 3, 6, 8, 10, 11, 13, 14 and 16 of the sequence are LNAs. In some embodiments, the miR-92 inhibitor is an oligonucleotide comprising a sequence of 16 nucleotides, wherein the sequence is complementary to miR-92 and comprises no more than three contiguous LNAs, wherein from the 5' end to the 3' end, positions 1, 5, 6, 8, 10, 11, 13, 15 and 16 of the sequence are LNAs. In some embodiments, the miR-92 inhibitor is an oligonucleotide comprising a sequence of 16 nucleotides, wherein the sequence is complementary to miR-92 and comprises no more than three contiguous LNAs, wherein from the 5' end to the 3' end, positions 1, 3, 6, 9, 10, 11, 13, 14 and 16 of the sequence are LNAs. In some embodiments, the oligonucleotide has a 5' cap structure, 3' cap structure, or 5' and 3' cap structure. In some embodiments, the oligonucleotide comprises one or more phosphorothioate linkages. In some embodiments, the oligonucleotide is fully phosphorothioate-linked. In yet other embodiments, the oligonucleotide comprises a pendent lipophilic group. In some embodiments, the miR-92 inhibitor is an oligonucleotide disclosed herein, such as an oligonucleotide selected from Tables 1 or 2. In some embodiments, the subject suffers from diabetes, wounds, peripheral or coronary artery occlusion, or peripheral vascular disease (e.g., peripheral artery disease). In some embodiments, the subject is a human. In some embodiments, the wound is a chronic wound, diabetic foot ulcer, venous stasis leg ulcer or pressure sore. In some embodiments, administration of the miR-92 oligonucleotide inhibitor produces an improvement in re-epithelialization, granulation and/or neoangiogenesis of a wound in the subject during wound healing. In some embodiments, the improvement in re-epithelialization, granulation and/or neoangiogenesis (neovascularization) of the wound is as compared to the subject receiving no treatment. In some embodiments, the improvement in re-epithelialization, granulation and/or neoangiogenesis of the wound is as compared to the subject receiving treatment with an agent known to promote wound healing. In some embodiments, the agents known to promote wound healing are growth factors. In some embodiments, the growth factors are platelet derived growth factor (PDGF) or vascular endothelial growth factor (VEGF).

The present invention also provides an oligonucleotide comprising a sequence of 16 nucleotides, wherein the sequence is complementary to miR-92 and comprises no more than three contiguous LNAs, wherein from the 5' end to the 3' end, positions 1, 6, 10, 11, 13 and 16 of the sequence are LNAs, and wherein position 2 from the 5' end comprises a deoxyribonucleic acid (DNA) nucleotide that is 5-methylcytosine. In some embodiments, the oligonucleotide comprises LNAs at positions 1, 3, 6, 8, 10, 11, 13, 14 and 16 from the 5' end to the 3' end. In other embodiments, the oligonucleotide comprises LNAs at positions 1, 5, 6, 8, 10, 11, 13, 15 and 16 from the 5' end to the 3' end. In yet other embodiments, the oligonucleotide comprises LNAs at positions 1, 3, 6, 9, 10, 11, 13, 14 and 16 from the 5' end to the 3' end. The oligonucleotide can further comprise at least one non-locked nucleotide that is 2'-deoxy, 2' O-alkyl or 2' halo modified. In some embodiments, all non-locked nucleotides of the oligonucleotide are 2'-deoxy modified. In some embodiments, the oligonucleotide comprises at least one LNA that has a 2' to 4' methylene bridge. In some embodiments, the oligonucleotide has a 5' cap structure, 3' cap structure, or 5' and 3' cap structure. In some embodiments, the oligonucleotide comprises one or more phosphorothioate linkages. In some embodiments, the oligonucleotide is fully phosphorothioate-linked. In yet other embodiments, the oligonucleotide comprises a pendent lipophilic group. In some embodiments, the presence of the 5-methylcytosine at position 2 from the 5' end of the oligonucleotide inhibitor comprising a sequence of 16 nucleotides confers increased in vivo, ex vivo and/or in vitro efficacy as compared to an oligonucleotide inhibitor containing the same sequence as well as number and positions of LNAs but lacks the 5-methylcytosine. In some embodiments, the increased efficacy is evidenced by elimination or an enhanced reduction in function and/or activity of miR-92.

The present invention also provides a method of reducing or inhibiting activity or function of a miRNA in a cell comprising contacting the cell with the oligonucleotide described herein comprising a sequence of 16 nucleotides, wherein the sequence is complementary to a miRNA and comprises no more than three contiguous LNAs, wherein from the 5' end to the 3' end, positions 1, 6, 10, 11, 13 and 16 of the sequence are LNAs. In some embodiments, the oligonucleotide comprises LNAs at positions 1, 3, 6, 8, 10, 11, 13, 14 and 16 from the 5' end to the 3' end. In other embodiments, the oligonucleotide comprises LNAs at positions 1, 5, 6, 8, 10, 11, 13, 15 and 16 from the 5' end to the 3' end. In yet other embodiments, the oligonucleotide comprises LNAs at positions 1, 3, 6, 9, 10, 11, 13, 14 and 16 from the 5' end to the 3' end. In some embodiments, the sequence is complementary to miR-92. In some embodiments, the cell is a mammalian cell. In some embodiments, the cell is a cardiac or muscle cell. In some embodiments, the cell is involved in wound healing. In some embodiments, the cell is a fibrocyte, fibroblast, keratinocyte or endothelial cell. In yet other embodiments, the cell is in vitro, in vivo or ex vivo.

The present invention also provides a method of promoting angiogenesis in a subject comprising administering to the subject the oligonucleotide described herein comprising a sequence of 16 nucleotides, wherein the sequence is complementary to miR-92 and comprises no more than three contiguous LNAs, wherein from the 5' end to the 3' end, positions 1, 6, 10, 11, 13 and 16 of the sequence are LNAs. In some embodiments, the oligonucleotide comprises LNAs at positions 1, 3, 6, 8, 10, 11, 13, 14 and 16 from the 5' end to the 3' end. In other embodiments, the oligonucleotide comprises LNAs at positions 1, 5, 6, 8, 10, 11, 13, 15 and 16 from the 5' end to the 3' end. In yet other embodiments, the oligonucleotide comprises LNAs at positions 1, 3, 6, 9, 10, 11, 13, 14 and 16 from the 5' end to the 3' end. In some embodiments, the subject suffers from ischemia, myocardial infarction, chronic ischemic heart disease, peripheral or coronary artery occlusion, ischemic infarction, stroke, atherosclerosis, acute coronary syndrome, coronary artery disease, carotid artery disease, diabetes, chronic wound(s), or peripheral vascular disease (e.g., peripheral artery disease). In some embodiments, the subject is a human.

The present invention also provides a method of treating ischemia, myocardial infarction, chronic ischemic heart disease, peripheral or coronary artery occlusion, ischemic infarction, stroke, atherosclerosis, acute coronary syndrome, coronary artery disease, carotid artery disease, diabetes, chronic wound(s) or peripheral artery disease in a subject comprising administering to the subject the oligonucleotide described herein comprising a sequence of 16 nucleotides, wherein the sequence is complementary to miR-92 and comprises no more than three contiguous LNAs, wherein from the 5' end to the 3' end, positions 1, 6, 10, 11, 13 and 16 of the sequence are LNAs. In some embodiments, the oligonucleotide comprises LNAs at positions 1, 3, 6, 8, 10, 11, 13, 14 and 16 from the 5' end to the 3' end. In other embodiments, the oligonucleotide comprises LNAs at positions 1, 5, 6, 8, 10, 11, 13, 15 and 16 from the 5' end to the 3' end. In yet other embodiments, the oligonucleotide comprises LNAs at positions 1, 3, 6, 9, 10, 11, 13, 14 and 16 from the 5' end to the 3' end. In some embodiments, the subject is a human.

The present invention is also based, in part, on the discovery of genes significantly regulated by miR-92. Accordingly, another aspect of the present invention is a method for evaluating or monitoring the efficacy of a therapeutic for modulating angiogenesis and/or treating chronic wounds in a subject receiving the therapeutic comprising: measuring the expression of one or more genes listed in Table 3 in a sample from the subject; and comparing the expression of the one or more genes to a pre-determined reference level or level of the one or more genes in a control sample, wherein the comparison is indicative of the efficacy of the therapeutic. Another aspect of the present invention is a method for selecting a subject for treatment with a therapeutic that modulates miR-92 function and/or activity comprising: measuring the expression of one or more genes listed in Table 3 in a sample from the subject, wherein the subject is treated with the therapeutic; and comparing the expression of the one or more genes to a pre-determined reference level or level of the one or more genes in a control sample, wherein the comparison is indicative of whether the subject should be selected for treatment (e.g. further treatment or continued treatment) with the therapeutic. In some embodiments, the methods comprise a subject that suffers from ischemia, myocardial infarction, chronic ischemic heart disease, peripheral or coronary artery occlusion, ischemic infarction, stroke, atherosclerosis, acute coronary syndrome, coronary artery disease, carotid artery disease, diabetes, chronic wound(s) or peripheral vascular disease (e.g., peripheral artery disease). In some embodiments, the subject has a chronic wound, diabetic foot ulcer, venous stasis leg ulcer or pressure sore. In some embodiments, the subject is a human.

In some embodiments, the methods further comprise performing a walk time test on the subject, determining an ankle-bronchial index (ABI) for the subject, performing an arteriography or angiography on the subject, or performing a SPECT analysis on the subject. In some embodiments, the therapeutic modulates miR-92 function and/or activity. The therapeutic can be a miR-92 antagonist, such as a miR-92 inhibitor selected from Tables 1 and 2. In other embodiments, the therapeutic is a miR-92 agonist, such as a miR-92 mimic. In some embodiments, the methods comprise a subject that suffers from ischemia, myocardial infarction, chronic ischemic heart disease, peripheral or coronary artery occlusion, ischemic infarction, stroke, atherosclerosis, acute coronary syndrome, coronary artery disease, carotid artery disease, diabetes, chronic wound(s) or peripheral vascular disease (e.g., peripheral artery disease). In some embodiments, the subject is a human.

Also provided herein is a method for evaluating an agent's ability to promote angiogenesis comprising: measuring the expression of one or more genes listed in Table 3 in a cell contacted with the agent; and comparing the expression of the one or more genes to a pre-determined reference level or level of the one or more genes in a control sample, wherein the comparison is indicative of the agent's ability to promote angiogenesis. In some embodiments, the method further comprises determining miR-92 function, and/or activity in the cell contacted with the agent. In some embodiments, the cell is a mammalian cell. In some embodiments, the cell is a cardiac or muscle cell. In some embodiments, the cell is involved in wound healing. In some embodiments, the cell is a fibrocyte, fibroblast, keratinocyte or endothelial cell. In yet other embodiments, the cell is in vitro, in vivo or ex vivo.

Another aspect of the present invention is a method for evaluating or monitoring the efficacy of a therapeutic for promoting wound healing in a subject receiving the therapeutic comprising: measuring the expression of one or more genes listed in Table 3 in a sample from the subject; and comparing the expression of the one or more genes to a pre-determined reference level or level of the one or more genes in a control sample, wherein the comparison is indicative of the efficacy of the therapeutic. In some embodiments, the therapeutic modulates miR-92 function and/or activity. The therapeutic can be a miR-92 antagonist, such as a miR-92 inhibitor selected from Tables 1 and 2. In other embodiments, the therapeutic is a miR-92 agonist, such as a miR-92 mimic. In some embodiments, the methods comprise a subject that suffers from ischemia, myocardial infarction, chronic ischemic heart disease, peripheral or coronary artery occlusion, ischemic infarction, stroke, atherosclerosis, acute coronary syndrome, coronary artery disease, carotid artery disease, diabetes, chronic wound(s) or peripheral vascular disease (e.g., peripheral artery disease). In some embodiments, the subject is a human.

Also provided herein is a method for evaluating an agent's ability to promote wound healing comprising: measuring the expression of one or more genes listed in Table 3 in a cell contacted with the agent; and comparing the expression of the one or more genes to a pre-determined reference level or level of the one or more genes in a control sample, wherein the comparison is indicative of the agent's ability to promote wound healing. In some embodiments, the method further comprises determining miR-92 function and/or activity in the cell contacted with the agent. In some embodiments, the cell is a mammalian cell. In yet other embodiments, the cell is in vitro, in vivo or ex vivo.

BRIEF DESCRIPTION OF THE DRAWINGS

FIG. 1 illustrates multiple genes significantly regulated by miR-92a modulation in human umbilical vein endothelial cells (HUVECs).

FIG. 2A-C illustrates integrin α5 expression regulation by miR-92a in HUVECs. Integrin α5 (ITGA5) transcript (FIG. 2A-B) and protein (FIG. 2C) levels are increased in response to miR-92a inhibition and decreased in response to miR-92a mimic. FIGS. 2A-B show the indicated concentrations that the indicated oligonucleotides were lipid-transfected or passively delivered to HUVECs, respectively. FIG. 2C shows the integrin α5 protein levels following lipid-mediated transfection. Passive delivery refers to unassisted oligonucleotide uptake. A (SEQ ID NO. 7), B (SEQ ID NO. 61) and C (SEQ ID NO. 62) are LNA/DNA-containing miR-92a inhibitors. "AntagomiR" is an O-methylated, cholesterol-conjugated inhibitor. D is a single-stranded LNA/DNA control inhibitor.

FIG. 3 illustrates regulation by real time PCR of targets identified by microarray profiling. Four genes identified by microarray profiling are increased in response to miR-92a inhibition and decreased in response to miR-92a mimic, in an independent HUVEC lipid-transfection experiment. The radar plot indicates the relative expression of MAN2A1, CNEP1R1, ERGIC2, and CD93 in response to miR-92a inhibitor or mimic, normalized to HUVECs transfected with lipid without oligonucleotide. The black line indicates where the gene expression would be if there were no change, the red line indicates the gene expression in response to D (control oligo) transfection.

FIG. 5A illustrates the percent re-epithelialization of wounds in the in vivo model of impaired wound healing from phosphate buffered saline (PBS; vehicle-control), vascular endothelial growth factor (VEGF; positive control) and oligonucleotide inhibitors of miR-92 (A (SEQ ID NO 7); C (SEQ ID NO. 62)) treatment groups. FIG. 5B illustrates the percent granulation tissue ingrowth or filled in wounds in the in vivo model of impaired wound healing from PBS (vehicle-control), VEGF (positive control) and oligonucleotide inhibitors of miR-92 (A; C) treatment groups. FIG. 5C illustrates the granulation tissue area in wounds in the in vivo model of impaired wound healing from PBS (vehicle-control), VEGF (positive control) and oligonucleotide inhibitors of miR-92 (A; C) treatment groups. FIG. 5D illustrates the average granulation tissue thickness across wounds (wound area divided by wound width) in the in vivo model of impaired wound healing from PBS (vehicle-control), VEGF (positive control) and oligonucleotide inhibitors of miR-92 (A; C) treatment groups. FIGS. 5E-F illustrate the number of CD31+ endothelial cells (FIG. 5E) and the tissue area that was CD31+ (FIG. 5F) in wounds in the in vivo model of impaired wound healing from PBS (vehicle-control) and oligonucleotide inhibitor of miR-92 (A) treatment groups using immunohistochemistry, as an indicator of neovascularization/angiogenesis FIG. 6A-F illustrates results of a second study examining the activity of oligonucleotide inhibitors of miR-92 in an in vivo model of impaired wound healing. FIG. 6A illustrates the percent re-epithelialization of wounds in the in vivo model of impaired wound healing from PBS (vehicle-control), VEGF (positive control), platelet derived growth factor (PDGF; positive control) and oligonucleotide inhibitors of miR-92 (A; C) treatment groups. FIG. 6B illustrates the percent granulation tissue ingrowth or filled in wounds in the in vivo model of impaired wound healing from PBS (vehicle-control), VEGF (positive control), PDGF (positive control) and oligonucleotide inhibitors of miR-92 (A; C) treatment groups. FIG. 6C illustrates the granulation tissue area in wounds in the in vivo model of impaired wound healing from PBS (vehicle-control), VEGF (positive control), PDGF (positive control) and oligonucleotide inhibitors of miR-92 (A; C) treatment groups. FIG. 6D illustrates the average granulation tissue thickness across wounds (wound area divided by wound width) in the in vivo model of impaired wound healing from PBS (vehicle-control), VEGF (positive control), PDGF (positive control) and oligonucleotide inhibitors of miR-92 (A; C) treatment groups. FIGS. 6E-F illustrate the number of CD31+ endothelial cells (FIG. 6E) and the tissue area that was CD31+ (FIG. 6F) in wounds in the in vivo model of impaired wound healing from PBS (vehicle-control), VEGF (positive control), PDGF (positive control) and oligonucleotide inhibitor of miR-92 (A) treatment groups using immunohistochemistry, as an indicator of neovascularization/angiogenesis

FIG. 8A-D illustrates the effects of saline (vehicle-control; FIG. 8A), PDGF (positive control; FIG. 8B), and oligonucleotide inhibitor of miR-92 (A; FIGS. 8C-D) treatments on the protein expression of the miR-92 target ITGA5 in wounds in the in vivo model of impaired wound healing as evaluated using immunohistochemistry.

DETAILED DESCRIPTION OF THE INVENTION

Figure 4:
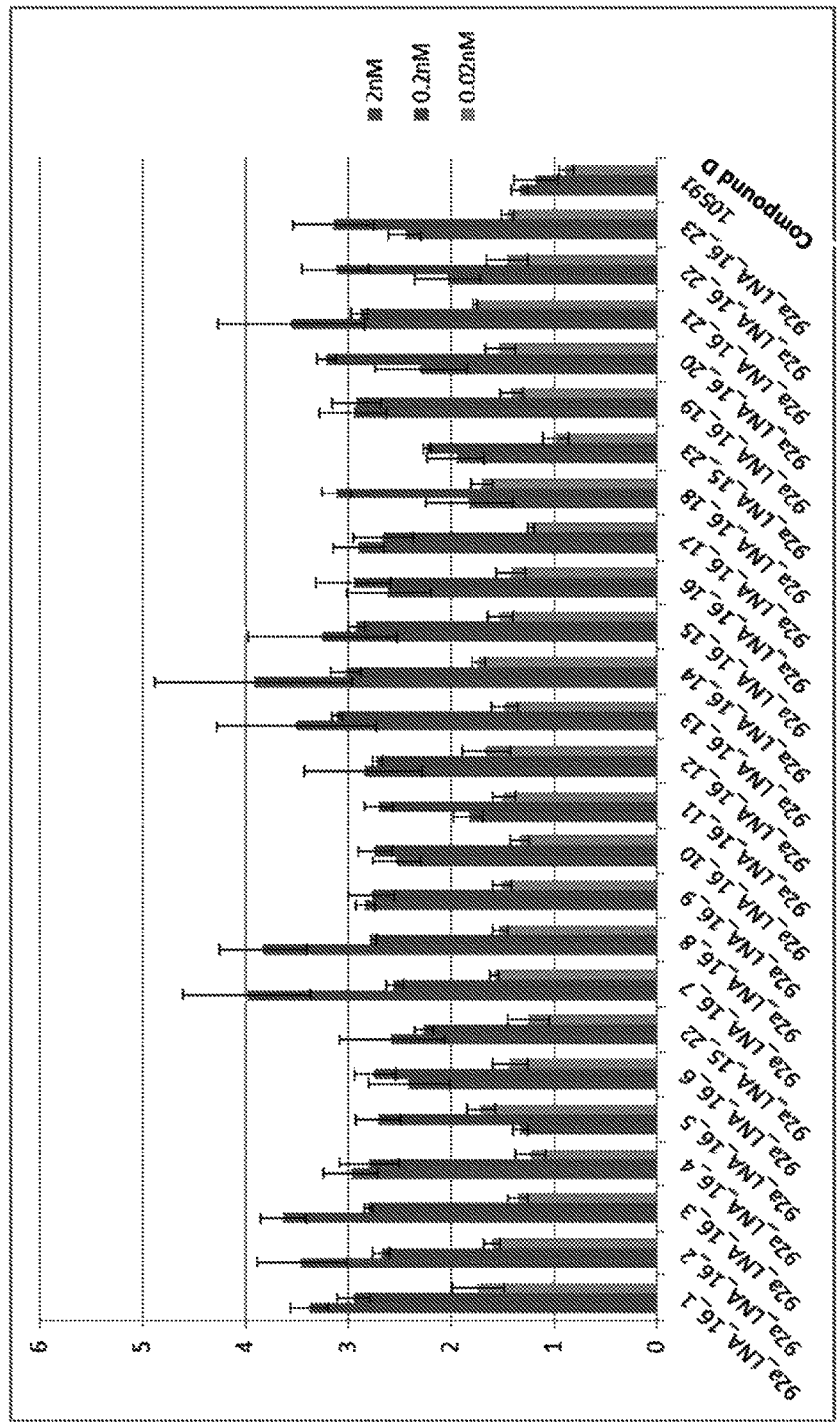
FIG. 4 illustrates a dual luciferase assay for testing of inhibitor design activity. MiR-92a inhibitors were ranked based on their ability to de-repress the expression of luciferase from a dual-luciferase reporter plasmid. Shown is an example set of data from the first of three replicate experiments.

The present invention provides oligonucleotide inhibitors that inhibit the activity or function of miR-92 and compositions and uses thereof. Also provided herein are miR-92 agonists, such as a miR-92 mimic.

MiR-92 is located in the miR-17-92 cluster, which consists of miR-17-5p, miR-17-3p, miR-18a, miR-19a, miR-20a, miR-19b, and miR-92-1 (Venturini et al., Blood 109 10:4399-4405 (2007)). The pre-miRNA sequence for miR-92 is processed into a mature sequence (3p) and a star (i.e. minor or 5p) sequence. The star sequence is processed from the other arm of the stem loop structure. The mature and star miRNA sequences for human, mouse, and rat miR-92 are provided:

```
Human mature miR-92 (i.e. hsa-miR-92a-3p)
                                          (SEQ ID NO: 1)
5'-UAUUGCACUUGUCCCGGCCUGU-3'

Human miR-92a-1* (i.e. hsa-miR-92a-1-5p)
                                          (SEQ ID NO: 2)
5'-AGGUUGGGAUCGGUUGCAAUGCU-3'

Human miR-92a-2* (i.e. hsa-miR-92a-2-5p)
                                          (SEQ ID NO: 3)
5'-GGGUGGGGAUUUGUUGCAUUAC-3'

Mouse mature miR-92 (i.e. mmu-miR-92a-3p)
                                          (SEQ ID NO: 4)
5'-UAUUGCACUUGUCCCGGCCUG-3'

Mouse miR-92a-1* (i.e. mmu-miR-92a-1-5p)
                                          (SEQ ID NO: 5)
5'-AGGUUGGGAUUUGUCGCAAUGCU-3'
```

-continued

Mouse miR-92a-2* (i.e. mmu-miR-92a-2-5p)
(SEQ ID NO: 6)
5'-AGGUGGGGAUUGGUGGCAUUAC-3'

Rat mature miR-92 (i.e. rno-miR-92a-3p)
(SEQ ID NO: 4)
5'-UAUUGCACUUGUCCCGGCCUG-3'

Rat miR-92a-1* (i.e. rno-miR-92a-1-5p)
(SEQ ID NO: 5)
5'-AGGUUGGGAUUUGUCGCAAUGCU-3'

Rat miR-92a-2* (i.e. rno-miR-92a-2-5p)
(SEQ ID NO: 6)
5'-AGGUGGGGAUUAGUGCCAUUAC-3'

The above sequences can be either ribonucleic acid sequences or deoxyribonucleic acid sequences or a combination of the two (i.e. a nucleic acid comprising both ribonucleotides and deoxyribonucleotides). It is understood that a nucleic acid comprising any one of the sequences described herein will have a thymidine base in place of the uridine base for DNA sequences and a uridine base in place of a thymidine base for RNA sequences.

In some embodiments, the oligonucleotide comprising a sequence complementary to miR-92 is a miR-92 inhibitor. The oligonucleotide comprising a sequence complementary to miR-92 can be an oligonucleotide inhibitor. In the context of the present invention, the term "oligonucleotide inhibitor", "antimiR", "antagonist", "antisense oligonucleotide or ASO", "oligomer", "anti-microRNA oligonucleotide or AMO", or "mixmer" is used broadly and encompasses an oligomer comprising ribonucleotides, deoxyribonucleotides, modified ribonucleotides, modified deoxyribonucleotides or a combination thereof, that inhibits the activity or function of the target microRNA (miRNA) by fully or partially hybridizing to the miRNA thereby repressing the function or activity of the target miRNA.

The term "miR-92" as used herein includes pri-miR-92, pre-miR-92, miR-92, miR-92a, miR-92b, miR-92a-3p, and hsa-miR-92a-3p.

In some embodiments, certain oligonucleotide inhibitors of the present invention may show a greater inhibition of the activity or function of miR-92 in cells as compared to other miR-92 inhibitors. In some embodiments, the cell is a cardiac or muscle cell. In some embodiments, the cell is involved in wound healing. In some embodiments, the cell is a fibrocyte, fibroblast, keratinocyte or endothelial cell. In yet other embodiments, the cell is in vivo or ex vivo. In some embodiments, the oligonucleotide inhibitors of miR-92 of the present invention show higher efficacy as compared to other oligonucleotide inhibitors of miR-92 as measured by the amount of de-repression of a miR-92 target such as a gene selected from Table 3.

The term "other miR-92 inhibitors" includes nucleic acid inhibitors such as antisense oligonucleotides, antimiRs, antagomiRs, mixmers, gapmers, aptamers, ribozymes, small interfering RNAs, or small hairpin RNAs; antibodies or antigen binding fragments thereof; and/or drugs, which inhibit the expression or activity of miR-92. It is possible that a particular oligonucleotide inhibitor of the present invention may show a greater inhibition of miR-92 in cells (e.g., muscle cells, cardiac cells, endothelial cells, fibrocytes, fibroblasts, or keratinocytes) compared to other oligonucleotide inhibitors of the present invention. The term "greater" as used herein refers to quantitatively more or statistically significantly more.

The activity of the oligonucleotide in modulating the function and/or activity of miR-92 may be determined in vitro, ex vivo and/or in vivo. For example, when inhibition of miR-92 activity is determined in vitro, the activity may be determined using a dual luciferase assay. The dual luciferase assay can be any dual luciferase assay known in the art. The dual luciferase assay can be a commercially available dual luciferase assay. The dual luciferase assay, as exemplified by the commercially available product PsiCHECK™ (Promega), can involve placement of the miR recognition site in the 3' UTR of a gene for a detectable protein (e.g., *renilla* luciferase). The construct can be co-expressed with miR-92, such that inhibitor activity can be determined by change in signal. A second gene encoding a detectable protein (e.g., firefly luciferase) can be included on the same plasmid, and the ratio of signals determined as an indication of the antimiR-92 activity of a candidate oligonucleotide. In some embodiments, the oligonucleotide significantly inhibits such activity, as determined in the dual luciferase activity, at a concentration of about 50 nM or less, or in other embodiments, 40 nM or less, 20 nM or less, or 10 nM or less. For example, the oligonucleotide may have an IC50 for inhibition of miR-92 activity of about 50 nM or less, 40 nM or less, 30 nM or less, or 20 nM or less, as determined in the dual luciferase assay.

Alternatively, or in addition, the in vivo efficacy of the oligonucleotide inhibitor of a miRNA as provided herein (e.g., miR-92) may also be determined in a suitable animal model. The animal model can be a rodent model (e.g., mouse or rat model). The oligonucleotide may exhibit at least 50% miR-92 target de-repression at a dose of 50 mg/kg or less, 25 mg/kg or less, 10 mg/kg or less or 5 mg/kg or less. In such embodiments, the oligonucleotide may be dosed, delivered or administered to mice intravenously or subcutaneously or delivered locally such as local injection into muscle or a wound (e.g., to the wound margin or wound bed), and the oligonucleotide may be formulated in saline. In some embodiments, the application may be dosed to mice topically or intradermally (i.e., intradermal injection), such as to a wound (e.g., to the wound margin or wound bed). The oligonucleotide inhibitor of miR-92 as provided herein can have increased in vivo efficacy in a particular tissue as compared to other oligonucleotide inhibitors of miR-92.

In some embodiments, the in vivo efficacy of the oligonucleotide is determined in a suitable mouse or rat model for diabetes. In one embodiment, the mouse model is a genetically type II diabetic mice such as db/db mice (Jackson Cat #000642 BKS.Cg Dock(Hom) 7m+/+ Leprdb/j). In one embodiment, the model uses full thickness cutaneous excisional punch biopsy. In other embodiments, the model utilizes an incision, scald or burn. In such embodiments, the oligonucleotide may be dosed to mice intravenously or subcutaneously, or delivered locally such as local injection or topical application to a wound (e.g., the wound margin or wound bed).

In these or other embodiments, the oligonucleotides of the present invention can be stable after administration, being detectable in the circulation and/or target organ for at least three weeks, at least four weeks, at least five weeks, or at least six weeks, or more, following administration. Thus, the oligonucleotide inhibitors of a miRNA (e.g., miR-92) provided herein may provide for less frequent administration, lower doses, and/or longer duration of therapeutic effect as compared to other oligonucleotide inhibitors of the miRNA (e.g., miR-92).

The nucleotide sequence of the oligonucleotide can be substantially complementary to a nucleotide sequence of an RNA, such as a mRNA or miRNA. The nucleotide sequence of the oligonucleotide can be fully complementary to a nucleotide sequence of an RNA, such as a mRNA or miRNA. In some embodiments, the miRNA is miR-92 or miR-92a. The oligonucleotide comprises at least one LNA, such as at least two, at least three, at least five, at least seven or at least nine LNAs. In some embodiments, the oligonucleotide comprises a mix of LNA and non-locked nucleotides. For example, the oligonucleotide may contain at least five or at least seven or at least nine locked nucleotides, and at least one non-locked nucleotide.

Generally, the length of the oligonucleotide and number and position of locked nucleotides can be such that the oligonucleotide reduces miR-92 function and/or activity. In some embodiments, the length of the oligonucleotide and number and position of locked nucleotides is such that the oligonucleotide reduces miR-92 function and/or activity at an oligonucleotide concentration of about 50 nM or less in the in vitro luciferase assay, or at a dose of about 50 mg/kg or less, or about 25 mg/kg or less in a suitable mouse or rat model, each as described. In some embodiments, the length of the oligonucleotide and number and position of locked nucleotides is such that the oligonucleotide reduces miR-92 activity as determined by target de-repression, at a dose of about 50 mg/kg or less, or about 25 mg/kg or less in a suitable mouse or rat model, such as described herein.

The oligonucleotide of the present invention can comprise a sequence of nucleotides in which the sequence comprises at least five LNAs, a LNA at the 5' end of the sequence, a LNA at the 3' end of the sequence, or any combination thereof. In one embodiment, the oligonucleotide comprises a sequence of nucleotides in which the sequence comprises at least five LNAs, a LNA at the 5' end of the sequence, a LNA at the 3' end of the sequence, or any combination thereof, wherein three or fewer of the nucleotides are contiguous LNAs. For example, the oligonucleotide comprises no more than three contiguous LNAs. For example, the oligonucleotide may comprise a sequence with at least five LNAs, a LNA at the 5' end, a LNA at the 3' end, and no more than three contiguous LNAs. The oligonucleotide may comprise a sequence with at least five LNAs, a LNA at the 5' end, a LNA at the 3' end, and no more than three contiguous LNAs, wherein the sequence is at least 16 nucleotides in length. The sequence can be substantially or completely complementary to a RNA, such as mRNA, or miRNA, wherein a substantially complementary sequence may have from 1 to 4 mismatches (e.g., 1 or 2 mismatches) with respect to its target sequence. In one embodiment, the target sequence is a miRNA, such that the oligonucleotide is a miRNA inhibitor, or antimiR. In one embodiment, the target sequence is a miR-92 sequence as provided herein.

In yet another embodiment, the oligonucleotide of the present invention can comprise a sequence complementary to the seed region of a miRNA (e.g., miR-92), wherein the sequence comprises at least five LNAs. The "seed region of a miRNA" is the portion spanning bases 2 to 9 at the 5' end of the miRNA. The oligonucleotide comprising a sequence complementary to the seed region of a miRNA (e.g., miR-92), wherein the sequence comprises at least five LNAs, may comprise a LNA at the 5' end or a LNA at the 3' end, or both a LNA at the 5' end and 3' end. In one embodiment, the oligonucleotide comprising at least 5 LNAs, a LNA at the 5' end and/or a LNA at the 3' end, also has three or fewer consecutive LNAs. In some embodiments, the sequence is at least 16 nucleotides in length. The sequence complementary to the seed region of a miRNA can be substantially complementary or completely complementary.

The oligonucleotides of the present invention may comprise one or more locked nucleic acid (LNAs) residues, or "locked nucleotides." The oligonucleotide of the present invention can contain one or more locked nucleic acid (LNAs) residues, or "locked nucleotides." The oligonucleotides of the present invention may comprise one or more nucleotides containing other sugar or base modifications. The terms "locked nucleotide," "locked nucleic acid unit," "locked nucleic acid residue," "LNA" or "LNA unit" may be used interchangeably throughout the disclosure and refer to a bicyclic nucleoside analogue. For instance, suitable oligonucleotide inhibitors can be comprised of one or more "conformationally constrained" or bicyclic sugar nucleoside modifications (BSN) that confer enhanced thermal stability to complexes formed between the oligonucleotide containing BSN and their complementary target strand. LNAs are described, for example, in U.S. Pat. Nos. 6,268,490, 6,316, 198, 6,403,566, 6,770,748, 6,998,484, 6,670,461, and 7,034, 133, all of which are hereby incorporated by reference in their entireties. LNAs are modified nucleotides or ribonucleotides that contain an extra bridge between the 2' and 4' carbons of the ribose sugar moiety resulting in a "locked" conformation, and/or bicyclic structure. In one embodiment, the oligonucleotide contains one or more LNAs having the structure shown by structure A below. Alternatively or in addition, the oligonucleotide may contain one or more LNAs having the structure shown by structure B below. Alternatively or in addition, the oligonucleotide contains one or more LNAs having the structure shown by structure C below.

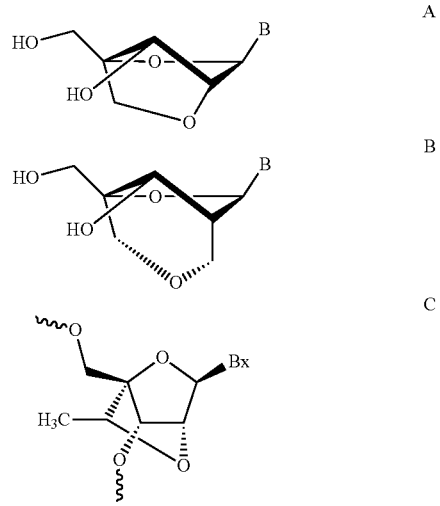

When referring to substituting a DNA or RNA nucleotide by its corresponding locked nucleotide in the context of the present invention, the term "corresponding locked nucleotide" is intended to mean that the DNA/RNA nucleotide has been replaced by a locked nucleotide containing the same naturally-occurring nitrogenous base as the DNA/RNA nucleotide that it has replaced or the same nitrogenous base that is chemically modified. For example, the corresponding locked nucleotide of a DNA nucleotide containing the nitrogenous base C may contain the same nitrogenous base C or the same nitrogenous base C that is chemically modified, such as 5-methylcytosine.

The term "non-locked nucleotide" refers to a nucleotide different from a locked-nucleotide, i.e. the term "non-locked nucleotide" includes a DNA nucleotide, an RNA nucleotide as well as a modified nucleotide where a base and/or sugar is modified except that the modification is not a locked modification.

Other suitable locked nucleotides that can be incorporated in the oligonucleotides of the present invention include those described in U.S. Pat. Nos. 6,403,566 and 6,833,361, both of which are hereby incorporated by reference in their entireties.

In exemplary embodiments, the locked nucleotides have a 2' to 4' methylene bridge, as shown in structure A, for example. In other embodiments, the bridge comprises a methylene or ethylene group, which may be substituted, and which may or may not have an ether linkage at the 2' position.

Oligonucleotide inhibitors of the present invention may include modified nucleotides that have a base modification or substitution. The natural or unmodified bases in RNA are the purine bases adenine (A) and guanine (G), and the pyrimidine bases cytosine (C) and uracil (U) (DNA has thymine (T)). Modified bases, also referred to as heterocyclic base moieties, include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (including 5-bromo, 5-trifluoromethyl and other 5-substituted uracils and cytosines), 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. In certain embodiments, oligonucleotide inhibitors targeting miR-92 comprise one or more BSN modifications (i.e., LNAs) in combination with a base modification (e.g. 5-methyl cytidine).

Oligonucleotide inhibitors of the present invention may include nucleotides with modified sugar moieties. Representative modified sugars include carbocyclic or acyclic sugars, sugars having substituent groups at one or more of their 2', 3' or 4' positions and sugars having substituents in place of one or more hydrogen atoms of the sugar. In certain embodiments, the sugar is modified by having a substituent group at the 2' position. In additional embodiments, the sugar is modified by having a substituent group at the 3' position. In other embodiments, the sugar is modified by having a substituent group at the 4' position. It is also contemplated that a sugar may have a modification at more than one of those positions, or that an oligonucleotide inhibitor may have one or more nucleotides with a sugar modification at one position and also one or more nucleotides with a sugar modification at a different position.

The oligonucleotide may comprise, consist essentially of, or consist of, an antisense sequence to miR-92. In one embodiment, the oligonucleotide comprises an antisense sequence directed to miR-92. For example, the oligonucleotide can comprise a sequence that is at least partially complementary to a mature miR-92 sequence, e.g. at least about 75%, 76%, 77%, 78%, 79%, 80%, 81%, 82%, 83%, 84%, 85%, 6%, 87%, 88%, 89%, 90%, 91%, 92%, 93%, 94%, 95%, 96%, 97%, 98%, or 99% complementary to a human mature miR-92 sequence. In one embodiment, the oligonucleotide inhibitor as provided herein comprises a sequence that is 100% or fully complementary to a mature miR-92 sequence. It is understood that the sequence of the oligonucleotide inhibitor is considered to be complementary to miR-92 even if the oligonucleotide inhibitor sequence includes a modified nucleotide instead of a naturally-occurring nucleotide. For example, if a mature sequence of miR-92 comprises a guanosine nucleotide at a specific position, the oligonucleotide inhibitor may comprise a modified cytidine nucleotide, such as a locked cytidine nucleotide or 2'-fluoro-cytidine, at the corresponding position The term "about" as used herein is meant to encompass variations of +/−10% and more preferably +/−5%, as such variations are appropriate for practicing the present invention.

In certain embodiments, the oligonucleotide comprises a nucleotide sequence that is completely complementary to a nucleotide sequence of miR-92. In particular embodiments, the oligonucleotide comprises, consists essentially of, or consists of the nucleotide sequence complementary to miR-92. In this context, "consists essentially of" includes the optional addition of nucleotides (e.g., one or two) on either or both of the 5' and 3' ends, so long as the additional nucleotide(s) do not substantially affect (as defined by an increase in IC50 of no more than 20%) the oligonucleotide's inhibition of the target miRNA activity in the dual luciferase assay or animal (e.g., mouse) model.

The oligonucleotide can generally have a nucleotide sequence designed to target mature miR-92. The oligonucleotide may, in these or other embodiments, also or alternatively be designed to target the pre- or pri-miRNA forms of miR-92. In certain embodiments, the oligonucleotide may be designed to have a sequence containing from 1 to 5 (e.g., 1, 2, 3, or 4) mismatches relative to the fully complementary (mature) miR-92 sequence. In certain embodiments, such antisense sequences may be incorporated into shRNAs or other RNA structures containing stem and loop portions, for example.

The oligonucleotide can be from 8 to 20 nucleotides in length, from 15 to 50 nucleotides in length, from 18 to 50 nucleotides in length, from 10 to 18 nucleotides in length, or from 11 to 16 nucleotides in length. The oligonucleotide in some embodiments is about 8, about 9, about 10, about 11, about 12, about 13, about 14, about 15, about 16, about 17, or about 18 nucleotides in length. In one embodiment, the present invention provides an oligonucleotide inhibitor of miR-92 that has a length of 11 to 16 nucleotides. In various embodiments, the oligonucleotide inhibitor targeting miR-92 is 11, 12, 13, 14, 15, or 16 nucleotides in length. In one embodiment, the oligonucleotide inhibitor of miR-92 has a length of 12 nucleotides. In some embodiments, the oligonucleotide inhibitor of miR-92 is at least 16 nucleotides in length.

Generally, the number and position of LNA can be such that the oligonucleotide reduces miR-92 activity or function. In one embodiment, the number and position of LNAs is such that the oligonucleotide has an increased efficacy relative to a control. In some embodiments, efficacy is a capacity for producing a beneficial or desired result (e.g., clinical result). The beneficial or desired result can be a reduction, amelioration, or removal of a symptom or symptoms of a disease or condition. The beneficial or desired result can be a inhibition, reduction, amelioration, or removal of the activity or function of miR-92. The increased efficacy can be increased in vivo, in vitro, or ex vivo. The control can be an oligonucleotide containing the same sequence as the oligonucleotide comprising LNAs as provided herein but no chemical modifications. The control can be an oligonucleotide containing the same sequence as the oligonucleotide comprising LNAs as provided herein but a different chemical modification motif or pattern. The control can be an oligonucleotide containing the same sequence as the oligonucleotide comprising LNAs as provided herein but a different number and/or position of LNAs. The control can be an oligonucleotide containing the same sequence as well as number and/or position of LNAs, but a different additional modification such as the presence of one or more 5-methylcytosines.

The oligonucleotide as provided herein generally contains at least about 2, at least about 3, at least about 4, at least about 5, at least about 7, or at least about 9 LNAs, but in various embodiments is not fully comprised of LNAs. Generally, the number and position of LNAs is such that the oligonucleotide reduces mRNA or miRNA function or activity. In certain embodiments, the oligonucleotide does not contain a stretch of nucleotides with more than four, or more than three, contiguous LNAs. For example, the oligonucleotide comprises no more than three contiguous LNAs. In these or other embodiments, the oligonucleotide can comprise a region or sequence that is substantially or completely complementary to a miRNA seed region, in which the region or sequence comprises at least two, at least three, at least four, or at least five locked nucleotides.

In certain embodiments, the oligonucleotide inhibitor contains at least 1, at least 2, at least 3, at least 4, or at least 5 DNA nucleotides. In one embodiment, the oligonucleotide inhibitor comprises at least one LNA, wherein each non-locked nucleotide in the oligonucleotide inhibitor is a DNA nucleotide. In one embodiment, the oligonucleotide inhibitor comprises at least two LNAs, wherein each non-locked nucleotide in the oligonucleotide inhibitor is a DNA nucleotide. In one embodiment, at least the second nucleotide from the 5' end of the oligonucleotide inhibitor is a DNA nucleotide. In one embodiment, at least 1, at least 2, at least 3, at least 4, or at least 5 DNA nucleotides in an oligonucleotide as provided herein contains a nitrogenous base that is chemically modified. In one embodiment, the second nucleotide from the 5' end of an oligonucleotide inhibitor as provided herein contains a nitrogenous base that is chemically modified. The chemically modified nitrogenous base can be 5-methylcytosine. In one embodiment, the second nucleotide from the 5' end is a 5-methylcytosine. In one embodiment, an oligonucleotide inhibitor as provided herein comprises a 5-methylcytosine at each LNA that is a cytosine.

In one embodiment, an oligonucleotide inhibitor of miR-92 as provided herein comprises a sequence of 12 to 16 nucleotides, wherein the sequence is at least partially or fully complementary to a mature sequence of miR-92, in which from the 5' end to the 3' end of the oligonucleotide, at least the first and last nucleotide positions are LNAs. In certain embodiments, the oligonucleotide inhibitor of miR-92 has a length of 12 nucleotides. In certain embodiments, the oligonucleotide inhibitor of miR-92 has a length of 13 nucleotides. In certain embodiments, the oligonucleotide inhibitor of miR-92 has a length of 14 nucleotides. In certain embodiments, the oligonucleotide inhibitor of miR-92 has a length of 15 nucleotides. In certain embodiments, the oligonucleotide inhibitor of miR-92 has a length of 16 nucleotides. The oligonucleotide can have a full or partial (i.e., one or more) phosphorothioate backbone. The oligonucleotide can further comprise any additional modification as provided herein including but not limited to one or more chemically modified nitrogenous bases, a 5' and/or 3' cap structure, a pendent lipophilic group and/or 2' deoxy, 2' O-alkyl or 2' halo modification(s). In certain embodiments, the oligonucleotide inhibitor of miR-92 comprising a sequence of from 12 to 16 nucleotides comprises at least one nucleotide with a chemically modified nitrogenous base. The chemically modified nitrogenous base can be a methylated base. In certain embodiments, the chemically modified nitrogenous base is 5-methylcytosine. In one embodiment, each LNA that is a cytosine is a 5-methylcytosine. In certain embodiments, an oligonucleotide inhibitor as provided herein comprising at least one nucleotide with a chemically modified nitrogenous base (e.g., 5-methylcytosine) shows increased efficacy as compared to the same oligonucleotide inhibitor lacking the chemically modified nitrogenous base. The increased efficacy can be an increased reduction or inhibition of miR-92 function and/or activity. The increased efficacy can be in vivo, ex vivo and/or in vitro.

In one embodiment, the oligonucleotide can comprise a sequence of 13 to 16 nucleotides, in which from the 5' end to the 3' end of the oligonucleotide, positions 1, 6, 10, 11 and 13 are LNAs, and the remaining positions are non-locked nucleotides, wherein the oligonucleotide is at least partially complementary to a miRNA or a seed region of a miRNA, in which the miRNA may in some embodiments, be miR-92. The oligonucleotide can be fully complementary to the miRNA, in which the miRNA may in some embodiments, be miR-92. In some embodiments, at least one non-locked nucleotide comprises a nitrogenous base that is chemically modified. In certain embodiments, the oligonucleotide inhibitor comprises a nucleotide containing a chemically modified nitrogenous base at a second nucleotide position from the 5' end to the 3' end of the oligonucleotide. In certain embodiments, the second nucleotide position is a cytosine and the chemically modified nitrogenous base is a 5-methylcytosine. In one embodiment, the presence of the chemically modified nitrogenous base(s) (e.g., 5-methylcytosine) in the oligonucleotide inhibitor has increased in vivo or in vitro efficacy as compared to an oligonucleotide with the same number and/or position of LNAs but no chemically modified nitrogenous base (e.g., 5-methylcytosine). The increased efficacy can be an increased reduction of miRNA (e.g., miR-92) function and/or activity.

In another embodiment, the oligonucleotide can comprise at least 16 nucleotides, in which from the 5' end to the 3' end of the oligonucleotide, positions 1, 3, 6, 8, 10, 11, 13, 14, and 16 are LNAs, and the remaining positions are non-locked nucleotides, the oligonucleotide is at least partially complementary to a miRNA or a seed region of a miRNA, in which the miRNA may in some embodiments, be miR-92. The oligonucleotide can be fully complementary to the miRNA, in which the miRNA may in some embodiments, be miR-92. In some embodiments, the second nucleotide from the 5' end comprises a nitrogenous base that is chemically modified (e.g. 5-methylcytosine). In one embodiment, the presence of the chemically modified nitrogenous base(s) (e.g., 5-methylcytosine) in the oligonucleotide inhibitor has increased in vivo or in vitro efficacy as compared to an oligonucleotide with the same number and/or position of LNAs but no chemically modified nitrogenous base (e.g., 5-methylcytosine). The increased efficacy can be an increased reduction of miRNA (e.g., miR-92) function and/or activity.

In another embodiment, the oligonucleotide can comprise at least 16 nucleotides, in which from the 5' end to the 3' end of the oligonucleotide, positions 1, 5, 6, 8, 10, 11, 13, 15, and 16 are LNAs, and the remaining positions are non-locked nucleotides, the oligonucleotide is at least partially complementary to a miRNA or a seed region of a miRNA, in which the miRNA may in some embodiments, be miR-92. The oligonucleotide can be fully complementary to the miRNA, in which the miRNA may in some embodiments, be miR-92.

In some embodiments, the second nucleotide from the 5' end comprises a nitrogenous base that is chemically modified (e.g. 5-methylcytosine). In one embodiment, the presence of the chemically modified nitrogenous base(s) (e.g., 5-methylcytosine) in the oligonucleotide inhibitor has increased in vivo or in vitro efficacy as compared to an oligonucleotide with the same number and/or position of LNAs but no chemically modified nitrogenous base (e.g., 5-methylcytosine). The increased efficacy can be an increased reduction of miRNA (e.g., miR-92) function and/or activity.

In another embodiment, the oligonucleotide can comprise at least 16 nucleotides, in which from the 5' end to the 3' end of the oligonucleotide, positions 1, 3, 6, 9, 10, 11, 13, 14, and 16 are LNAs, and the remaining positions are non-locked nucleotides, the oligonucleotide is at least partially complementary to a miRNA or a seed region of a miRNA, in which the miRNA may in some embodiments, be miR-92. The oligonucleotide can be fully complementary to the miRNA, in which the miRNA may in some embodiments, be miR-92. In some embodiments, the second nucleotide from the 5' end comprises a nitrogenous base that is chemically modified (e.g. 5-methylcytosine). In one embodiment, the presence of the chemically modified nitrogenous base(s) (e.g., 5-methylcytosine) in the oligonucleotide inhibitor has increased in vivo or in vitro efficacy as compared to an oligonucleotide with the same number and/or position of LNAs but no chemically modified nitrogenous base (e.g., 5-methylcytosine). The increased efficacy can be an increased reduction of miRNA (e.g., miR-92) function and/or activity.

In some embodiments, the oligonucleotide is selected from Tables 1 or 2. In certain embodiments, the oligonucleotide is an oligonucleotide inhibitor selected from Table 2.

In some embodiments, an oligonucleotide inhibitor as provided herein (e.g., miR-92 oligonucleotide inhibitor) shows at least about 0.5%, at least about 1%, at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least about 99% greater inhibition of the function and/or activity of a target miRNA (e.g., miR-92) as compared to other inhibitors of the target miRNA (e.g., miR-92). The improvement or increase can be in vitro, ex vivo and/or in vivo.

In some embodiments, an oligonucleotide inhibitor as provided herein (e.g., miR-92 oligonucleotide inhibitor) comprising a 5-methylcytosine produces at least about 0.5%, at least about 1%, at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least about 99% of an increase or improvement in the reduction of function and/or activity of a target miRNA (e.g., miR-92) as compared to an oligonucleotide with the same nucleotide sequence as well as LNA/DNA pattern but lacking a 5-methylcytosine. The improvement or increase can be in vitro, ex vivo and/or in vivo. In some cases, all LNA cytosines in an oligonucleotide inhibitor as provided herein is a 5-methylcytosine LNA.

In some embodiments for non-locked nucleotides, the nucleotide may contain a 2' modification with respect to a 2' hydroxyl. For example, the 2' modification may be 2' deoxy. Incorporation of 2'-modified nucleotides in antisense oligonucleotides may increase resistance of the oligonucleotides to nucleases. Incorporation of 2'-modified nucleotides in antisense oligonucleotides may increase their thermal stability with complementary RNA. Incorporation of 2'-modified nucleotides in antisense oligonucleotides may increase both resistance of the oligonucleotides to nucleases and their thermal stability with complementary RNA. Various modifications at the 2' positions may be independently selected from those that provide increased nuclease sensitivity, without compromising molecular interactions with the RNA target or cellular machinery. Such modifications may be selected on the basis of their increased potency in vitro, ex vivo or in vivo. Exemplary methods for determining increased potency (e.g., IC50) for miR-92 inhibition are described herein, including, but not limited to, the dual luciferase assay and in vivo miR-92 abundance or target de-repression.

In some embodiments the 2' modification may be independently selected from O-alkyl (which may be substituted), halo, and deoxy (H). Substantially all, or all, nucleotide 2' positions of the non-locked nucleotides may be modified in certain embodiments, e.g., as independently selected from O-alkyl (e.g., O-methyl), halo (e.g., fluoro), deoxy (H), and amino. For example, the 2' modifications may each be independently selected from O-methyl (OMe) and fluoro (F). In exemplary embodiments, purine nucleotides each have a 2' OMe and pyrimidine nucleotides each have a 2'-F. In certain embodiments, from one to about five 2' positions, or from about one to about three 2' positions are left unmodified (e.g., as 2' hydroxyls).

2' modifications in accordance with the invention can also include small hydrocarbon substituents. The hydrocarbon substituents include alkyl, alkenyl, alkynyl, and alkoxyalkyl, where the alkyl (including the alkyl portion of alkoxy), alkenyl and alkynyl may be substituted or unsubstituted. The alkyl, alkenyl, and alkynyl may be C1 to C10 alkyl, alkenyl or alkynyl, such as C1, C2, or C3. The hydrocarbon substituents may include one or two or three non-carbon atoms, which may be independently selected from nitrogen (N), oxygen (O), and/or sulfur (S). The 2' modifications may further include the alkyl, alkenyl, and alkynyl as O-alkyl, O-alkenyl, and O-alkynyl.

Exemplary 2' modifications in accordance with the invention can include 2'-O-alkyl (C1-3 alkyl, such as 2' OMe or 2'OEt), 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) substitutions.

In certain embodiments, the oligonucleotide contains at least one 2'-halo modification (e.g., in place of a 2' hydroxyl), such as 2'-fluoro, 2'-chloro, 2'-bromo, and 2'-iodo. In some embodiments, the 2' halo modification is fluoro. The oligonucleotide may contain from 1 to about 5 2'-halo modifications (e.g., fluoro), or from 1 to about 3 2'-halo modifications (e.g., fluoro). In some embodiments, the oligonucleotide contains all 2'-fluoro nucleotides at non-locked positions, or 2'-fluoro on all non-locked pyrimidine nucleotides. In certain embodiments, the 2'-fluoro groups are independently di-, tri-, or un-methylated.

The oligonucleotide may have one or more 2'-deoxy modifications (e.g., H for 2' hydroxyl), and in some embodiments, contains from 2 to about 10 2'-deoxy modifications at non-locked positions, or contains 2'deoxy at all non-locked positions.

In exemplary embodiments, the oligonucleotide contains 2' positions modified as 2'OMe in non-locked positions. Alternatively, non-locked purine nucleotides can be modified at the 2' position as 2'OMe, with non-locked pyrimidine nucleotides modified at the 2' position as 2'-fluoro.

In certain embodiments, the oligonucleotide further comprises at least one terminal modification or "cap." The cap may be a 5' and/or a 3'-cap structure. The terms "cap" or "end-cap" include chemical modifications at either terminus of the oligonucleotide (with respect to terminal ribonucleotides), and includes modifications at the linkage between the last two nucleotides on the 5' end and the last two nucleotides on the 3' end. The cap structure as described herein may increase resistance of the oligonucleotide to exonucleases without compromising molecular interactions with the miRNA target (i.e. miR-92) or cellular machinery. Such modifications may be selected on the basis of their increased potency in vitro or in vivo. The cap can be present at the 5'-terminus (5'-cap) or at the 3'-terminus (3'-cap) or can be present on both ends. In certain embodiments, the 5'- and/or 3'-cap is independently selected from phosphorothioate monophosphate, abasic residue (moiety), phosphorothioate linkage, 4'-thio nucleotide, carbocyclic nucleotide, phosphorodithioate linkage, inverted nucleotide or inverted abasic moiety (2'-3' or 3'-3'), phosphorodithioate monophosphate, and methylphosphonate moiety. The phosphorothioate or phosphorodithioate linkage(s), when part of a cap structure, are generally positioned between the two terminal nucleotides on the 5' end and the two terminal nucleotides on the 3' end.

In certain embodiments, the oligonucleotide has at least one terminal phosphorothioate monophosphate. The phosphorothioate monophosphate may support a higher potency by inhibiting the action of exonucleases. The phosphorothioate monophosphate may be at the 5' and/or 3' end of the oligonucleotide. A phosphorothioate monophosphate is defined by the following structures, where B is base, and R is a 2' modification as described above:

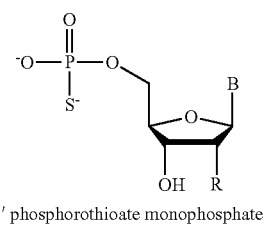

5' phosphorothioate monophosphate

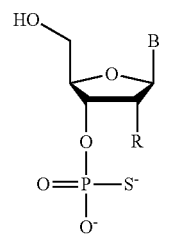

3' phosphorothioate monophosphate

Where the cap structure can support the chemistry of a locked nucleotide, the cap structure may incorporate a LNA as described herein.

Phosphorothioate linkages may be present in some embodiments, such as between the last two nucleotides on the 5' and the 3' end (e.g., as part of a cap structure), or as alternating with phosphodiester bonds. In these or other embodiments, the oligonucleotide may contain at least one terminal abasic residue at either or both the 5' and 3' ends. An abasic moiety does not contain a commonly recognized purine or pyrimidine nucleotide base, such as adenosine, guanine, cytosine, uracil or thymine. Thus, such abasic moieties lack a nucleotide base or have other non-nucleotide base chemical groups at the 1' position. For example, the abasic nucleotide may be a reverse abasic nucleotide, e.g., where a reverse abasic phosphoramidite is coupled via a 5' amidite (instead of 3' amidite) resulting in a 5'-5' phosphate bond. The structure of a reverse abasic nucleoside for the 5' and the 3' end of a polynucleotide is shown below.

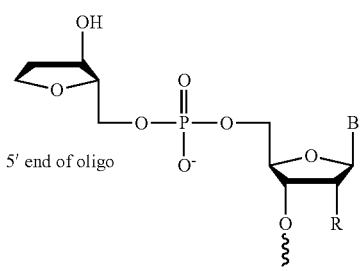

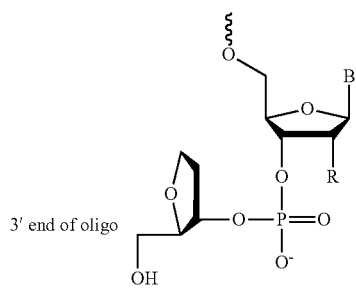

The oligonucleotide may contain one or more phosphorothioate linkages. Phosphorothioate linkages can be used to render oligonucleotides more resistant to nuclease cleavage. For example, the polynucleotide may be partially phosphorothioate-linked, for example, phosphorothioate linkages may alternate with phosphodiester linkages. In certain embodiments, however, the oligonucleotide is fully phosphorothioate-linked. In other embodiments, the oligonucleotide has from one to five or one to three phosphate linkages.

In some embodiments, the nucleotide has one or more carboxamido-modified bases as described in PCT/US11/59588, which is hereby incorporated by reference, including with respect to all exemplary pyrimidine carboxamido modifications disclosed therein with heterocyclic substituents.

The synthesis of oligonucleotides, including modified polynucleotides, by solid phase synthesis is well known and is reviewed in Caruthers et al., Nucleic Acids Symp. Ser. 7:215-23 (1980).

In some embodiments, the oligonucleotide comprises a sequence selected from Tables 1 and 2, in which "+" or "1" indicates the nucleotide is a LNA; "d" indicates the nucleotide is a DNA; "s" indicates a phosphorothioate linkage between the two nucleotides; and "mdC" indicates the nucleotide is a 5-methyl cytosine DNA:

TABLE 1

MiR-92 Inhibitors

| SEQ ID NO. | Alias | Sequence (5' to 3') (second line of sequence is with linkages notation) |
|---|---|---|
| SEQ ID NO: 7 | 92a_LNA_16_PS | +CC+GGG+AC+AA+G+TG+C+AA+T<br>lCs;dCs;lGs;dGs;dGs;lAs;dCs;lAs;dAs;lGs;lTs;dGs;lCs;lAs;dAs;lT |
| SEQ ID NO: 8 | 92a_LNA_16_1 | +CCGG+G+AC+AA+G+TG+CA+A+T<br>lCs;dCs;dGs;dGs;lGs;lAs;dCs;lAs;dAs;lGs;lTs;dGs;lCs;dAs;lAs;lT |
| SEQ ID NO: 9 | 92a_LNA_16_4 | +CC+GGG+ACA+A+G+TG+C+AA+T<br>lCs;dCs;lGs;dGs;dGs;lAs;dCs;dAs;lAs;lGs;lTs;dGs;lCs;lAs;dAs;lT |

TABLE 2

Additional MiR-92 Inhibitors

| SEQ ID NO. | Alias | Sequence (5' to 3') (second line of sequence is with linkages notation) |
|---|---|---|
| SEQ ID NO: 10 | 92a_Tiny_LNA | lAs;lGs;lTs;lGs;lCs;lAs;lAs;lT;<br>+A+G+T+G+C+A+A+T |
| SEQ ID NO: 11 | 92a_LNA_16_2 | lCs;dCs;lGs;lGs;dGs;dAs;lCs;lAs;dAs;lGs;dTs;lGs;dCs;lAs;dAs;lT<br>+CC+G+GGA+C+AA+GT+GC+AA+T |
| SEQ ID NO: 12 | 92a_LNA_16_3 | lCs;dCs;dGs;lGs;lGs;dAs;lCs;dAs;lAs;dAs;lGs;dTs;lGs;dCs;lAs;dAs;lT<br>+CCG+G+GA+CA+A+GT+GC+AA+T |
| SEQ ID NO: 13 | 92a_LNA_16_5 | lCs;dCs;lGs;dGs;lGs;dAs;lCs;dAs;lAs;dGs;lTs;dGs;lCs;dAs;lAs;lT<br>+CC+GG+GA+CA+AG+TG+CA+A+T |
| SEQ ID NO: 14 | 92a_LNA_16_6 | lCs;lCs;dGs;lGs;dGs;lAs;dCs;lAs;dAs;lAs;dTs;lGs;dCs;lAs;dAs;lT<br>+C+CG+GG+AC+AA+GT+GC+AA+T |
| SEQ ID NO: 15 | 92a_LNA-16_7 | lCs;dCs;dGs;dGs;lGs;dAs;lCs;dAs;lAs;dAs;lTs;lGs;dCs;lAs;lAs;lT<br>+CCGG+GAC+AAG+T+G+C+A+A+T |
| SEQ ID NO: 16 | 92a_LNA_16_8 | lCs;dCs;dGs;lGs;lGs;lAs;dCs;lAs;dAs;lAs;lTs;dGs;lCs;lAs;dAs:lT<br>+CCG+GG+AC+AA+G+TG+C+AA+T |
| SEQ ID NO: 17 | 92a_LNA_16_9 | lCs;dCs;lGs;dGs;lGs;dAs;lCs;lAs;dAs;lAs;dTs;lGs;dCs;lAs;dAs;lT<br>+CC+GG+GAC+AA+GT+G+C+AA+T |
| SEQ ID NO: 18 | 92a_LNA_16_10 | lCs;dCs;lGs;dGs;dGs;lAs;dCs;lAs;dAs;lAs;lTs;dGs;lCs;lAs;dAs;lT<br>+CC+GGG+AC+AA+G+TGC+A+A+T |
| SEQ ID NO: 19 | 92a_LNA_16_11 | lCs;lCs;lGs;dGs;dGs;lAs;dCs;lAs;dAs;lAs;dGs;lTs;dCs;lAs;lAs;lT<br>+C+C+GGG+AC+AAG+TGC+A+A+T |
| SEQ ID NO: 20 | 92a_LNA_16_12 | lCs;lCs;lGs;dGs;dGs;dAs;lCs;dAs;lAs;dAs;lGs;dTs;lGs;dCs;lAs;lAs;lT<br>+C+C+GG+GAC+AAG+TGC+A+A+T |
| SEQ ID NO: 21 | 92a_LNA_16_13 | lCs;lCs;lGs;dGs;dGs;lAs;dCs;lAs;dAs;lAs;dTs;lGs;lCs;lAs;dAs;lT<br>+C+C+GGG+AC+AAG+TG+C+AA+T |
| SEQ ID NO: 22 | 92a_LNA_16_14 | lCs;dCs;lGs;dGs;dGs;lAs;dCs;dAs;lAs;lAs;dGs;lTs;dGs;lCs;dAs;lAs;lT<br>+CC+GG+GA+CAA+G+TG+CA+A+T |
| SEQ ID NO: 23 | 92a_LNA_16_15 | lCs;lCs;dGs;dGs;lGs;dAs;lCs;dAs;lAs;lGs;dTs;lGs;dCs;dAs;dAs;lT<br>+C+CGG+GA+CA+A+GT+G+CAA+T |
| SEQ ID NO: 24 | 92a_LNA_16_16 | lCs;dCs;lGs;dGs;dGs;lAs;dCs;lAs;lAs;dGs;lTs;dGs;lCs;lAs;dAs;lT<br>+CC+GGG+AC+A+AG+TG+C+AA+T |
| SEQ ID NO: 25 | 92a_LNA_16_17 | lCs;dCs;lGs;dGs;dGs;lAs;dCs;lAs;dAs;lAs;dTs;lGs;dCs;lAs;lAs;lT<br>+CC+GGG+AC+AA+GT+G+C+AA+T |
| SEQ ID NO: 26 | 92a_LNA_16_18 | lCs;dCs;lGs;dGs;lGs;dAs;lCs;dAs;dAs;lGs;lTs;dGs;lCs;lAs;dAs;lT<br>+CC+GG+GA+CAA+G+TGC+A+A+T |

TABLE 2-continued

Additional MiR-92 Inhibitors

| SEQ ID NO. | Alias | Sequence (5' to 3') (second line of sequence is with linkages notation) |
|---|---|---|
| SEQ ID NO: 27 | 92a_LNA_16_19 | lCs;dCs;lGs;dGs;dGs;lAs;dCs;lAs;dAs;dGs;lTs;dGs;lCs;lAs;lAs;lT<br>+CC+GGG+AC+AAG+TG+C+A+A+T |
| SEQ ID NO: 28 | 92a_LNA_16_20 | lCs;dCs;lGs;dGs;lGs;dAs;dCs;lAs;dAs;lGs;lTs;dGs;lCs;lAs;dAs;lT<br>+CC+GG+GAC+AA+G+TG+C+AA+T |
| SEQ ID NO: 29 | 92a_LNA_16_21 | lCs;lCs;dGs;dGs;lGs;dAs;lCs;lAs;dAs;lGs;dTs;dGs;lCs;dAs;lAs;lT<br>+C+CGG+GA+C+AA+GTG+CA+A+T |
| SEQ ID NO: 30 | 92a_LNA_16_22 | lCs;dCs;lGs;lGs;dGs;dAs;lCs;dAs;lAs;lGs;dTs;lGs;dCs;lAs;dAs;lT<br>+CC+G+GGA+CA+A+GT+GC+AA+T |
| SEQ ID NO: 31 | 92a_LNA_16_23 | lCs;dCs;dGs;dGs;lGs;lAs;lCs;dAs;dAs;lGs;lTs;dGs;lCs;dAs;lAs;lT<br>+CCGG+G+A+CAA+G+TG+CA+A+T |
| SEQ ID NO: 32 | 92a_LNA_16_24 | lCs;dCs;dGs;lGs;lGs;dAs;lCs;dAs;dAs;lGs;dTs;lGs;lCs;lAs;dAs;lT<br>+CCG+G+GA+CAA+GT+G+C+AA+T |
| SEQ ID NO: 33 | 92a_LNA_16_25 | lCs;dCs;dGs;lGs;lGs;dAs;lCs;dAs;dAs;lGs;dTs;lGs;lCs;lAs;dAs;lT<br>+CCG+G+GA+C+AA+GT+GC+AA+T |
| SEQ ID NO: 34 | 92a_LNA_15_1 | lCs:dGs:dGs:dGs:lAs:dCs:lAs:dAs:lGs:lTs:dGs:lCs:lAs:dAs:lT<br>+CGGG+AC+AA+G+TG+C+AA+T |
| SEQ ID NO: 35 | 92a_LNA_15_2 | lCs;dGs;dGs;dGs;lAs;dCs;lAs;dAs;lGs;lTs;dGs;lCs;dAs;lAs;lT<br>+CGGG+AC+AA+G+TG+CA+A+T |
| SEQ ID NO: 36 | 92a_LNA_15_3 | lCs:dGs;lGs;dGs;dAs;lCs;lAs;dAs;lGs;dTs;lGs;dCs;lAs;dAs;lT<br>+CG+GGA+C+AA+GT+GC+AA+T |
| SEQ ID NO: 37 | 92a_LNA_15_4 | lCs:dGs;dGs;lGs;dAs;lCs;dAs;lAs;lGs;dTs;lGs;dCs;lAs;dAs;lT<br>+CGG+GA+CA+A+GT+GC+AA+T |
| SEQ ID NO: 38 | 92a_LNA_15_5 | lCs;dGs;dGs;dGs;lAs;dCs;dAs;lAs;lGs;lTs;dGs;lCs;lAs;dAs;lT<br>+CGGG+ACA+A+G+TG+C+AA+T |
| SEQ ID NO: 39 | 92a_LNA_15_6 | lCs;lGs;dGs;lGs;dAs;lCs;dAs;lAs;dGs;lTs;dGs;lCs;dAs;dAs;lT<br>+C+GG+GA+CA+AG+TG+CAA+T |
| SEQ ID NO: 40 | 92a_LNA_15_7 | lCs;dGs;lGs;dGs;lAs;dCs;lAs;lAs;lGs;dTs;lGs;dCs;lAs;dAs;lT<br>+CG+GG+AC+AA+GT+GC+AA+T |
| SEQ ID NO: 41 | 92a_LNA_15_8 | lCs;dGs;dGs;lGs;dAs;dCs;lAs;dAs;lGs;dTs;lGs;lCs;lAs;lAs;lT<br>+CGG+GAC+AAGT+G+C+A+A+T |
| SEQ ID NO: 42 | 92a_LNA_15_9 | lCs;lGs;dGs;dGs;lAs;dCs;lAs;dAs;lGs;dTs;dGs;lCs;lAs;lAs;lT<br>+C+GGG+AC+AA+GTGC+A+A+T |
| SEQ ID NO: 43 | 92a_LNA_15_10 | lCs;lGs;dGs;dGs;lAs;dCs;lAs;dAs;dGs;lTs;dGs;lCs;lAs;lAs;lT<br>+C+GGG+AC+AAG+TGC+A+A+T |
| SEQ ID NO: 44 | 92a_LNA_15_11 | lCs;lGs;dGs;lGs;dAs;dCs;lAs;dAs;dGs;lTs;dGs;lCs;lAs;lAs;lT<br>+C+GG+GAC+AAG+TGC+A+A+T |
| SEQ ID NO: 45 | 92a_LNA_15_12 | lCs;lGs;dGs;dGs;lAs;dCs;lAs;dAs;lGs;lTs;dGs;lCs;lAs;dAs;lT<br>+C+GGG+AC+AAG+TG+C+AA+T |
| SEQ ID NO: 46 | 92a_LNA_15_13 | lCs;lGs;dGs;lGs;dAs;lCs;dAs;dAs;lGs;dTs;dGs;lCs;dAs;lAs;lT<br>+C+GG+GA+CAA+GTG+CA+A+T |
| SEQ ID NO: 47 | 92a_LNA_15_14 | lCs;dGs;dGs;lGs;dAs;lCs;dAs;lAs;lGs;dTs;lGs;dCs;lAs;dAs;lT<br>+CGG+GA+CA+A+GT+G+CAA+T |
| SEQ ID NO: 48 | 92a_LNA_15_15 | lCs;lGs;dGs;dGs;lAs;dCs;dAs;lAs;lGs;lTs;dGs;lCs;lAs;dAs;lT<br>+C+GGG+ACA+AG+TG+C+AA+T |
| SEQ ID NO: 49 | 92a_LNA_15_16 | lCs;lGs;dGs;dGs;lAs;dCs;lAs;lAs;lGs;dTs;lGs;dCs;lAs;dAs;lT<br>+C+GGG+AC+AA+GT+GC+AA+T |
| SEQ ID NO: 50 | 92a_LNA_15_17 | lCs;lGs;dGs;dGs;dAs;lCs;dAs;lAs;lGs;lTs;dGs;lCs;lAs;lAs;lT<br>+C+GGGA+CAA+G+TGC+A+A+T |
| SEQ ID NO: 51 | 92a_LNA_15_18 | lCs;lGs;dGs;dGs;lAs;dCs;lAs;dAs;dGs;lTs;dGs;lCs;dAs;lAs;lT<br>+C+GGG+AC+AAG+TG+CA+A+T |

TABLE 2-continued

Additional MiR-92 Inhibitors

| SEQ ID NO. | Alias | Sequence (5' to 3') (second line of sequence is with linkages notation) |
|---|---|---|
| SEQ ID NO: 52 | 92a_LNA_15_19 | lCs;lGs;dGs;lGs;dAs;dCs;lAs;dAs;lGs;dTs;dGs;lCs;lAs;dAs;lT<br>+C+GG+GAC+AA+GTG+C+AA+T |
| SEQ ID NO: 53 | 92a_LNA_15_20 | lCs;dGs;dGs;lGs;dAs;lCs;lAs;dAs;lGs;dTs;dGs;lCs;dAs;lAs;lT<br>+CGG+GA+C+AA+GTG+CA+A+T |
| SEQ ID NO: 54 | 92a_LNA_15_21 | lCs;dGs;lGs;dGs;dAs;lCs;dAs;lAs;lGs;dTs;lGs;dCs;lAs;dAs;lT<br>+CG+GGA+CA+A+GT+GC+AA+T |
| SEQ ID NO: 55 | 92a_LNA_15_22 | lCs:dGs:dGs:lGs:lAs:lCs:dAs:dAs:lGs:dTs:dGs:lCs:dAs:lAs:lT<br>+CGG+G+A+CAA+GTG+CA+A+T |
| SEQ ID NO: 56 | 92a_LNA_15_23 | lCs;dGs;dGs;lGs;dAs;lCs;dAs;dAs;lGs;dTs;lGs;lCs;lAs;dAs;lT<br>+CGG+GA+CAA+GT+G+C+AA+T |
| SEQ ID NO: 57 | 92a_LNA_15_24 | lCs:dGs:dGs:lGs:dAs:lCs:lAs:dAs:lGs:dTs:lGs:dCs:lAs:dAs:lT<br>+CGG+GA+C+AA+GT+GC+AA+T |
| SEQ ID NO: 58 | | lCs;dCs;lGs;lGs;lGs;lAs;dCs;lAs;dAs;lGs;dTs;dGs;lCs;dAs;dAs;lT<br>+CC+G+G+G+AC+AA+GTG+CAA+T |
| SEQ ID NO: 59 | | lCs;dCs;lGs;lGs;dGs;lAs;dCs;lAs;lAs;lGs;dTs;dGs;lCs;dAs;lAs;dT<br>+CC+G+GG+AC+A+A+GTG+CA+AT |
| SEQ ID NO: 60 | | lCs;dCs;lGs;lGs;lGs;lAs;dCs;lAs;dAs;lGs;dTs;dGs;lCs;dAs;lAs;dT<br>+CC+G+G+G+AC+AA+GTG+CA+AT |
| SEQ ID NO: 61 | | lCs;dCs;dGs;dGs;lGs;lAs;dCs;lAs;lAs;lGs;lTs;dGs;lCs;dAs;lAs;lT<br>+CCGG+G+ACA+A+G+TG+CA+A+T |
| SEQ ID NO: 62 | | lCs;dCs;dGs;dGs;lGs;lAs;dCs;lAs;dAs;lGs;lTs;dGs;lCs;lAs;dAs;lT<br>+CCGG+G+AC+AA+G+TG+C+AA+T |
| SEQ ID NO: 63 | | lCs;mdCs;dGs;dGs;lGs;lAs;dCs;lAs;dAs;lGs;lTs;dGs;lCs;dAs;lAs;lT<br>+CCGG+G+AC+AA+G+TG+CA+A+T |
| SEQ ID NO: 64 | | lCs;mdCs;lGs;dGs;dGs;lAs;dCs;dAs;lAs;lGs;lTs;dGs;lCs;lAs;dAs;lT<br>+CC+GGG+ACA+A+G+TG+C+AA+T |
| SEQ ID NO: 65 | | lCs;mdCs;lGs;dGs;dGs;lAs;dCs;lAs;dAs;lG0Ts;dGs;lCs;lAs;dAs;lT<br>+CC+GGG+AC+AA+G+TG+C+AA+T |
| SEQ ID NO: 66 | 92a_LNA_14_1 | lGs;dGs;dGs;lAs;dCs;lAs;dAs;lGs;lTs;dGs;lCs;lAs;dAs;lT<br>+GGG+AC+AA+G+TG+C+AA+T |
| SEQ ID NO: 67 | 92a_LNA_14_2 | lGs;dGs;dGs;lAs;dCs;lAs;dAs;lGs;lTs;dGs;lCs;dAs;lAs;lT<br>+GGG+AC+AA+G+TG+CA+A+T |
| SEQ ID NO: 68 | 92a_LNA_14_3 | lGs;lGs;dGs;dAs;lCs;lAs;dAs;lGs;dTs;lGs;dCs;lAs;dAs;lT<br>+G+GGA+C+AA+GT+GC+AA+T |
| SEQ ID NO: 69 | 92a_LNA_14_4 | lGs;dGs;lGs;dAs;lCs;dAs;lAs;lGs;dTs;dCs;dAs;lAs;lT<br>+GG+GA+CA+A+GT+GC+AA+T |
| SEQ ID NO: 70 | 92a_LNA_14_5 | lGs;dGs;dGs;lAs;dCs;dAs;lAs;lGs;lTs;dGs;lCs;lAs;dAs;lT<br>+GGG+ACA+A+G+TG+C+AA+T |
| SEQ ID NO: 71 | 92a_LNA_14_6 | lGs;dGs;lGs;dAs;lCs;dAs;lAs;dGs;lTs;dGs;lCs;dAs;dAs;lT<br>+GG+GA+CA+AG+TG+CAA+T |
| SEQ ID NO: 72 | 92a_LNA_14_7 | lGs;lGs;dGs;lAs;dCs;lAs;dAs;lGs;dTs;lGs;dCs;lAs;dAs;lT<br>+G+GG+AC+AA+GT+GC+AA+T |
| SEQ ID NO: 73 | 92a_LNA_14_8 | lGs;dGs;lGs;dAs;dCs;lAs;dGs;dTs;lGs;lCs;lAs;lAs;lT<br>+GG+GAC+AAGT+G+C+A+A+T |
| SEQ ID NO: 74 | 92a_LNA_14_9 | lGs;dGs;dGs;lAs;dCs;lAs;dAs;lGs;dTs;dCs;lAs;lAs;lT<br>+GGG+AC+AA+GTGC+A+A+T |
| SEQ ID NO: 75 | 92a_LNA_14_10 | lGs;dGs;dGs;lAs;dCs;lAs;dAs;dGs;lTs;dGs;dCs;lAs;lAs;lT<br>+GGG+AC+AAG+TGC+A+A+T |
| SEQ ID NO: 76 | 92a_LNA_14_11 | lGs;dGs;lGs;dAs;dCs;lAs;dAs;dGs;lTs;dGs;dCs;lAs;lAs;lT<br>+GG+GAC+AAG+TGC+A+A+T |

TABLE 2-continued

Additional MiR-92 Inhibitors

| SEQ ID NO. | Alias | Sequence (5' to 3') (second line of sequence is with linkages notation) |
|---|---|---|
| SEQ ID NO: 77 | 92a_LNA_14_12 | lGs;dGs;dGs;lAs;dCs;lAs;dAs;dGs;lTs;dGs;lCs;lAs;dAs;lT<br>+GGG+AC+AAG+TG+C+AA+T |
| SEQ ID NO: 78 | 92a_LNA_14_13 | lGs;dGs;lGs;dAs;lCs;dAs;dAs;lGs;dTs;dGs;lCs;lAs;dAs;lT<br>+GG+GA+CAA+GTG+CA+A+T |
| SEQ ID NO: 79 | 92a_LNA_14_14 | lGs;dGs;lGs;dAs;lCs;dAs;lAs;lGs;dTs;lGs;lCs;dAs;dAs;lT<br>+GG+GA+CA+A+GT+G+CAA+T |
| SEQ ID NO: 80 | 92a_LNA_14_15 | lGs;dGs;dGs;lAs;dCs;dAs;lAs;dGs;lTs;dGs;lCs;lAs;dAs;lT<br>+GGG+ACA+AG+TG+C+AA+T |
| SEQ ID NO: 81 | 92a_LNA_14_16 | lGs;dGs;dGs;lAs;dCs;lAs;dAs;lGs;dTs;lGs;dCs;lAs;dAs;lT<br>+GGG+AC+AA+GT+GC+AA+T |
| SEQ ID NO: 82 | 92a_LNA_14_17 | lGs;dGs;dGs;dAs;lCs;dAs;dAs;lGs;lTs;dGs;dCs;lAs;lAs;lT<br>+GGGA+CAA+G+TGC+A+A+T |
| SEQ ID NO: 83 | 92a_LNA_14_18 | lGs;dGs;dGs;lAs;dCs;lAs;dAs;dGs;lTs;dGs;lCs;lAs;lAs;lT<br>+GGG+AC+AAG+TG+CA+A+T |
| SEQ ID NO: 84 | 92a_LNA_14_19 | lGs;dGs;lGs;dAs;dCs;lAs;dAs;lGs;dTs;dGs;lCs;lAs;dAs;lT<br>+GG+GAC+AA+GTG+C+AA+T |
| SEQ ID NO: 85 | 92a_LNA_14_20 | lGs;dGs;lGs;dAs;lCs;lAs;dAs;lGs;dTs;lGs;lCs;lAs;lAs;lT<br>+GG+GA+C+AA+GTG+CA+A+T |
| SEQ ID NO: 86 | 92a_LNA_14_21 | lGs;lGs;dGs;dAs;lCs;dAs;lAs;lGs;dTs;lGs;dCs;lAs;dAs;lT<br>+G+GGA+CA+A+GT+GC+AA+T |
| SEQ ID NO: 87 | 92a_LNA_14_22 | lGs;dGs;lGs;lAs;lCs;dAs;lAs;dGs;dTs;dGs;lCs;lAs;dAs;lT<br>+GG+G+A+CAA+GTG+CA+A+T |
| SEQ ID NO: 88 | 92a_LNA_14_23 | lGs;dGs;lGs;dAs;lCs;dAs;dAs;lGs;dTs;lGs;lCs;lAs;dAs;lT<br>+GG+GA+CAA+GT+G+C+AA+T |
| SEQ ID NO: 89 | 92a_LNA_14_24 | lGs;dGs;lGs;dAs;lCs;lAs;dAs;lGs;dTs;lGs;dCs;lAs;dAs;lT<br>+GG+GA+C+AA+GT+GC+AA+T |
| SEQ ID NO: 90 | 92a_LNA_13_1 | lGs;dGs;lAs;dCs;lAs;dAs;lGs;lTs;dGs;lCs;lAs;dAs;lT<br>+GG+AC+AA+G+TG+C+AA+T |
| SEQ ID NO: 91 | 92a_LNA_13_2 | lGs;dGs;lAs;dCs;lAs;dAs;lGs;lTs;dGs;dAs;lAs;lT<br>+GG+AC+AA+G+TG+CA+A+T |
| SEQ ID NO: 92 | 92a_LNA_13_3 | lGs;dGs;dAs;lCs;lAs;dAs;lGs;dTs;lGs;dCs;lAs;dAs;lT<br>+GGA+C+AA+GT+GC+AA+T |
| SEQ ID NO: 93 | 92a_LNA_13_4 | lGs;lGs;dAs;lCs;dAs;lAs;lGs;dTs;lGs;dCs;lAs;dAs;lT<br>+G+GA+CA+A+GT+GC+AA+T |
| SEQ ID NO: 94 | 92a_LNA_13_5 | lGs;dGs;lAs;dCs;dAs;lAs;lGs;lTs;dGs;lCs;lAs;dAs;lT<br>+GG+ACA+A+G+TG+C+AA+T |
| SEQ ID NO: 95 | 92a_LNA_13_6 | lGs;lGs;dAs;lCs;dAs;lAs;dGs;lTs;dGs;lCs;dAs;dAs;lT<br>+G+GA+CA+AG+TG+CAA+T |
| SEQ ID NO: 96 | 92a_LNA_13_7 | lGs;dGs;lAs;dCs;lAs;dAs;lGs;dTs;lGs;lCs;lAs;dAs;lT<br>+GG+AC+AA+GT+GC+AA+T |
| SEQ ID NO: 97 | 92a_LNA_13_8 | lGs;lGs;dAs;dCs;lAs;dAs;dGs;dTs;lGs;lCs;lAs;lAs;lT<br>+G+GAC+AAGT+G+C+A+A+T |
| SEQ ID NO: 98 | 92a_LNA_13_9 | lGs;dGs;lAs;dCs;lAs;dAs;dTs;dGs;dCs;lAs;lAs;lT<br>+GG+AC+AA+GTGC+A+A+T |
| SEQ ID NO: 99 | 92a_LNA_13_10 | lGs;dGs;lAs;dCs;dAs;dAs;lTs;dGs;lCs;lAs;dAs;lT<br>+GG+AC+AAG+TGC+A+A+T |
| SEQ ID NO: 100 | 92a_LNA_13_11 | lGs;lGs;dAs;dCs;lAs;dAs;dGs;lTs;dGs;dCs;lAs;lAs;lT<br>+G+GAC+AAG+TGC+A+A+T |
| SEQ ID NO: 101 | 92a_LNA_13_12 | lGs;dGs;lAs;dCs;lAs;dAs;dGs;lTs;dGs;lCs;lAs;dAs;lT<br>+GG+AC+AAG+TG+C+AA+T |

TABLE 2-continued

Additional MiR-92 Inhibitors

| SEQ ID NO. | Alias | Sequence (5' to 3') (second line of sequence is with linkages notation) |
|---|---|---|
| SEQ ID NO: 102 | 92a_LNA_13_13 | lGs;lGs;dAs;lCs;dAs;dAs;lGs;dTs;dGs;lCs;dAs;lAs;lT<br>+G+GA+CAA+GTG+CA+A+T |
| SEQ ID NO: 103 | 92a_LNA_13_14 | lGs;lGs;dAs;lCs;dAs;lAs;lGs;dTs;lGs;lCs;dAs;dAs;lT<br>+G+GA+CA+A+GT+G+CAA+T |
| SEQ ID NO: 104 | 92a_LNA_13_15 | lGs;dGs;lAs;dCs;dAs;lAs;dGs;lTs;dGs;lCs;lAs;dAs;lT<br>+GG+ACA+AG+TG+C+AA+T |
| SEQ ID NO: 105 | 92a_LNA_13_16 | lGs;dGs;lAs;dCs;lAs;dAs;lGs;dTs;lGs;dCs;lAs;dAs;lT<br>+GG+AC+AA+GT+GC+AA+T |
| SEQ ID NO: 106 | 92a_LNA_13_17 | lGs;dGs;dAs;lCs;dAs;dAs;lGs;lTs;dGs;dCs;lAs;lAs;lT<br>+GGA+CAA+G+TGC+A+A+T |
| SEQ ID NO: 107 | 92a_LNA_13_18 | lGs;dGs;lAs;dCs;lAs;dAs;dGs;lTs;dGs;lCs;dAs;lAs;lT<br>+GG+AC+AAG+TG+CA+A+T |
| SEQ ID NO: 108 | 92a_LNA_13_19 | lGs;lGs;dAs;dCs;lAs;dAs;lGs;dTs;dGs;lCs;lAs;dAs;lT<br>+G+GAC+AA+GTG+C+AA+T |
| SEQ ID NO: 109 | 92a_LNA_13_20 | lGs;lGs;dAs;lCs;lAs;dAs;lGs;dTs;dGs;lCs;dAs;lAs;lT<br>+G+GA+C+AA+GTG+CA+A+T |
| SEQ ID NO: 110 | 92a_LNA_13_21 | lGs;dGs;dAs;lCs;dAs;lAs;lGs;dTs;lGs;dCs;lAs;dAs;lT<br>+GGA+CA+A+GT+GC+AA+T |
| SEQ ID NO: 111 | 92a_LNA_13_22 | lGs;lGs;lAs;lCs;dAs;dAs;lGs;dTs;dGs;lCs;dAs;lAs;lT<br>+G+G+A+CAA+GTG+CA+A+T |
| SEQ ID NO: 112 | 92a_LNA_13_23 | lGs;lGs;dAs;lCs;dAs;dAs;lGs;dTs;lGs;lCs;lAs;dAs;lT<br>+G+GA+CAA+GT+G+C+AA+T |
| SEQ ID NO: 113 | 92a_LNA_13_24 | lGs;lGs;dAs;lCs;lAs;dAs;lGs;dTs;lGs;dCs;lAs;dAs;lT<br>+G+GA+C+AA+GT+GC+AA+T |
| SEQ ID NO: 114 | 92a_LNA_12_1 | lGs;lAs;dCs;lAs;dAs;lGs;lTs;dGs;lCs;lAs;dAs;lT<br>+G+AC+AA+G+TG+C+AA+T |
| SEQ ID NO: 115 | 92a_LNA_12_2 | lGs;lAs;dCs;lAs;dAs;lGs;lTs;dGs;lCs;dAs;lAs;lT<br>+G+AC+AA+G+TG+CA+A+T |
| SEQ ID NO: 116 | 92a_LNA_12_3 | lGs;dAs;lCs;lAs;dAs;lGs;dTs;lGs;dCs;lAs;dAs;lT<br>+GA+C+AA+GT+GC+AA+T |
| SEQ ID NO: 117 | 92a_LNA_12_4 | lGs;dAs;lCs;dAs;lAs;lGs;dTs;lGs;dCs;lAs;dAs;lT<br>+GA+CA+A+GT+GC+AA+T |
| SEQ ID NO: 118 | 92a_LNA_12_5 | lGs;lAs;dCs;dAs;lAs;lGs;lTs;dGs;lCs;lAs;dAs;lT<br>+G+ACA+A+G+TG+C+AA+T |
| SEQ ID NO: 119 | 92a_LNA_12_6 | lGs;dAs;lCs;dAs;lAs;dGs;lTs;dGs;lCs;dAs;dAs;lT<br>+GA+CA+AG+TG+CAA+T |
| SEQ ID NO: 120 | 92a_LNA_12_7 | lGs;lAs;dCs;lAs;dAs;lGs;dTs;lGs;dCs;dAs;lAs;lT<br>+G+AC+AA+GT+GC+AA+T |
| SEQ ID NO: 121 | 92a_LNA_12_8 | lGs;dAs;dCs;lAs;dAs;dGs;dTs;lGs;lCs;lAs;lAs;lT<br>+GAC+AAGT+G+C+A+A+T |
| SEQ ID NO: 122 | 92a_LNA_12_9 | lGs;lAs;dCs;lAs;dAs;lGs;dTs;dGs;dCs;lAs;lAs;lT<br>+G+AC+AA+GTGC+A+A+T |
| SEQ ID NO: 123 | 92a_LNA_12_10 | lGs;lAs;dCs;lAs;dGs;lTs;dGs;dCs;lAs;lAs;lT<br>+G+AC+AAG+TGC+A+A+T |
| SEQ ID NO: 124 | 92a_LNA_12_11 | lGs;dAs;dCs;lAs;dGs;lTs;dGs;dCs;lAs;lAs;lT<br>+GAC+AAG+TGC+A+A+T |
| SEQ ID NO: 125 | 92a_LNA_12_12 | lGs;lAs;dCs;lAs;dAs;dGs;lTs;dGs;lCs;lAs;dAs;lT<br>+G+AC+AAG+TG+C+AA+T |
| SEQ ID NO: 126 | 92a_LNA_12_13 | lGs;dAs;lCs;dAs;dAs;lGs;dTs;dGs;lCs;dAs;lAs;lT<br>+GA+CAA+GTG+CA+A+T |

TABLE 2-continued

Additional MiR-92 Inhibitors

| SEQ ID NO. | Alias | Sequence (5' to 3') (second line of sequence is with linkages notation) |
|---|---|---|
| SEQ ID NO: 127 | 92a_LNA_12_14 | lGs;dAs;lCs;dAs;lAs;lGs;dTs;lGs;lCs;dAs;dAs;lT<br>+GA+CA+A+GT+G+CAA+T |
| SEQ ID NO: 128 | 92a_LNA_12_15 | lGs;lAs;dCs;dAs;lAs;dGs;lTs;dGs;lCs;lAs;dAs;lT<br>+G+ACA+AG+TG+C+AA+T |
| SEQ ID NO: 129 | 92a_LNA_12_16 | lGs;lAs;dCs;lAs;dAs;lGs;dTs;lGs;dCs;lAs;dAs;lT<br>+G+AC+AA+GT+GC+AA+T |
| SEQ ID NO: 130 | 92a_LNA_12_17 | lGs;dAs;lCs;dAs;dAs;lGs;lTs;dGs;dCs;lAs;lAs;lT<br>+GA+CAA+G+TGC+A+A+T |
| SEQ ID NO: 131 | 92a_LNA_12_18 | lGs;lAs;dCs;lAs;dAs;dGs;lTs;dGs;lCs;dAs;lAs;lT<br>+G+AC+AAG+TG+CA+A+T |
| SEQ ID NO: 132 | 92a_LNA_12_19 | lGs;dAs;dCs;lAs;dAs;lGs;dTs;dGs;lCs;lAs;dAs;lT<br>+GAC+AA+GTG+C+AA+T |
| SEQ ID NO: 133 | 92a_LNA_12_20 | lGs;dAs;lCs;lAs;dAs;lGs;dTs;dGs;lCs;lAs;lAs;lT<br>+GA+C+AA+GTG+CA+A+T |
| SEQ ID NO: 134 | 92a_LNA_12_21 | lGs;dAs;lCs;dAs;lAs;lGs;dTs;dGs;dCs;lAs;dAs;lT<br>+GA+CA+A+GT+GC+AA+T |
| SEQ ID NO: 135 | 92a_LNA_12_22 | lGs;lAs;lCs;dAs;lAs;lGs;dTs;dGs;lCs;lAs;dAs;lT<br>+G+A+CAA+GTG+CA+A+T |
| SEQ ID NO: 136 | 92a_LNA_12_23 | lGs;dAs;lCs;dAs;dAs;lGs;dTs;lGs;lCs;lAs;dAs;lT<br>+GA+CAA+GT+G+C+AA+T |
| SEQ ID NO: 137 | 92a_LNA_12_24 | lGs;dAs;lCs;lAs;dAs;lGs;dTs;lGs;dCs;lAs;dAs;lT<br>+GA+C+AA+GT+GC+AA+T |
| SEQ ID NO: 138 | | lCs;dCs;lGs;dGs;dGs;lAs;dCs;lAs;dAs;lGs;lTs;dGs;lC;lA;dA;lT<br>+CC+GGG+AC+AA+G+TG+C+AA+T |
| SEQ ID NO: 139 | | lCs;dCs;lGs;dGs;dGs;lAs;dCs;lAs;dAs;lGs;lTs;dG;lC;lA;dA;lT<br>+CC+GGG+AC+AA+G+TG+C+AA+T |
| SEQ ID NO: 140 | | lCs;dCs;lGs;dGs;dGs;lAs;dCs;lAs;dA;lG;lT;dG;lC;lA;dA;lT<br>+CC+GGG+AC+AA+G+TG+C+AA+T |
| SEQ ID NO: 141 | | lCs;dC;lGs;dG;dGs;lA;dCs;lA;dAs;lG;lTs;dG;lCs;lA;dAs;lT<br>+CC+GGG+AC+AA+G+TG+C+AA+T |
| SEQ ID NO: 142 | | lCs;dC;lG;dGs;dG;lA;dCs;lA;dA;lGs;lT;dG;lCs;lA;dA;lT<br>+CC+GGG+AC+AA+G+TG+C+AA+T |
| SEQ ID NO: 143 | | lC;dC;lG;dG;dG;lA;dC;lA;dA;lG;lT;dG;lC;lA;dA;lT<br>+CC+GGG+AC+AA+G+TG+C+AA+T |
| SEQ ID NO: 144 | | lCs;mdCs;lGs;dGs;dGs;lAs;dCs;lAs;dAs;lGs;lTs;dGs;lC;lA;dA;lT<br>+CC+GGG+AC+AA+G+TG+C+AA+T |
| SEQ ID NO: 145 | | lCs;mdCs;lGs;dGs;dGs;lAs;dCs;lAs;dAs;lGs;lTs;dG;lC;lA;dA;lT<br>+CC+GGG+AC+AA+G+TG+C+AA+T |
| SEQ ID NO: 146 | | lCs;mdCs;lGs;dGs;dGs;lAs;dCs;lAs;dA;lG;lT;dG;lC;lA;dA;lT<br>+CC+GGG+AC+AA+G+TG+C+AA+T |
| SEQ ID NO: 147 | | lCs;mdC;lGs;dG;dGs;lA;dCs;lA;dAs;lG;lTs;dG;lCs;lA;dAs;lT<br>+CC+GGG+AC+AA+G+TG+C+AA+T |
| SEQ ID NO: 148 | | lCs;mdC;lG;dGs;dG;lA;dCs;lA;dA;lGs;lT;dG;lCs;lA;dA;lT<br>+CC+GGG+AC+AA+G+TG+C+AA+T |
| SEQ ID NO: 149 | | lC;mdC;lG;dG;dG;lA;dC;lA;dA;lG;lT;dG;lC;lA;dA;lT<br>+CC+GGG+AC+AA+G+TG+C+AA+T |
| SEQ ID NO: 150 | | lCs.dmCs.dGs.dGs.lGs.lAs.dCs.lAs.dAs.lGs.lTs.dGs.lC.dA.lA.lT<br>+CCGG+G+AC+AA+G+TG+CA+A+T |
| SEQ ID NO: 151 | | lCs.dmCs.dGs.dGs.lGs.lAs.dCs.lAs.dAs.lGs.lTs.dG.lC.dA.lA.lT<br>+CCGG+G+AC+AA+G+TG+CA+A+T |

TABLE 2-continued

Additional MiR-92 Inhibitors

| SEQ ID NO. | Alias | Sequence (5' to 3') (second line of sequence is with linkages notation) |
|---|---|---|
| SEQ ID NO: 152 | | 1Cs.dmCs.dGs.dGs.1Gs.1As.dCs.1As.dA.1G.1T.dG.1C.dA.1A.1T<br>+CCGG+G+AC+AA+G+TG+CA+A+T |
| SEQ ID NO: 153 | | 1Cs.dmC.dGs.dG.1Gs.1A.dCs.1A.dAs.1G.1Ts.dG.1Cs.dA.1As.1T<br>+CCGG+G+AC+AA+G+TG+CA+A+T |
| SEQ ID NO: 154 | | 1Cs.dmC.dG.dGs.1G;1A.dCs.1A.dA.1Gs.1T.dG.1Cs.dA.1As.1T<br>+CCGG+G+AC+AA+G+TG+CA+A+T |
| SEQ ID NO: 155 | | 1C.dmC.dG.dG.1G.1A.dC.1A.dA.1G.1T.dG.1C.dA.1A.1T<br>+CCGG+G+AC+AA+G+TG+CA+A+T |
| SEQ ID NO: 156 | | 1Cs.dmCs.1Gs.dGs.dGs.1As.dCs.dAs.1As.1Gs.1Ts.dGs.1C.1A.dA.1T<br>+CC+GGG+ACA+A+G+TG+C+AA+T |
| SEQ ID NO: 157 | | 1Cs.dmCs.1Gs.dGs.dGs.1As.dCs.dAs.1As.1Gs.1Ts.dG.1C.1A.dA.1T<br>+CC+GGG+ACA+A+G+TG+C+AA+T |
| SEQ ID NO: 158 | | 1Cs.dmCs.1Gs.dGs.dGs.1As.dCs.dAs.1A.1G.1T.dG.1C.1A.dA.1T<br>+CC+GGG+ACA+A+G+TG+C+AA+T |
| SEQ ID NO: 159 | | 1Cs.dmC.1Gs.dG.dGs.1A.dCs.dA.1As.1G.1Ts.dG.1Cs.1A.dAs.1T<br>+CC+GGG+ACA+A+G+TG+C+AA+T |
| SEQ ID NO: 160 | | 1Cs.dmC.1G.dGs.dG.1A.dCs.dA.1A.1Gs.1T.dG.1Cs.1A.dA.1T<br>+CC+GGG+ACA+A+G+TG+C+AA+T |
| SEQ ID NO: 161 | | 1C.dmC.1G.dG.dG.1A.dC.dA.1A.1G.1T.dG.1C.1A.dA.1T<br>+CC+GGG+ACA+A+G+TG+C+AA+T |
| SEQ ID NO: 162 | | 1Cs;dCs;dGs;dGs;1Gs;1As;dCs;dAs;1As;1Gs;1Ts;dGs;1Cs;dAs;1As;1T<br>+CCGG+G+ACA+A+G+TG+CA+A+T |
| SEQ ID NO: 163 | | 1Cs;dCs;dGs;dGs;1Gs;1As;dCs;1As;dAs;1Gs;1Ts;dGs;1Cs;1As;dAs;1T<br>+CCGG+G+AC+AA+G+TG+C+AA+T |
| SEQ ID NO: 164 | | 1Cs;dCs;dGs;1Gs;1Gs;dAs;1Cs;dAs;1As;1Gs;dTs;1Gs;dCs;1As;dAs;1T<br>+CCG+G+GA+CA+A+GT+GC+AA+T |

In one embodiment, the oligonucleotide comprises a sequence selected from Tables 1 and 2, and comprises at least one non-locked nucleotide that is 2' O-alkyl or 2' halo modified. In some embodiments, the oligonucleotide comprises at least one LNA that has a 2' to 4' methylene bridge. In some embodiments, the oligonucleotide has a 5' cap structure, 3' cap structure, or 5' and 3' cap structure. In yet other embodiments, the oligonucleotide comprises a pendent lipophilic group.

The oligonucleotide may be incorporated within a variety of macromolecular assemblies or compositions. Such complexes for delivery may include a variety of liposomes, nanoparticles, and micelles, formulated for delivery to a patient. The complexes may include one or more fusogenic or lipophilic molecules to initiate cellular membrane penetration. Such molecules are described, for example, in U.S. Pat. Nos. 7,404,969 and 7,202,227, which are hereby incorporated by reference in their entireties. Alternatively, the oligonucleotide may further comprise a pendant lipophilic group to aid cellular delivery, such as those described in WO 2010/129672, which is hereby incorporated by reference.

The present invention also provides a method for delivering an oligonucleotide disclosed herein to a cell (e.g., as part of a composition or formulation described herein) for reducing or inhibiting activity or function of miR-92 in the cell. In one embodiment, the oligonucleotide comprises sequence at least partially complementary to miR-92. In one embodiment, the oligonucleotide is selected from Tables 1 or 2. In some embodiments, the cell is a mammalian cell. In some embodiments, the cell is a cardiac or muscle cell. In some embodiments, the cell is involved in wound healing. In some embodiments, the cell is a fibrocyte, fibroblast, keratinocyte or endothelial cell. In yet other embodiments, the cell is in vivo or ex vivo.

Also provided herein is a method for treating, ameliorating, or preventing the progression of a condition in a subject comprising administering a pharmaceutical composition comprising an oligonucleotide disclosed herein. The method generally comprises administering the oligonucleotide or composition comprising the same to a subject. The term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some embodiments, the subject is a mammal. In other embodiments, the subject is a human. The subject may have a condition associated with, mediated by, or resulting from, expression of miR-92.

In one embodiment, a method of promoting angiogenesis in a subject comprises administering to the subject an oligonucleotide disclosed herein. In one embodiment, the oligonucleotide comprises sequence at least partially complementary to miR-92. In one embodiment, the oligonucleotide is selected from Tables 1 or 2. In some embodiments, the subject suffers from ischemia, myocardial infarction, chronic ischemic heart disease, peripheral or coronary artery occlusion, ischemic infarction, stroke, atherosclerosis, acute coronary syndrome, coronary artery disease, carotid artery disease, diabetes, chronic wound(s), or peripheral vascular disease (e.g., peripheral artery disease).

In one embodiment, a method of promoting wound healing in a subject comprises administering to the subject a miR-92 inhibitor, such as an oligonucleotide disclosed herein. In one embodiment, the oligonucleotide comprises sequence at least partially complementary to miR-92. In one embodiment, the oligonucleotide is selected from Tables 1 or 2. In some embodiments, the subject suffers from diabetes. In some embodiments, healing of a chronic wound, diabetic foot ulcer, venous stasis leg ulcer or pressure sore is promoted by administration of a miR-92 inhibitor.

In one embodiment, administration of a miR-92 inhibitor as provided herein provides at least about 5%, 10%, 20%, 30%, 40%, 50%, 60%, 70%, 80%, or 90% improvement in wound re-epithelialization or wound closure as compared to a wound not administered the miR-92 inhibitor. In some embodiments, administration of a miR-92 inhibitor as provided herein provides at least about 5%, 10%, 20%, 30%, 40%, 50%, 60%, 70%, 80%, or 90% more granulation tissue formation or neovascularization as compared to a wound not administered the miR-92 inhibitor.

In one embodiment, administration of a miR-92 inhibitor as provided herein provides at least about 5%, 10%, 20%, 30%, 40%, 50%, 60%, 70%, 80%, or 90% improvement in wound re-epithelialization or wound closure as compared to a wound administered an agent known in the art for treating wounds. In some embodiments, administration of a miR-92 inhibitor as provided herein provides at least about 5%, 10%, 20%, 30%, 40%, 50%, 60%, 70%, 80%, or 90% more granulation tissue formation or neovascularization as compared to a wound administered an agent known in the art for treating wounds. The agent can be a growth factor such as for example platelet derived growth factor (PDGF) and/or vascular endothelial growth factor (VEGF).

Also provided herein is an agonist of miR-92. An agonist of miR-92 can be an oligonucleotide comprising a mature miR-92 sequence. In some embodiments, the oligonucleotide comprises the sequence of the pri-miRNA or pre-miRNA sequence for miR-92. The oligonucleotide comprising the mature miR-92, pre-miR-92, or pri-miR-92 sequence can be single stranded or double stranded. In one embodiment, the miR-92 agonist can be about 15 to about 50 nucleotides in length, about 18 to about 30 nucleotides in length, about 20 to about 25 nucleotides in length, or about 10 to about 14 nucleotides in length. The miR-92 agonist can be at least about 75%, 80%, 85%, 90%, 95%, 96%, 97%, 98%, 99%, or 100% identical to the mature, pri-miRNA or pre-miRNA sequence of miR-92. The miR-92 agonist that is a oligonucleotide can contain one or more chemical modifications, such as locked nucleic acids, peptide nucleic acids, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages. In one embodiment, the oligonucleotide comprising a miR-92 sequence is conjugated to cholesterol. The oligonucleotide comprising a miR-92 sequence can be expressed in vivo from a vector and/or operably linked to a promoter. In another embodiment, the agonist of miR-92 can be an agent distinct from miR-92 that acts to increase, supplement, or replace the function of miR-92.

The present invention further provides pharmaceutical compositions comprising an oligonucleotide disclosed herein. Where clinical applications are contemplated, pharmaceutical compositions can be prepared in a form appropriate for the intended application. Generally, this can entail preparing compositions that are essentially free of pyrogens, as well as other impurities that could be harmful to humans or animals.

In one embodiment, the pharmaceutical composition comprises an effective dose of a miR-92 inhibitor and a pharmaceutically acceptable carrier. For instance, the pharmaceutical composition comprises an effective dose or amount of an oligonucleotide of the present invention or a pharmaceutically-acceptable salt thereof, and a pharmaceutically-acceptable carrier or diluent. The oligonucleotide can be selected from Tables 1 and 2.

In some embodiments, an "effective dose" is an amount sufficient to affect a beneficial or desired clinical result. An "effective dose" can be an amount sufficient or required to substantially reduce, eliminate or ameliorate a symptom or symptoms of a disease and/or condition. This can be relative to an untreated subject. An "effective dose" can be an amount sufficient or required to slow, stabilize, prevent, or reduce the severity of a pathology in a subject. This can be relative to an untreated subject. An effective dose of an oligonucleotide disclosed herein may be from about 0.001 mg/kg to about 100 mg/kg, about 0.01 mg/kg to about 10 mg/kg, about 0.1 mg/kg to about 10 mg/kg, about 1 mg/kg to about 10 mg/kg, about 2.5 mg/kg to about 50 mg/kg, or about 5 mg/kg to about 25 mg/kg. In some embodiments, an effective dose is an amount of oligonucleotide applied to a wound area. In some embodiments, an effective dose is about 0.01 mg/cm$^2$ wound area to about 50 mg/cm$^2$ wound area mg/cm$^2$ wound area, about 0.02 mg/cm$^2$ wound area to about 20 mg/cm$^2$ wound area, about 0.1 mg/cm$^2$ wound area to about 10 mg/cm$^2$ wound area, about 1 mg/cm$^2$ wound area to about 10 mg/cm$^2$ wound area, about 2.5 mg/cm$^2$ wound area to about 50 mg/cm$^2$ wound area, or about 5 mg/cm$^2$ wound area to about 25 mg/cm$^2$ wound area, or about 0.05 to about 25 mg/cm$^2$ wound area. The precise determination of what would be considered an effective dose may be based on factors individual to each patient, including their size, age, and nature of the oligonucleotide (e.g. melting temperature, LNA content, etc.). Therefore, dosages can be readily ascertained by those of ordinary skill in the art from this disclosure and the knowledge in the art. In some embodiments, the methods comprise administering an effective dose of the pharmaceutical composition 1, 2, 3, 4, 5, or 6 times a day. In some embodiments, administration is 1, 2, 3, 4, 5, 6, or 7 times a week. In other embodiments, administration is biweekly or monthly.

Colloidal dispersion systems, such as macromolecule complexes, nanocapsules, microspheres, beads, and lipid-based systems including oil-in-water emulsions, micelles, mixed micelles, and liposomes, may be used as delivery vehicles for the oligonucleotide inhibitors of miR-92 function. Commercially available fat emulsions that are suitable for delivering the nucleic acids of the invention to cardiac and skeletal muscle tissues include Intralipid™ Liposyn™, Liposyn™ II, Liposyn™ III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900 6,383,512; 5,783,565; 7,202,227; 6,379,965; 6,127,170; 5,837,533; 6,747,014; and WO03/093449, all of which are hereby incorporated by reference in their entireties.

In certain embodiments, liposomes used for delivery are amphoteric liposomes such SMARTICLES® (Marina Biotech, Inc.) which are described in detail in U.S. Pre-grant Publication No. 20110076322. The surface charge on the SMARTICLES® is fully reversible which make them particularly suitable for the delivery of nucleic acids. SMARTICLES® can be delivered via injection, remain stable, and aggregate free and cross cell membranes to deliver the nucleic acids.

Any of the oligonucleotide inhibitors described herein (e.g., oligonucleotide inhibitors of miR-92a) can be delivered to the target cell (e.g., a fibrocyte, fibroblast, keratinocyte or endothelial cell) by delivering to the cell an expression vector encoding the oligonucleotide inhibitor. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, and the like. In one particular embodiment, the viral vector is a lentiviral vector or an adenoviral vector. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, an expression vector for expressing an oligonucleotide inhibitor described herein (e.g., oligonucleotide inhibitors of miR-92a) comprises a promoter operably linked to a polynucleotide sequence encoding the oligonucleotide inhibitor. The phrase "operably linked" or "under transcriptional control" as used herein means that the promoter is in the correct location and orientation in relation to a polynucleotide to control the initiation of transcription by RNA polymerase and expression of the polynucleotide.

As used herein, a "promoter" refers to a DNA sequence recognized by the synthetic machinery of the cell, or introduced synthetic machinery, required to initiate the specific transcription of a gene. Suitable promoters include, but are not limited to RNA pol I, pol II, pol III, and viral promoters (e.g. human cytomegalovirus (CMV) immediate early gene promoter, the SV40 early promoter, and the Rous sarcoma virus long terminal repeat). In one embodiment, the promoter is a fibroplast specific promoter such as the FSP1 promoter, etc. In another embodiment, the promoter is an endothelial specific promoter such as the ICAM-2 promoter, etc.

In certain embodiments, the promoter operably linked to a polynucleotide encoding an oligonucleotide inhibitor described herein (e.g., oligonucleotide inhibitors of miR-92a) can be an inducible promoter. Inducible promoters are known in the art and include, but are not limited to, tetracycline promoter, metallothionein IIA promoter, heat shock promoter, steroid/thyroid hormone/retinoic acid response elements, the adenovirus late promoter, and the inducible mouse mammary tumor virus LTR.

Methods of delivering expression constructs and nucleic acids to cells are known in the art and can include, for example, calcium phosphate co-precipitation, electroporation, microinjection, DEAE-dextran, lipofection, transfection employing polyamine transfection reagents, cell sonication, gene bombardment using high velocity microprojectiles, and receptor-mediated transfection.

One will generally desire to employ appropriate salts and buffers to render delivery vehicles stable and allow for uptake by target cells. Aqueous compositions of the present invention can comprise an effective amount of the delivery vehicle comprising the inhibitor polynucleotides (e.g. liposomes or other complexes or expression vectors) dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the oligonucleotides of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal, intraarterial, or intravenous injection. In some embodiments, the pharmaceutical composition is directed injected into lung or cardiac tissue. In some embodiments, the pharmaceutical composition is directly injected into the wound area. In some embodiments, the pharmaceutical composition is topically applied to the wound area.

Pharmaceutical compositions comprising a miR-92 inhibitor may also be administered by catheter systems or systems that isolate coronary/pulmonary circulation for delivering therapeutic agents to the heart and lungs. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. Nos. 6,416,510; 6,716,196; 6,953,466, WO 2005/082440, WO 2006/089340, U.S. Patent Publication No. 2007/0203445, U.S. Patent Publication No. 2006/0148742, and U.S. Patent Publication No. 2007/0060907, which are all herein incorporated by reference in their entireties. Such compositions would normally be administered as pharmaceutically acceptable compositions as described herein.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use, catheter delivery, or inhalational delivery include, for example, sterile aqueous solutions or dispersions and sterile powders for the extemporaneous preparation of sterile injectable solutions or dispersions (e.g. aerosols, nebulizer solutions). Generally, these preparations are sterile and fluid to the extent that easy injectability or aerosolization/nebulization exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In some embodiments, a composition comprising a miR-92 inhibitor is suitable for topical application, such as administration at a wound margin or wound bed. In some embodiments, the composition comprises water, saline, PBS or other aqueous solution. In some embodiments, the miR-92 inhibitor is in a lotion, cream, ointment, gel or hydrogel. In some embodiments, the composition suitable for topical application comprises macromolecule complexes, nanocapsules, microspheres, beads, or a lipid-based system (e.g., oil-in-water emulsions, micelles, mixed micelles, and liposomes) as a delivery vehicle. In yet another embodiment, the miR-92 inhibitor is in the form of a dry powder or incorporated into a wound dressing.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof. In some embodiments, sterile powders can be administered directly to the subject (i.e. without reconstitution in a diluent), for example, through an insufflator or inhalation device.

In some embodiments, administration of a miR-92 inhibitor is by subcutaneous or intradermal injection, such as to a wound (e.g., a chronic wound, diabetic foot ulcer, venous stasis leg ulcer or pressure sore). Administration may be at the site of a wound, such as to the wound margin or wound bed.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids), or from organic acids (e.g., acetic, oxalic, tartaric, mandelic, and the like). Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like).

Upon formulation, solutions are preferably administered in a manner compatible with the dosage formulation and in such amount as is therapeutically effective. The formulations may easily be administered in a variety of dosage forms such as injectable solutions, drug release capsules, unit dose inhalers, and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous, intraarterial, and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

The composition or formulation may employ a plurality of therapeutic oligonucleotides, including at least one described herein. For example, the composition or formulation may employ at least 2, 3, 4, or 5 miR-92 inhibitors described herein. In another embodiment, an oligonucleotide of the present invention may be used in combination with other therapeutic modalities. Combinations may also be achieved by contacting a cell with more than one distinct composition or formulation, at the same time. Alternatively, combinations may be administered sequentially.

In one embodiment of the present invention, an oligonucleotide inhibitor of miR-92 is used in combination with other therapeutic modalities. Examples of combination therapies include any of the foregoing. Combinations may be achieved with a single composition or pharmacological formulation that includes both agents, or with two distinct compositions or formulations, at the same time, wherein one composition includes the oligonucleotide inhibitor of miR-92 and one more other agents. Alternatively, the therapy using an oligonucleotide inhibitor of miR-92 may precede or follow administration of the other agent(s) by intervals ranging from minutes to weeks. In embodiments where the other agent and oligonucleotide inhibitor of miR-92 are applied separately to the cell, one would generally ensure that a significant period of time did not expire between the time of each delivery, such that the agent and the oligonucleotide inhibitor of miR-92 would still be able to exert an advantageously combined effect on the cell. In such instances, it is contemplated that one would typically contact the cell with both modalities within about 12-24 hours of each other, within about 6-12 hours of each other, or with a delay time of only about 12 hours. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

In one embodiment, more than one administration of the oligonucleotide inhibitor of miR-92 or the other agent(s) will be desired. In this regard, various combinations may be employed. By way of illustration, where the oligonucleotide inhibitor of miR-92 is "A" and the other agent is "B," the following permutations based on 3 and 4 total administrations are provided as examples: AB/A, B/A/B, BB/A, A/A/B, B/A/A, A/B/B, BBB/A, B/B/A/B, A/A/B/B, AB/AB, A/B/B/A, B/B/A/A, B/A/B/A, B/A/A/B, BBB/A, A/A/A/B, B/A/A/A, A/B/A/A, A/A/B/A, A/BBB, B/A/B/B, B/B/A/B. Other combinations are likewise contemplated. Specific examples of other agents and therapies are provided below.

In one embodiment of the present invention, the method of promoting angiogenesis in a subject in need thereof comprises administering to the subject a miR-92 inhibitor, such as an oligonucleotide inhibitor of miR-92 as described herein, and another agent that promotes angiogenesis. In one embodiment of the present invention, a method of treating or preventing peripheral vascular disease (e.g., peripheral artery disease) in a subject in need thereof comprises administering to the subject a miR-92 inhibitor, such as an oligonucleotide inhibitor of miR-92 as described herein. In some embodiments, the method further comprises administering another agent with an oligonucleotide inhibitor of miR-92. The other agent may promote angiogenesis or be an agent used for treating atherosclerosis or peripheral vascular disease (e.g., peripheral artery disease). The other agent may be a phosphodiesterase type 3 inhibitor (such as cilostazol), a statin, an antiplatelet, L-carnitine, propionyl-L-carnitine, pentoxifylline, or naftidrofuryl. The method of treating or preventing peripheral vascular disease (e.g., peripheral artery disease) in a subject in need thereof may also comprise administering oligonucleotide inhibitor of miR-92 to the subject, in which the subject is also receiving, or will be receiving gene therapy (e.g., with a proangiogenic factor, such as VEGF, FGF, HIF-1α, HGF, or Del-1), cell therapy, and/or antiplatelet therapy. In some embodiments, the method comprises administering oligonucleotide inhibitor of miR-92 and an antimicrobial to the subject.

In one embodiment of the present invention, the method of promoting wound healing in a subject in need thereof comprises administering to the subject a miR-92 inhibitor, such as an oligonucleotide inhibitor of miR-92 as described herein. In one embodiment, the subject has diabetes. In some embodiments, the subject has a chronic wound, diabetic foot ulcer, venous stasis leg ulcer or pressure sore. In another embodiment, the subject has peripheral vascular disease (e.g., peripheral artery disease). In some embodiments, the method further comprises administering another agent with an oligonucleotide inhibitor of miR-92. The other agent may be an agent used for treating peripheral vascular disease (e.g., peripheral artery disease), such as described above. In some embodiments, the other agent promotes wound healing or is used to treat diabetes. The other agent may be a pro-angiogenic factor. In some embodiments, the other agent is a growth factor, such as VEGF or PDGF. In some embodiments, the other agent promotes VEGF expression or activity or PDGF expression or activity. In some embodiments, the other agent is an allogeneic skin substitute or biologic dressing, (e.g., Dermagraft® or Apligraf®, available from Organogenesis, Canton, Mass.) or a platelet derived growth factor (PDGF) gel, such as becaplermin (Buchberger et al. Experimental and Clinical Endocrinology and Diabetes 119:472-479 (2011)). In some embodiments, the other agent is a debridement agent or antimicrobial agent.

The present invention is also based, in part, on the discovery of genes significantly regulated by miR-92. Accordingly, another aspect of the present invention is a method for evaluating or monitoring the efficacy of a therapeutic for modulating angiogenesis or wound healing in a subject receiving the therapeutic comprising: obtaining a sample from the subject; measuring the expression of one or more genes listed in Table 3 in the sample; and comparing the expression of the one or more genes to a pre-determined reference level or level of the one or more genes in a control sample, wherein the comparison is indicative of the efficacy of the therapeutic. In some embodiments, the therapeutic modulates miR-92 function and/or activity. The therapeutic can be a miR-92 antagonist, such as a miR-92 oligonucleotide inhibitor selected from Tables 1 and 2. In other embodiments, the therapeutic is a miR-92 agonist, such as a miR-92 mimic. In some embodiments, the subject suffers from ischemia, myocardial infarction, chronic ischemic heart disease, peripheral or coronary artery occlusion, ischemic infarction, stroke, atherosclerosis, acute coronary syndrome, coronary artery disease, carotid artery disease, or peripheral vascular disease (e.g., peripheral artery disease). In some embodiments, the subject suffers from diabetes, a chronic wound, diabetic foot ulcer, venous stasis leg ulcer or pressure sore.

In some embodiments, the method of evaluating or monitoring the efficacy of a therapeutic for modulating angiogenesis or wound healing in a subject receiving the therapeutic further comprises performing another diagnostic, assay or test evaluating angiogenesis in a subject. In some embodiments, the additional diagnostic assay or test for evaluating or monitoring the efficacy of a therapeutic for modulating angiogenesis is a walk time test, an ankle-bronchial index (ABI), arteriography or angiography on the subject, or a SPECT analysis.

Another aspect of the present invention is a method for selecting a subject for treatment with a therapeutic that modulates miR-92 function and/or activity comprising: obtaining a sample from the subject; measuring the expression of one or more genes listed in Table 3 in the sample; and comparing the expression of the one or more genes to a pre-determined reference level or level of the one or more genes in a control sample, wherein the comparison is indicative of whether the subject should be selected for treatment with the therapeutic. In some embodiments, the therapeutic is a miR-92 antagonist, such as a miR-92 oligonucleotide inhibitor selected from Tables 1 and 2. In other embodiments, the therapeutic is a miR-92 agonist, such as a miR-92 mimic. In some embodiments, the subject suffers from ischemia, myocardial infarction, chronic ischemic heart disease, peripheral or coronary artery occlusion, ischemic infarction, stroke, atherosclerosis, acute coronary syndrome, coronary artery disease, carotid artery disease, or peripheral vascular disease (e.g., peripheral artery disease). In some embodiments, the subject suffers from diabetes, a chronic wound, diabetic foot ulcer, venous stasis leg ulcer or pressure sore.

In some embodiments, the method for selecting a subject for treatment with a therapeutic that modulates miR-92 function and/or activity comprises obtaining a sample from a subject treated with the therapeutic. In some embodiments, the subject is not treated with the therapeutic and the sample is treated with the therapeutic. In some embodiments, the subject is treated with the therapeutic and the sample is treated with the therapeutic. In some embodiments, the method further comprises performing another diagnostic, assay or test evaluating angiogenesis or wound healing in a subject. In some embodiments, the additional diagnostic assay or test for evaluating angiogenesis is a walk time test, an ankle-bronchial index (ABI), arteriography or angiography on the subject, or a SPECT analysis.

The walk test can be a non-invasive treadmill test to measure the change in maximum or pain-free walk time in response to therapy. The ankle-bronchial index (ABI) can be a pressure measurement taken at the arm and the ankle, such as measured by ultrasound. The index can then be expressed as a ratio of the blood pressure at the ankle compared to the pressure at the arm. The arteriography can be a contrast dye method to measure blood flow through arteries or veins. The SPECT (Single Photon Emission Computed Tomography) analysis can be performed with a 3-D imaging system using radiation to measure blood flow through capillaries.

Also provided herein is a method for evaluating an agent's ability to promote angiogenesis or wound healing comprising: contacting a cell with the agent; measuring the expression of one or more genes listed in Table 3 in the cell contacted with the agent; and comparing the expression of the one or more genes to a pre-determined reference level or level of the one or more genes in a control sample, wherein the comparison is indicative of the agent's ability to promote angiogenesis. In some embodiments, the method further comprises determining miR-92 function and/or activity in the cell contacted with the agent. In some embodiments, the cell is a mammalian cell. In some embodiments, the cell is a cardiac or muscle cell. In some embodiments, the cell is involved in wound healing. In some embodiments, the cell is a fibrocyte, fibroblast, keratinocyte or endothelial cell. In yet other embodiments, the cell is in vivo or ex vivo.

Measuring or detecting the expression of a gene can be performed in any manner known to one skilled in the art and such techniques for measuring or detecting the level of a gene are well known and can be readily employed. Gene expression levels may be determined measuring the mRNA levels of a gene or the protein levels of a protein that the gene encodes. A variety of methods for detecting gene expression have been described and include Western blotting, Northern blotting, microarrays, electrochemical methods, bioluminescent, bioluminescent protein reassembly, BRET-based (BRET: bioluminescence resonance energy transfer), RT-PCR, fluorescence correlation spectroscopy and surface-enhanced Raman spectroscopy. Commercially available kits can also be used. The methods for detecting gene expression can include hybridization-based technology platforms and massively-parallel next generation sequencing that allow for detection of multiple gene simultaneously.

In some embodiments, a method for determining the therapeutic efficacy of a therapeutic for treating a condition (e.g., peripheral artery disease or a wound) in a subject comprises selecting a subject for treatment with a therapeutic (e.g., a miR-92 oligonucleotide inhibitor), selecting a subject for treatment with a therapeutic (e.g., a miR-92 oligonucleotide inhibitor), or evaluating an agent's ability to promote angiogenesis or wound healing; the level of one or more genes, such as selected from Table 3, is determined.

The gene expression in a sample (e.g. a sample from a subject being administered the therapeutic or a sample from a subject or cell culture, in which the sample is treated with the therapeutic), can be compared to a standard amount of the gene present in a sample from a subject with the condition or in the healthy population, each of which may be referred to as a reference level. In other embodiments, the level of gene expression is compared to level in a control sample (a sample not from a subject with the condition) or compared to the gene expression level in a sample without treatment, (e.g. taken from a subject prior to treatment with a therapeutic or a sample taken from an untreated subject, or a cell culture sample that has not been treated with the therapeutic). Standard levels for a gene can be determined by determining the gene expression level in a sufficiently large number of samples obtained from normal, healthy control subjects to obtain a pre-determined reference or threshold value. As used herein, "reference value" refers to a pre-determined value of the gene expression level ascertained from a known sample.

A standard level can also be determined by determining the gene expression level in a sample prior to treatment with the therapeutic. Further, standard level information and methods for determining standard levels can be obtained from publically available databases, as well as other sources. In some embodiments, a known quantity of another gene that is not normally present in the sample is added to the sample (i.e. the sample is spiked with a known quantity of exogenous mRNA or protein) and the level of one or more genes of interest is calculated based on the known quantity of the spiked mRNA or protein. The comparison of the measured levels of the one or more genes to a reference amount or the level of one or more of the genes in a control sample can be done by any method known to a skilled artisan.

According to the present invention, in some embodiments, a difference (increase or decrease) in the measured level of the gene relative to the level of the gene in the control sample (e.g., sample in patient prior to treatment or an untreated patient) or a predetermined reference value is indicative of the therapeutic efficacy of the therapeutic, a subject's selection for treatment with the therapeutic, or an agent's ability to promote or inhibit angiogenesis.

For instance, when the level of one or more genes selected from ACTA2, LACTB, SESN1, and KIAA1598 is decreased when compared to the level in a control sample or pre-determined reference value and/or the level of one or more genes selected from LPCAT4, MYO5A, ERGIC2, LEPREL2, SERPIND1, TSPAN8, ITGA5, NOMA///NOMO2///NOMO3, NPTN, CD93, LOC100507246, MAN2A1, CNEP1R1, EFR3A, UBE2Q2, RNF4, ATP6V1B2, FZD6, MYO1C, PPP3CB, CYYR1, EDEM1, LHFPL2, SEMA3F, UBE2Z is increased in a sample from a subject being administered a therapeutic or a sample is treated with the therapeutic, the result is indicative of the therapeutic being a miR-92 inhibitor and/or promotes angiogenesis, and/or the subject should be selected for treatment with a miR-92 therapeutic (e.g., with a miR-92 inhibitor or agonist).

In another example, when the level of one or more genes selected from ACTA2, LACTB, SESN1, and KIAA1598 is increased when compared to the level in a control sample or pre-determined reference value and/or the level of one or more genes selected from LPCAT4, MYO5A, ERGIC2, LEPREL2, SERPIND1, TSPAN8, ITGA5, NOMA///NOMO2///NOMO3, NPTN, CD93, LOC100507246, MAN2A1, CNEP1R1, EFR3A, UBE2Q2, RNF4, ATP6V1B2, FZD6, MYO1C, PPP3CB, CYYR1, EDEM1, LHFPL2, SEMA3F, UBE2Z is decreased in a sample from a subject being administered a therapeutic or a sample is treated with the therapeutic, the result is indicative of the therapeutic being a miR-92 agonist and/or inhibits angiogenesis, and/or the subject should be selected for treatment with a miR-92 therapeutic (e.g., with a miR-92 inhibitor or agonist).

Sampling methods are well known by those skilled in the art and any applicable techniques for obtaining biological samples of any type are contemplated and can be employed with the methods of the present invention. (See, e.g., Clinical Proteolytics: Methods and Protocols, Vol. 428 in Methods in Molecular Biology, Ed. Antonia Vlahou (2008),) Samples can include any biological sample from which mRNA or protein can be isolated. Such samples can include serum, blood, plasma, whole blood and derivatives thereof, cardiac tissue, muscle, skin, hair, hair follicles, saliva, oral mucous, vaginal mucous, sweat, tears, epithelial tissues, urine, semen, seminal fluid, seminal plasma, prostatic fluid, pre-ejaculatory fluid (Cowper's fluid), excreta, biopsy, ascites, cerebrospinal fluid, lymph, cardiac tissue, as well as other tissue extract samples or biopsies, in some embodiments, the biological sample is plasma or serum.

The biological sample for use in the disclosed methods can be obtained from the subject at any point following the start of the administration of the therapeutic. In some embodiments, the sample is obtained at least 1, 2, 3, or 6 months following the start of the therapeutic intervention. In some embodiments, the sample is obtained least 1, 2, 3, 4, 6 or 8 weeks following the start of the therapeutic intervention. In some embodiments, the sample is obtained at least 1, 2, 3, 4, 5, 6, or 7 days following the start of the therapeutic intervention. In some embodiments, the sample is obtained at least 1 hour, 6 hours, 12 hours, 18 hours or 24 hours after the start of the therapeutic intervention. In other embodiments, the sample is obtained at least one week following the start of the therapeutic intervention.

The methods of the present invention can also include methods for altering the treatment regimen of a therapeutic. Altering the treatment regimen can include but is not limited to changing and/or modifying the type of therapeutic intervention, the dosage at which the therapeutic intervention is administered, the frequency of administration of the therapeutic intervention, the route of administration of the therapeutic intervention, as well as any other parameters that would be well known by a physician to change and/or modify.

In some embodiments, the treatment efficacy can be used to determine whether to continue a therapeutic intervention. In some embodiments the treatment efficacy can be used to determine whether to discontinue a therapeutic intervention. In some embodiments the treatment efficacy can be used to determine whether to modify a therapeutic intervention. In some embodiments the treatment efficacy can be used to determine whether to increase or decrease the dosage of a therapeutic intervention. In some embodiments the treatment efficacy can be used to determine whether to change the dosing frequency of a therapeutic intervention. In some embodiments, the treatment efficacy can be used to determine whether to change the number or the frequency of administration of the therapeutic intervention. In some embodiments, the treatment efficacy can be used to determine whether to change the number of doses per day, per week, times per day. In some embodiments the treatment efficacy can be used to determine whether to change the dosage amount.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

EXAMPLES

Example 1. Multiple Genes are Significantly Regulated by miR-92a Modulation in HUVECs HUVECs were transfected with miR-92a (1 nM) or oligonucleotide inhibitor of miR-92a (compound A; SEQ ID NO: 7; 10 nM) via lipid-mediated transfection, and RNA was isolated 48 hours later for expression profiling. Three individual replicates for each treatment were profiled. One sample for miR-92a treatment failed QC and was therefore eliminated from the analysis. The genes were selected on the basis of differential expression (FDR p-value<=0.05) for miR-92a treatment versus untreated cells. Intriguingly, as shown in FIG. 1, this signature of genes is reciprocally regulated by the oligonucleotide inhibitor of miR-92a. The fact that the entire signature of genes is reciprocally regulated by the antimiR is striking. All of the genes that are down-regulated by miR-92a mimic are up-regulated by the oligonucleotide inhibitor of miR-92a, and the genes up-regulated in response to miR-92a mimic are down-regulated by the oligonucleotide inhibitor of miR-92a. These genes are listed in Table 3.

TABLE 3

Genes significantly regulated by miR-92a modulation

| Alternative Name | Gene Symbol |
| --- | --- |
| actin, alpha 2, smooth muscle aorta | ACTA2 |
| lysophosphatidylcholine acyltransferase 4 | LPCAT4 |
| myosin VA | MYO5A |
| ERGIC and golgi 2 | ERGIC2 |
| prolyl 3-hydroxylase 3 | LEPREL2 |
| Heparin cofactor II | SERPIND1 |
| Tetraspanin 8 | TSPAN8 |
| Integrin a5 | ITGA5 |
| NODAL modulator 1/// NODAL modulator 2/// NODAL modulator 3 | NOMO1///NOMO2///NOMO3 |
| neuroplastin | NPTN |
| CD93 molecule | CD93 LOC100507246 |
| mannosidase, alpha, class 2A, member 1 | MAN2A1 |
| CTD nuclear envelope phosphatase 1 regulatory subunit 1 | CNEP1R1 |
| EFR3 homolog A | EFR3A |
| ubiquitin conjugating enzyme E2Q family member 2 | UBE2Q2 |
| ring finger protein 4 | RNF4 |
| ATPase, H+ transporting, lysosomal 56/58 kDa, V1 subunit B2 | ATP6V1B2 |
| Frizzled homolog 6 (Drosophila) | FZD6 |
| Myosin VA | MYO1C |
| lactamase beta | LACTB |
| sestrin 1 | SESN1 |
| protein phosphatase 3, catalytic subunit, beta isozyme | PPP3CB |
| cysteine/tyrosine-rich 1 | CYYR1 |
| ER degradation enhancer, mannosidase alpha-like 1 | EDEM1 |
| lipoma HMGIC fusion partner-like 2 | LHFPL2 |
| sema domain, immunoglobulin domain (Ig), short basic domain, secreted, (semaphorin) 3F | SEMA3F |
| shootin 1 | SHTN1 (KIAA1598) |
| ubiquitin conjugating enzyme E2Z | UBE2Z |

Genes shown in FIG. 1 and listed in Table 3 were subjected to a PubMed literature search to identify their potential functions. The genes that have been reported to have a function in vascular angiogenesis are listed in Table 4. Table 4 also shows the fold-change of the gene expression in response to antimiR or miR transfection, as well as whether or not the 3'UTR of the gene contains a seed sequence targeted by miR-92a.

mRNA following lipid-mediated transfection was examined by extracting the total RNA from the HUVEC cells followed by RT-PCR. The relative expression of integrin α5 mRNA in response to miR-92a inhibitors or mimic was normalized to HUVECs transfected with lipid without oligonucleotide.

TABLE 4

Significantly regulated genes have roles in vascular angiogenesis

| Gene symbol | Alternative name | Fold-change antimiR | Fold-change mimic | Seed-matched target | Reported angiogenesis function |
|---|---|---|---|---|---|
| SERPIND1 | Heparin cofactor II | 1.87 | −2.59 | | promotes angiogenesis |
| ITGA5 | Integrin α5 | 1.38 | −2.13 | ✓ | promotes angiogenesis |
| TSPAN8 | Tetraspanin 8 | 1.36 | −2.60 | | promotes angiogenesis, downregulated in PAD samples |
| FZD6 | Frizzled homolog 6 (*Drosophila*) | 1.15 | −1.27 | ✓ | implicated in angiogenesis |
| CD93 | CD93 molecule | 1.07 | −1.28 | ✓ | promotes angiogenesis |
| MYO1C | Myosin VA | 1.05 | −1.33 | ✓ | implicated in angiogenesis |

Example 2. Confirmation of Gene Regulation by miR-92a Modulation in HUVECs

As described in Example 1, HUVECs were transfected with miR-92a (5 nM) or oligonucleotide inhibitor of miR-92a (antagomiR; A (SEQ ID NO. 7); B (SEQ ID NO. 63); C (SEQ ID NO. 64); 5 nM each) via lipid-mediated transfection. 24 hours after transfection, RNA was isolated regulation of targets identified by microarray profiling in Example 1 was assessed by real time PCR. As shown in FIG. 3, four genes identified by microarray profiling are increased in response to miR-92a inhibition and decreased in response to miR-92a mimic, in an independent HUVEC lipid-transfection experiment. The radar plot in FIG. 3 indicates the relative expression of MAN2A1, CNEP1R1, ERGIC2, and CD93 in response to miR-92a inhibitor or mimic, normalized to HUVECs transfected with lipid without oligonucleotide. The thick black line indicates where the gene expression would be if there were no change, the arrow marks the line that indicates the gene expression in response to D control oligo transfection.

Example 3. Regulation of Integrin α5 Expression by miR-92a in HUVECs

The regulation of integrin α5 by miR-92a modulation was examined in HUVECs via lipid-mediated transfection (FIG. 2A) or passive delivery (FIG. 2B) of miR-92a (mimic) or antimiR-92a oligonucleotides (antagomiR; A (SEQ ID NO. 7); B (SEQ ID NO. 63); C (SEQ ID NO. 64)) at various concentrations. For lipid-mediated transfection, the agents were transfected at 1 nM, 5, nM, 25 nM, or 50 nM, while for passive delivery of the oligonucleotides, the cells were exposed to the oligonucleotides shown in FIG. 2B at a concentration of 0.01 uM, 0.1 uM, or 1 uM. As shown in FIG. 2A, at 24 hours post-lipid-mediated transfection, the relative expression of integrin α5 mRNA was increased in response to miR-92a inhibition and decreased in response to miR-92a mimic. The relative expression of integrin α5

As shown in FIG. 2B, at 72 hours post passive delivery, the relative expression of integrin α5 was increased vs. the control oligonucleotide at higher concentrations of oligonucleotides. The relative expression of integrin α5 mRNA following passive delivery was examined by extracting the total RNA from the HUVEC cells followed by RT-PCR. The relative expression of integrin α5 mRNA in response to miR-92a inhibitors or mimic was normalized to HUVECs transfected without oligonucleotide. In addition to the examination of the relative mRNA levels, the relative expression of the integrin α5 protein was examined in the lipid mediated transfection experiments. Similar to the mRNA expression results, the relative expression of integrin α5 protein 24-hours post lipid-mediated transfection also increased following miR-92a inhibition and decreased in response to miR-92a mimic (see FIG. 2C). The relative expression of integrin α5 protein following lipid-mediated transfection was examined by extracting protein from the HUVEC cells followed by Western Blot analysis. The relative expression of integrin α5 protein in response to miR-92a inhibitors or mimic was normalized to untreated HUVECs.

Example 4. Dual Luciferase Assays for Testing of miR-92 Inhibitor Design Activity MiR-92 inhibitors were co-transfected at the indicated concentration with a dual-luciferase reporter (FIG. 4). The luciferase reporter contains the binding site to the miR-92a seed sequence in the 3' UTR of the gene, therefore, increased luciferase activity indicates increased miR-92a inhibition. Luciferase activity was measured 48 hours after transfection. Because all inhibitors showed activity at the 2 nM and 0.2 nM dose, the 0.02 nM dose was used to rank-order the inhibitors. Within each inhibitor group in FIG. 4, the 2 nM dose is represented by the left bar, while the 0.2 nM dose is the middle bar and the 0.02 nM dose is the right bar.

Figure 9:
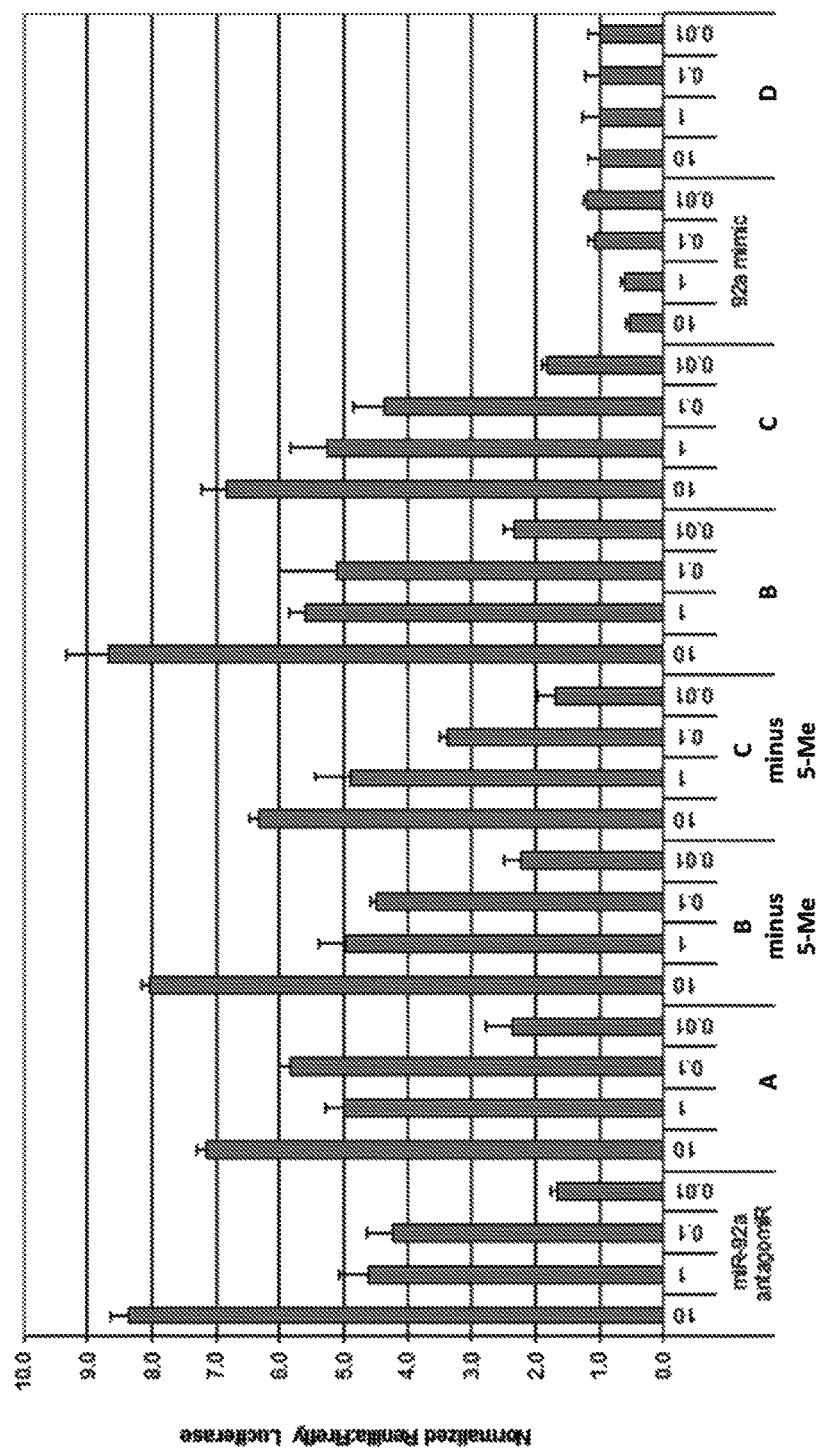
FIG. 9 illustrates a dual luciferase assay for testing of the effect of the presence of 5-methylcytosine on inhibitor design activity. MiR-92a inhibitors with or without 5-methylcytosine were analyzed based on their ability to de-repress the expression of luciferase from a dual-luciferase reporter plasmid. Shown is an example set of data.

In addition, the effect of the presence of a chemically modified nitrogenous base, such as for example 5-methylcytosine, on the activity of miR-92 oligonucleotide inhibitors was also tested. To compare the activity of miR-92 inhibitors with or without 5-methylcytosine, HeLa cells were co-transfected with a dual luciferase reporter and either a miR-92a antagomiR, compound A (A; SEQ ID NO. 7), compound B (B; SEQ ID NO. 63), compound B lacking 5-methylcytosine (B minus 5-Me; SEQ ID NO. 8), compound C (C; SEQ ID NO. 64), compound C lacking 5-methylcytosine (C minus 5-Me; SEQ ID NO. 9), compound D (D) or a miR-92a mimic as shown in FIG. 9. The HeLa cells were transfected with the compounds at the concentrations indicated in FIG. 9 (i.e., 10 nM, 1 nM, 0.1 nM, or 0.01 nM). As described herein, the luciferase reporter contains the binding site to the miR-92a seed sequence in the 3' UTR of the gene, therefore, increased luciferase activity indicates increased miR-92a inhibition. Normalized luciferase activity was assessed by measurement of luminescence. Luciferase activity was measured 48 hours after transfection. A two-way ANOVA analysis across the entire dose-curve for each compound revealed that there is a statistically-significant difference between compound B and B minus 5-Me, where compound B was more active than B minus 5-Me (p-value of <0.05 by two-way ANOVA with Hom-Sidak multiple comparison post-hoc test). A similar analysis showed a statistically-significant difference between compound C minus 5-methylcytosine to compound C was also observed with a p-value of less than 0.05 (two-way ANOVA with Hom-Sidak multiple comparison post-hoc test). Compound C was more active than C minus 5-Me.

Example 5: Activity of antimiR-92 Compounds in an In Vivo Model of Impaired Wound Healing AntimiR-92 compounds (i.e., miR-92a oligonucleotide inhibitors) were tested in an in vivo chronic wound model for increases in wound angiogenesis, and acceleration of wound healing. Db/db (BKS.Cg Dock(Hom) 7m+/+ Leprdb/j) mice have been shown to develop type II diabetes and wound healing impairments by 6 weeks of age. In two separate studies, age and sex matched adult mice were anesthetized and the dorsum was depilated. Two 6 mm diameter excisional punch wounds were made on the backs of the mice equidistant between shoulders and hips, on either side of the spine, and the wounds were covered with a semi-occlusive dressing.

Compounds at a dose of 100 nmol (~0.55 mg)/wound were applied at the time of surgery, and on post-operative days 2, 4 and 8 via intradermal injection at multiple sites around the wound margin. Recombinant human VEGF (i.e., rhVEGF-165) at a dose of 1 μg/wound and recombinant PDGF-B (i.e., rhPDGF-B) at a dose of 2 μg/wound were used as positive controls for enhanced wound healing. Mice or mice administered a vehicle control (i.e., phosphate buffered saline (PBS)) were used as negative controls.

Animals were sacrificed at day 10 post-surgery. Histology analysis was performed in order to assess the percentage of reepithelialization, the percentage of granulation tissue ingrowth, and the thickness and cross-sectional area of neo-epithelium and granulation tissue. Histology analysis was performed by fixing one half of each skin wound in 10% neutral buffered formalin for 24 hours and embedding in paraffin according to standard protocols. 4 um tissue sections were deparaffinized and stained with hematoxylin and eosin. Histology images were taken under 4-20× magnification and images were analyzed for percentage reepithelialization, percentage of granulation tissue ingrowth, area and thickness and cross-sectional area of neo-epithelium and granulation tissue using ImageJ (NCBI).

Figure 5A:
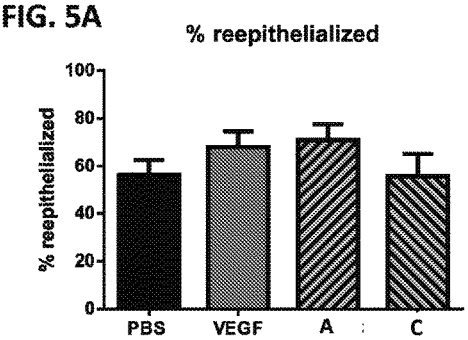
FIG. 5A-F illustrates results of a first study examining the activity of oligonucleotide inhibitors of miR-92 in an in vivo model of impaired wound healing.
Figure 5B:
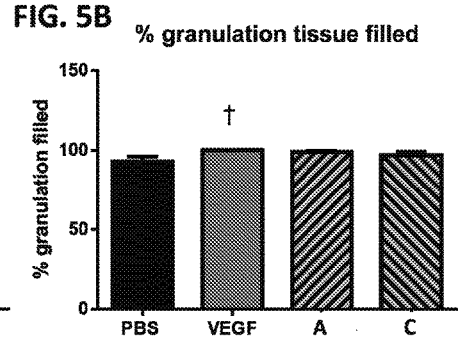
Figure 5C:
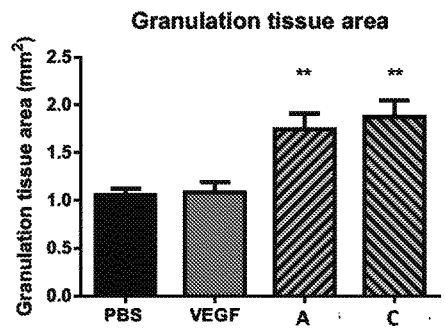
Figure 5D:
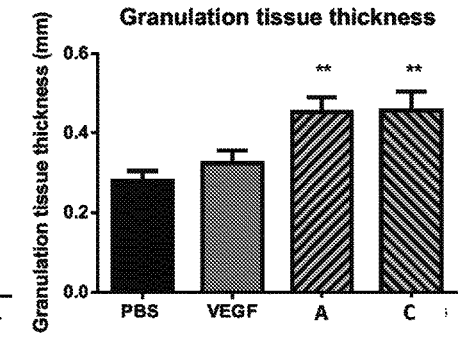
Figure 5E:
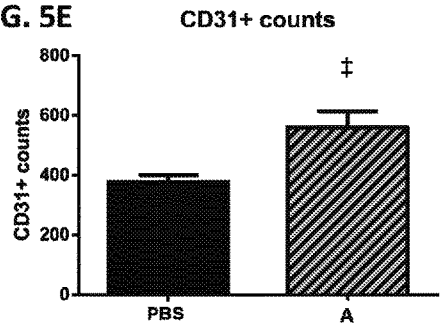
Figure 5F:
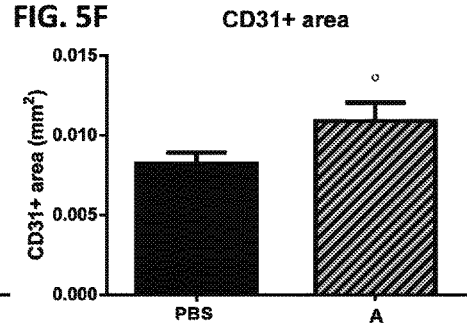

Data from the two studies are presented in FIG. 5A-F and FIG. 6A-F, respectively. FIGS. 5A and 6A illustrate the percent re-epithelialization ((1−[epithelial gap divided by wound width])×100), while FIGS. 5B and 6B show the percent of each wound that was filled with granulation tissue ((1−[granulation tissue gap divided by wound width])×100), FIGS. 5C and 6C show the granulation tissue area within the wound, and FIGS. 5D and 6D show the average thickness of granulation tissue within the wound. VEGF-165 non-significantly increased wound re-epithelialization (FIGS. 5A and 6A) and granulation tissue thickness (FIGS. 5D and 6D), while significantly increasing the percent of each wound that was filled with granulation tissue (FIGS. 5B and 6B). PDGF-B significantly increased wound re-epithelialization (FIG. 6A) and granulation tissue ingrowth (FIG. 6B), with a non-significant increase in granulation tissue area (see FIG. 6C) and thickness (FIG. 6D). Conversely, oligonucleotide inhibitors of miR-92 A and C significantly increased granulation tissue formation (% granulation tissue filled (FIG. 6B), granulation tissue area (FIGS. 5B and 6B) and average granulation tissue thickness (FIGS. 5D and 6D), with A showing some increase in wound re-epithelialization as well (FIGS. 5A and 6A). These results show that multiple oligonucleotide inhibitors of miR-92 accelerated wound healing and new tissue formation to an extent that was greater than either VEGF or PDGF peptides.

The mechanism by which oligonucleotide inhibitors of miR-92 accelerates healing of chronic wounds is believed to be due to increased angiogenesis. Immunohistochemistry was performed on a subset of groups from the two db/db wound healing studies to assess blood vessel ingrowth and number of endothelial cells, as a measure of neovascularization/angiogenesis. Immunohistochemistry was performed by staining 4 μm deparaffinized tissue sections with a primary antibody specific for CD31, followed either by fluorescent secondary antibodies and DAPI to visualize nuclei (first study), or by HRP-conjugated secondary antibodies followed by staining with DAB and hematoxylin to visualize immunocomplexes and nuclei, respectively (second study). Fluorescent images or chromogenic images were taken under 4-20× magnification and the number of CD31+ endothelial cells and blood vessels were counted at the wound margin using automated thresholding and image analysis macros in ImageJ. These data are presented in FIG. 5E for the first study and FIG. 6E for the second study. Similarly, the area of the tissue that was CD31+ was calculated in an automated fashion using ImageJ and is presented in FIG. 5F for the first study and FIG. 6F for the second study. Both studies demonstrated a significant increase in CD31+ endothelial cells and tissue area that was CD31+ with oligonucleotide inhibitor of miR-92 treatment. PDGF treatment did not accelerate neoangiogenesis in this study.

Figure 7:
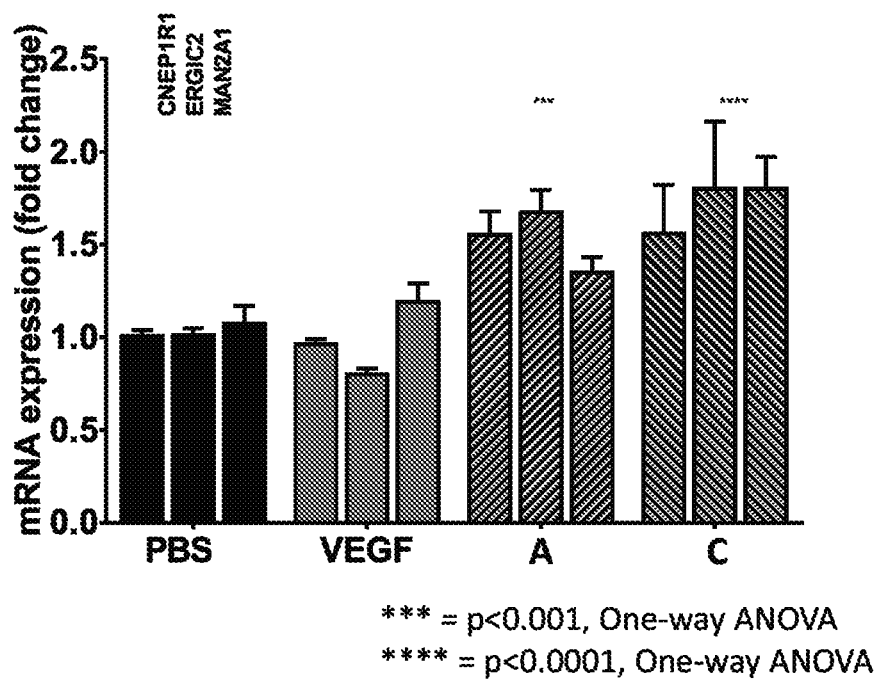
FIG. 7 illustrates de-repression of selected miR-92a target genes by oligonucleotide inhibitors of miR-92a from one in vivo study in db/db mouse excisional wounds as assessed by quantitative RT-PCR.

The effect of compounds on the mRNA expression of miR-92 target genes (e.g., listed in Table 3) is was measured via quantitative RT-PCR. Total RNA was isolated from 10-50 mg of skin tissue by homogenizing the tissue with 1 ml of TRIzol reagent (Life Technologies) in an Omni BeadRuptor. Total RNA isolation was performed per manufacturer's instructions (Life Technologies). RNA concentration was measured on a NanoDrop 1000 (Thermo). Gene expression was measured with quantitative Real-Time Polymerase Chain Reaction analysis (RT-PCR). For RT-PCR analysis of in vivo tissue samples, 100 ng of total RNA was reverse transcribed by MultiScribe RT (Life Technologies)

according to the manufacturer's specifications. Gene expression was measured with Life Technologies Taqman gene expression assays. Gene expression was normalized to a housekeeping gene such as GAPDH and calculated as relative expression compared to the average of the control group. FIG. 7 presents the de-repression of selected miR-92a target genes by oligonucleotide inhibitors of miR-92 from one in vivo study in db/db mouse excisional wounds.

The effect of compounds on the protein expression of the miR-92 target ITGA5 was evaluated using immunohistochemistry. Immunohistochemistry was performed by staining 4 μm deparaffinized tissue sections with a primary antibody specific for ITGA5, followed by HRP-conjugated secondary antibodies and then by staining with DAB and hematoxylin to visualize immunocomplexes and nuclei, respectively. Chromogenic images were taken under 4-20× magnification. Representative sections are presented in FIG. 8A-D. Little staining was seen in PBS (FIG. 8A) or rhPDGF (FIG. 8B) treated db/db mouse wounds, whereas oligonucleotide inhibitor of miR-92 treated (e.g., compound A in FIG. 8C-D) wounds showed high levels of staining, localized to endothelial cells and blood vessel walls. Arrows indicate selected blood vessels in all images; note the lack of staining in PBS and PDGF groups and the high degree of staining in A treated wounds. This indicates de-repression of the miR-92a target ITGA5 by antimiR-92a oligonucleotides.

The antimiR-92 compounds enhanced wound healing as compared to the negative control and as compared to rhVEGF or rhPDGF. The miR-92a targets listed in Table 3 were modulated in the mice administered the oligonucleotide inhibitors of miR-92 that enhance wound healing.

All publications, patents, and patent applications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for promoting wound healing in a subject comprising administering an oligonucleotide comprising a sequence that is at least 75% complementary to miR-92, wherein the subject suffers from a wound, wherein the wound is a chronic wound, a venous stasis leg ulcer, or a pressure sore and wherein the administration of the oligonucleotide reduces function or activity of miR-92, thereby promoting wound healing.

2. The method of claim 1, wherein the oligonucleotide comprises at least one locked nucleic acid (LNA) containing a 2' to 4' methylene bridge.

3. The method of claim 1, wherein the oligonucleotide comprising a sequence that is at least partially complementary to miR-92 comprises a sequence of at least 16 nucleotides, wherein the sequence comprises no more than three contiguous LNAs, wherein from the 5' end to the 3' end, positions 1, 6, 10, 11, 13 and 16 of the sequence are LNAs.

4. The method of claim 3, wherein from the 5' end to the 3' end, the sequence further comprises LNAs at positions 3, 9, and 14.

5. The method of claim 3, wherein from the 5' end to the 3' end, the sequence further comprises LNAs at positions 3, 8, and 14.

6. The method of claim 3, wherein from the 5' end to the 3' end, the sequence further comprises LNAs at positions 5, 8, and 15.

7. The method of claim 4, wherein from the 5' end to the 3' end, the sequence further comprises a deoxyribonucleic acid (DNA) nucleotide at the second nucleotide position.

8. The method of claim 7, wherein the DNA nucleotide at the second nucleotide position contains a chemically modified nitrogenous base, wherein the chemically modified nitrogenous base is 5-methylcytosine.

9. The method of claim 1, wherein the oligonucleotide comprises any one of SEQ ID NOs: 7-164, as provided in Table 1 and Table 2.

10. The method of claim 1, wherein the administration of the oligonucleotide produces an increased rate of re-epithelialization, granulation, and/or neoangiogenesis during wound healing as compared to no treatment or treatment with an agent known to promote wound healing.

11. The method of claim 10, wherein the agent known to promote wound healing is platelet derived growth factor (PDGF) or vascular endothelial growth factor (VEGF).

12. A method of treating one or more chronic wounds, comprising administering to the subject a oligonucleotide comprising any one of SEQ ID NOs: 7-164, as provided in Table 1 and Table 2.

13. The method of claim 5, wherein from the 5' end to the 3' end, the sequence further comprises a deoxyribonucleic acid (DNA) nucleotide at the second nucleotide position.

14. The method of claim 13, wherein the DNA nucleotide at the second nucleotide position contains a chemically modified nitrogenous base, wherein the chemically modified nitrogenous base is 5-methylcytosine.

15. The method of claim 6, wherein from the 5' end to the 3' end, the sequence further comprises a deoxyribonucleic acid (DNA) nucleotide at the second nucleotide position.

16. The method of claim 6, wherein the DNA nucleotide at the second nucleotide position contains a chemically modified nitrogenous base.

17. The method of claim 1, wherein the subject suffers from a diabetic wound.

18. The method of claim 1, wherein the subject suffers from a non-diabetic wound.

19. The method of claim 1, wherein the subject is human.

20. The method of claim 1, wherein the oligonucleotide comprises a sequence that is at least 85% complementary to miR-92.

21. The method of claim 1, wherein the oligonucleotide comprises a sequence that is at least 95% complementary to miR-92.

22. The method of claim 1, wherein the oligonucleotide comprises a sequence that is 100% complementary to miR-92.

23. The method of claim 1, wherein the administration comprises intradermal administration.

24. The method of claim 1, wherein the administration comprises subcutaneous administration.

25. The method of claim 1, wherein the administration comprises intramuscular administration.

26. The method of claim 1, wherein the administration comprises intravenous administration.

27. The method of claim 1, wherein the administration comprises intradermal injection.

28. The method of claim 1, wherein the administration comprises topical application.

29. The method of claim 3, wherein the oligonucleotide is lCs;dCs;lGs;dGs;dGs;lAs;dCs;lAs;dAs;Gs;lTs;dGs;lCs;lAs;dAs;lT (SEQ ID NO: 7).

30. The method of claim 3, wherein the oligonucleotide is lCs;dCs;dGs;dGs;lGs;lAs;dCs;lAs;dAs;lGs;lTs;dGs;lCs;dAs;lAs;lT (SEQ ID NO: 8).

31. The method of claim 3, wherein the oligonucleotide is lCs;dCs;lGs;dGs;dGs;lAs;dCs;dAs;lAs;lGs;lTs;dGs;lCs;lAs;dAs;lT (SEQ ID NO: 9).

32. The method of claim 3, wherein the oligonucleotide is lCs;mdCs;lGs;dGs;dGs;lAs;dCs;dAs;lAs;lGs;lTs;dGs;lCs;lAs;dAs;lT (SEQ ID NO: 64).

33. The method of claim 3, wherein the oligonucleotide is lCs;mdCs;lGs;dGs;dGs;lAs;dCs;lAs;dAs;lGs;lTs;dGs;lCs;lAs;dAs;lT (SEQ ID NO: 65).

34. The method of claim 3, wherein the oligonucleotide is lGs;dGs;lAs;dCs;lAs;dAs;dGs;lTs;dGs;lCs;dAs;lAs;lT (SEQ ID NO: 107).

35. The method of claim 3, wherein the oligonucleotide is lGs;lAs;dCs;dAs;lAs;lGs;lTs;dGs;lCs;lAs;dAs;lT (SEQ ID NO: 118).

36. The method of claim 12, wherein the oligonucleotide is lCs;dCs;lGs;dGs;dGs;lAs;dCs;lAs;dAs;lGs;lTs;dGs;lCs;lAs;dAs;lT (SEQ ID NO: 7).

37. The method of claim 12, wherein the oligonucleotide is lCs;dCs;dGs;dGs;lGs;lAs;dCs;lAs;dAs;lGs;lTs;dGs;lCs;dAs;lAs;lT (SEQ ID NO: 8).

38. The method of claim 12, wherein the oligonucleotide is lCs;dCs;lGs;dGs;dGs;lAs;dCs;dAs;lAs;lGs;lTs;dGs;lCs;lAs;dAs;lT (SEQ ID NO: 9).

39. The method of claim 12, wherein the oligonucleotide is lCs;mdCs;lGs;dGs;dGs;lAs;dCs;dAs;lAs;lGs;lTs;dGs;lCs;lAs;dAs;lT (SEQ ID NO: 64).

40. The method of claim 12, wherein the oligonucleotide is lCs;mdCs;lGs;dGs;dGs;lAs;dCs;lAs;dAs;lGs;lTs;dGs;lCs;lAs;dAs;lT (SEQ ID NO: 65).

41. The method of claim 12, wherein the oligonucleotide is lGs;dGs;lAs;dCs;lAs;dAs;dGs;lTs;dGs;lCs;dAs;lAs;lT (SEQ ID NO: 107).

42. The method of claim 12, wherein the oligonucleotide is lGs;lAs;dCs;dAs;lAs;lGs;lTs;dGs;lCs;lAs;dAs;lT (SEQ ID NO: 118).

* * * * *